US008815229B2

(12) United States Patent
Krensky et al.

(10) Patent No.: US 8,815,229 B2
(45) Date of Patent: Aug. 26, 2014

(54) GRANULYSIN IN IMMUNOTHERAPY

(75) Inventors: Alan M. Krensky, Bethesda, MD (US);
Carol Clayberger, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 93 days.

(21) Appl. No.: 13/501,726

(22) PCT Filed: Oct. 8, 2010

(86) PCT No.: PCT/US2010/052036
§ 371 (c)(1),
(2), (4) Date: Apr. 12, 2012

(87) PCT Pub. No.: WO2011/046832
PCT Pub. Date: Apr. 21, 2011

(65) Prior Publication Data
US 2012/0195854 A1 Aug. 2, 2012

Related U.S. Application Data

(60) Provisional application No. 61/250,601, filed on Oct. 12, 2009.

(51) Int. Cl.
A61K 38/17 (2006.01)
C07K 14/705 (2006.01)

(52) U.S. Cl.
USPC ...................................... 424/85.2; 424/184.1

(58) Field of Classification Search
CPC .............................. A61K 38/07; C07K 14/705
See application file for complete search history.

(56) References Cited

U.S. PATENT DOCUMENTS

| 4,994,369 | A | 2/1991 | Krensky et al. |
| 6,423,539 | B2 | 7/2002 | Fong et al. |
| 6,485,928 | B2 | 11/2002 | Stenger et al. |
| 6,607,722 | B2 | 8/2003 | Edelson et al. |
| 6,821,510 | B2 | 11/2004 | Hellstrand et al. |
| 6,893,633 | B2 | 5/2005 | Hellstrand et al. |
| 7,354,909 | B2 | 4/2008 | Klinman et al. |
| 2003/0082806 | A1 | 5/2003 | Berenson et al. |
| 2005/0239699 | A1 | 10/2005 | Okada et al. |
| 2005/0249699 | A1 | 11/2005 | Stoff et al. |
| 2006/0128623 | A1 | 6/2006 | Modlin et al. |
| 2006/0287232 | A1 | 12/2006 | Clayberger et al. |
| 2007/0025958 | A1 | 2/2007 | Hadden |
| 2008/0050382 | A1 | 2/2008 | Chen et al. |
| 2008/0176818 | A1 | 7/2008 | Puzo et al. |
| 2008/0254537 | A1 | 10/2008 | Boynton et al. |

FOREIGN PATENT DOCUMENTS

WO WO 2004/076651 9/2004

OTHER PUBLICATIONS

Breast Cancer Startup Challenge. 2013; www.breastcancerstartupchallenge.com/5-immunotherapy-using-granulysin-activated-monocytes.html.*
Zitvogel et al., "The multifaceted granulysin," *Blood*, vol. 116, No. 18, pp. 3379-3380, 2010.
Chapuis et al., "Differentiation of human dendritic cells from monocytes in vitro," *Eur. J. Immunol.* vol. 27, pp. 431-441, 1997.
Chung et al., "Granulysin is a key mediator for disseminated keratinocyte death in Stevens-Johnson syndrome and toxic epidermal necrolysis," *Nature Med.* vol. 14, pp. 1343-1350, 2008.
Deng et al., "Granulysin, a cytolytic molecule, is also a chemoattractant and proinflammatory activator," *J. Immunol.* vol. 174, pp. 5243-5248, 2005.
Han et al., Evaluation of 3 clinical dendritic cell maturation protocols containing lipopolysaccharide and interferon-γ, *J. Immunother.* vol. 32, pp. 399-407, 2009.
Huang et al., "Granulysin-mediated tumor rejection in transgenic mice," *J. Immunol.* vol. 178, pp. 77-84, 2007.
Krensky and Clayberger, "Granulysin: a novel host defense molecule," *Am. J. Transpl.* vol. 5, pp. 1789-1792, 2005.
Krensky and Clayberger, "Biology and clinical relevance of granulysin," *Tissue Antigens* vol. 73, pp. 193-198, 2009.
Latinovic-Golic et al., "Expression, processing and transcriptional regulation of granulysin in short-term activated human lymphocytes," *BMC Immunol.* 8:9 (12 pages), 2007.
Nagasawa et al., "Transient increase of serum granulysin in a stage IVs neuroblastoma patient during spontaneous regression: case report," *Int. J. Hematol.* vol. 82, pp. 456-457, 2005.
Ochoa et al., "T-cell release of granulysin contributes to host defense in leprosy," *Nature Med.* vol. 7, pp. 174-179, 2001.
Ogawa et al., "Granulysin in human serum as a marker of cell-mediated immunity," *Eur. J. Immunol.* vol. 33, pp. 1925-1933, 2003.
Pages et al., "Effector memory T cells, early metastasis, and survival in colorectal cancer," *N. Engl. J. Med.* vol. 353, pp. 2654-2666, 2005.
Pena et al., "Processing, subcellular localization, and function of 519 (granulysin), a human late T cell activation molecule with homology to small, lytic, granule proteins," vol. 1158, pp. 2680-2688, 1997.
Rutella et al., "Tolerogenic dendritic cells: cytokine modulation comes of age," *Blood* vol. 108, pp. 1435-1440, 2006.
Saigusa et al., "Serum granulysin levels as a novel prognostic marker in patients with gastric carcinoma," *J. Gastroenterol. Hepatol.* vol. 22, pp. 1322-1327, 2007.
Sallusto and Lanzavecchia, "Efficient presentation of soluble antigen by cultured human dendritic cells is maintained by granulocyte/macrophage colony-stimulating factor plus interleukin 4 and downregulated by tumor necrosis factor α," *J. Exp. Med.* vol. 179, pp. 1109-1118, 1994.

* cited by examiner

*Primary Examiner* — Karen Cochrane Carlson
(74) *Attorney, Agent, or Firm* — Klarquist Sparkman, LLP

(57) ABSTRACT

Methods of stimulating or enhancing an immune response in a host are disclosed. The methods include contacting a monocyte with 15 kD granulysin thereby producing a monocyte-derived dendritic cell. In one example, the method further includes contacting the monocyte or monocyte-derived dendritic cell with a target antigen, such as a tumor antigen or an autoimmune antigen. In another embodiment, the method includes contacting the monocyte with an additional agent that enhances maturation of dendritic cells or induces immunological tolerance. The methods are of use in vivo, in vitro and ex vivo. In another aspect, the disclosure relates to compositions and methods for the treatment of tumors.

9 Claims, 14 Drawing Sheets

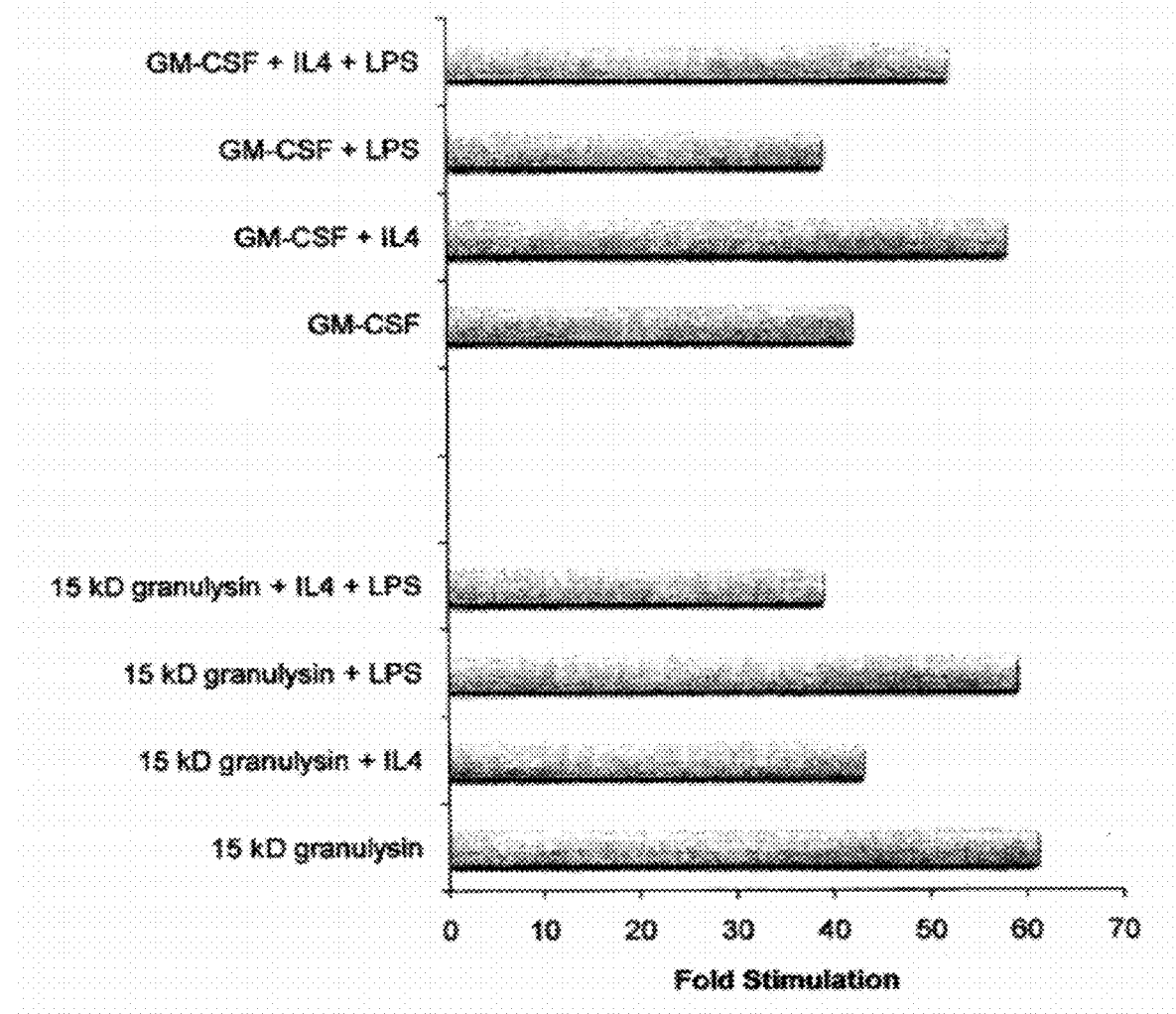

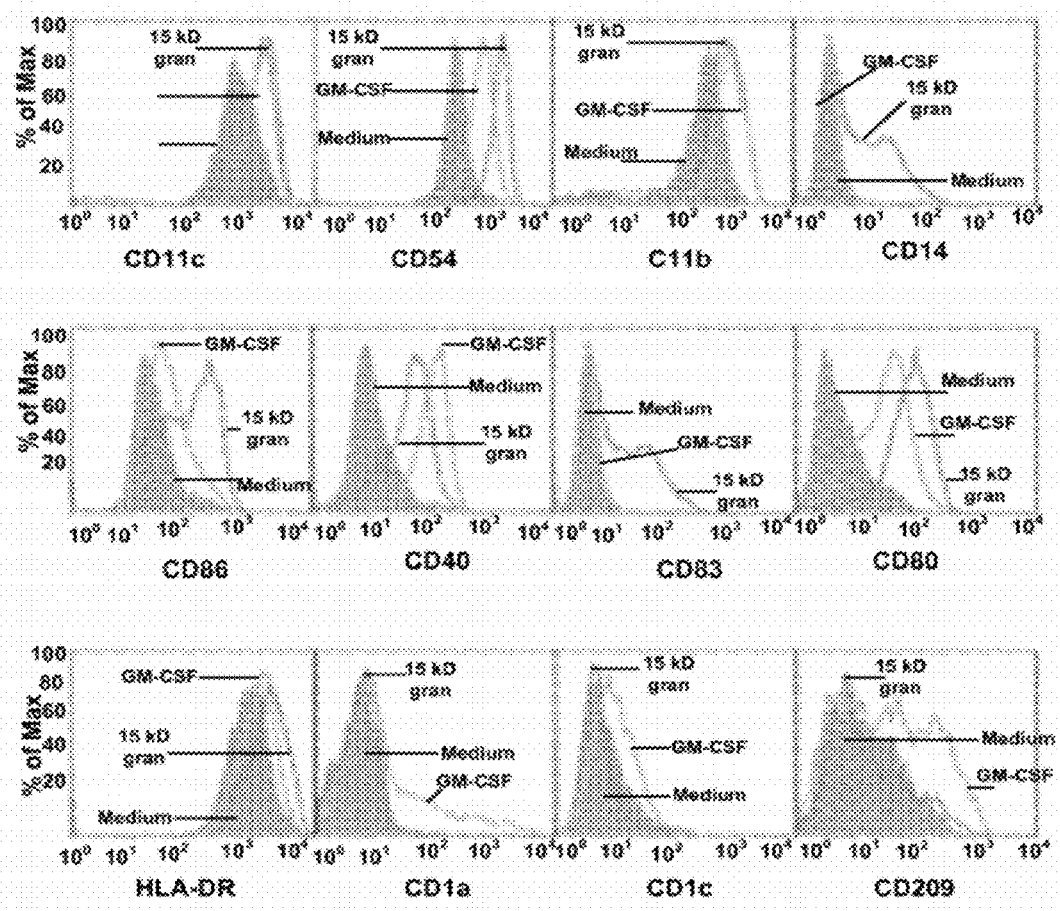

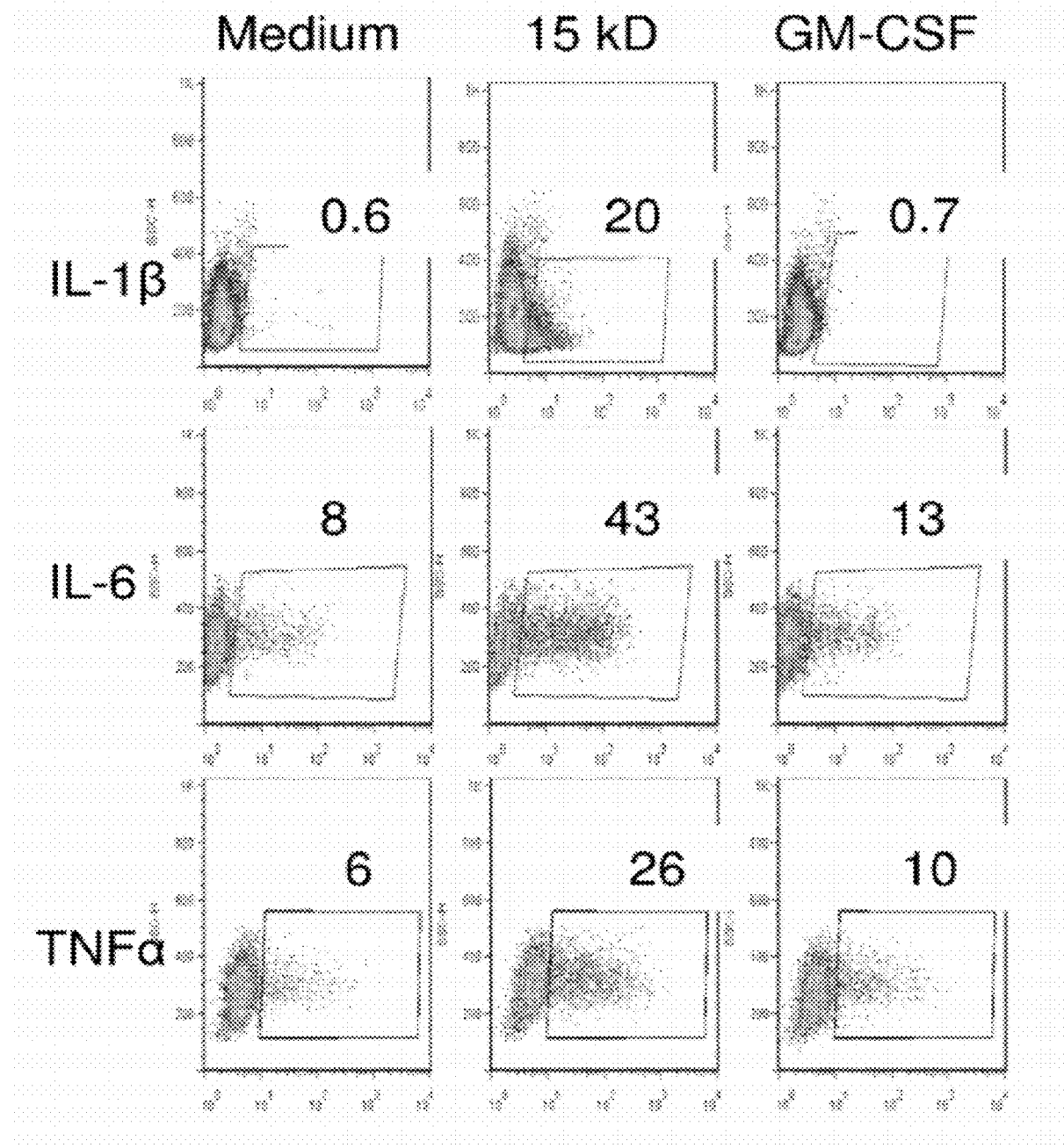

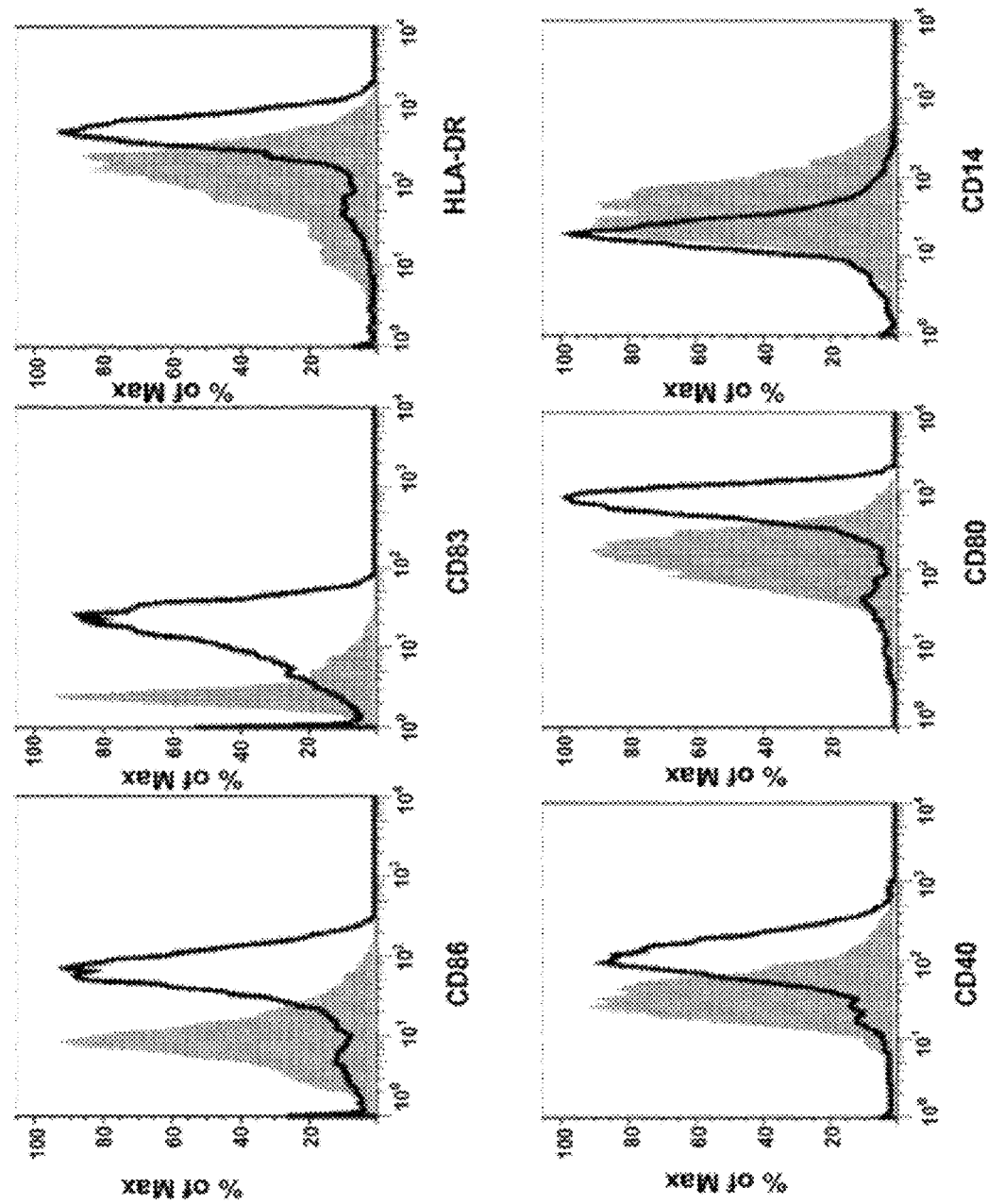

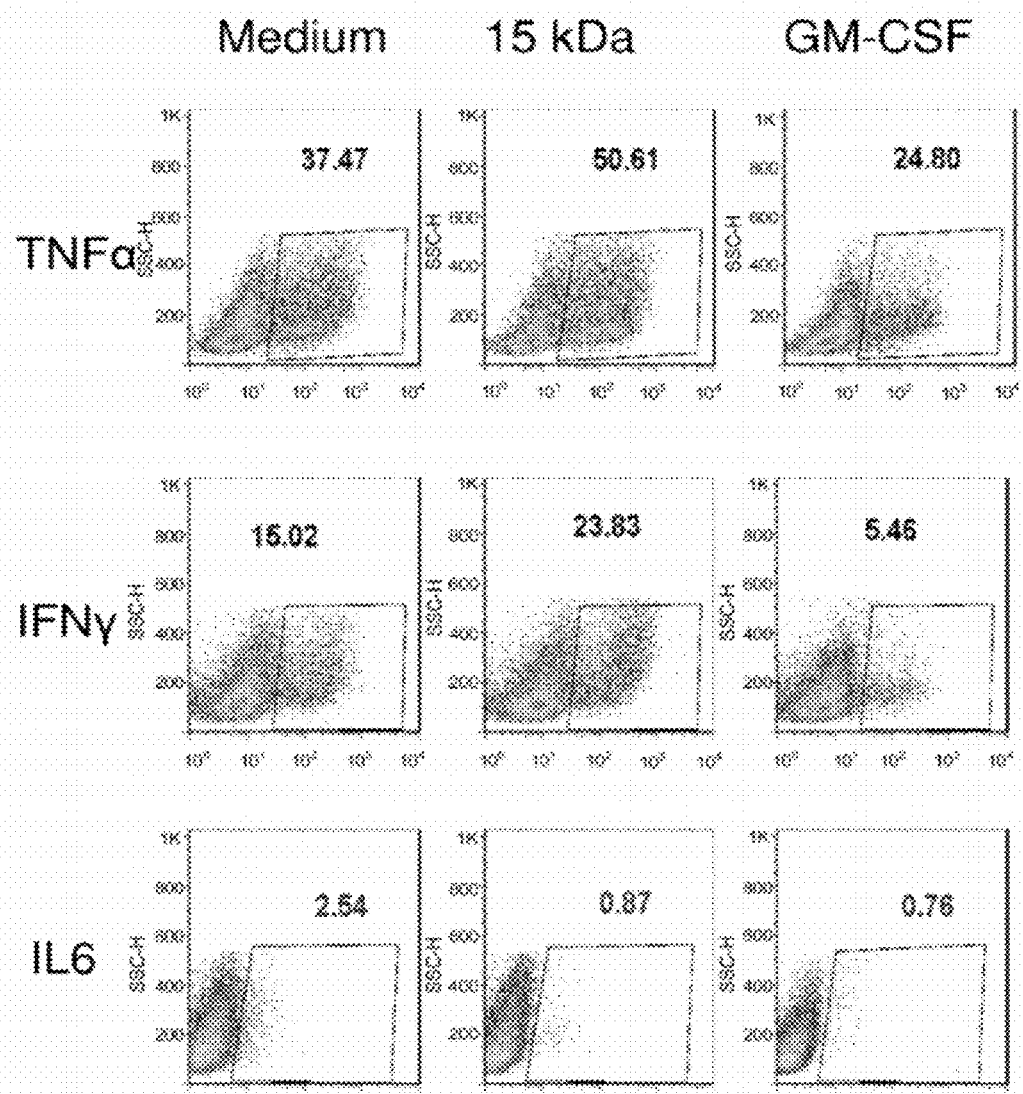

GRANULYSIN IN IMMUNOTHERAPY

CROSS REFERENCE TO RELATED APPLICATION

This is the §371 U.S. National Stage of International Application No. PCT/US2010/052036, filed Oct. 8, 2010, which was published in English under PCT Article 21(2), which in turn claims the benefit of U.S. Provisional Application No. 61/250,601, filed Oct. 12, 2009, which is incorporated by reference herein in its entirety.

FIELD

This disclosure relates to methods for the treatment of immune-based disorders, such as autoimmune diseases, organ transplantation rejection and tumor immunotherapy. The disclosure also relates to the stimulation of an immune response in a host upon administration of a therapeutically effective amount of 15 kD granulysin.

BACKGROUND

Vaccination protocols have improved over the last several decades; however a therapeutically effective immune response has still been difficult to generate for some conditions. For example, human tumor immunotherapy has met with only limited success. Among the reasons for this difficulty have been the limited availability of tumor associated antigens, and an inability to deliver antigens in a manner that renders them immunogenic.

Dendritic cells (DC) include a heterogeneous family of antigen presenting cells (APC) that present antigens for the modulation of an immune response or induce immunological tolerance. The number of dendritic cells in the blood is surprisingly few, less than about 1% of blood mononuclear leukocytes. Thus, the low number of circulating dendritic cells makes their therapeutic use for the stimulation or modulation of an immune response difficult. Dendritic precursor cells, such as monocytes, migrate from a host's bone marrow to specific sites where they become activated and differentiate into dendritic cells. Following exposure to an antigen and an activation signal, the dendritic cells secrete chemokines and cytokines, and then present the processed antigen to naive T cells to produce an immune response in the host.

Bidirectional interactions between antigen presenting dendritic cells and naïve T cells initiate either an immunogenic or a tolerance pathway that are of particular importance in autoimmune disease and in transplantation medicine. Conventional subsets of dendritic cells described in humans include myeloid dendritic cells (mDC) and plasmacytoid dendritic cells (pDC).

Dendritic cells possess a distinct morphology and are characterized by the expression of large amounts of class II MHC antigens, and the absence of lineage markers, including CD14 (monocyte), CD3 (T cell), CD19, CD20, CD24 (B cells), CD56 (natural killer), and CD66b (granulocyte) (Shortman and Liu, *Nat. Rev. Immunol.* 2:151-161, 2002). Dendritic cells also express a variety of adhesion and co-stimulatory molecules such as CD80 and CD86, and molecules that regulate co-stimulation, such as CD40. The phenotype of dendritic cells varies with the stage of dendritic cell maturation and activation (Chapuis et al., *Eur. J. Immunol.* 27:431-441, 1997). However, expression of adhesion molecules, MHC antigens and co-stimulatory molecules increases with dendritic cell maturation. Antibodies that preferentially stain dendritic cells are commercially available, such as anti-CD83 and anti-CD80. Accordingly, the expression level of a particular antigen marker can be used to confirm if the antigen presenting cell is a dendritic cell, and if the dendritic cell is mature (Zhou and Tedder, *J. Immunol.* 154:3821-3835, 1995; Weissman et al., *J. Immunol.* 155:4111-4117, 1995).

Several in vitro methods have been developed to expand populations of dendritic cells and to augment anti-cancer immunity. Ex vivo exposure of expanded populations of dendritic cells to antigens found on tumor cells or other disease-causing cells, followed by reintroduction of the antigen-loaded dendritic cells to the subject, significantly enhanced presentation of the antigen to responding T cells. For example, culturing blood mononuclear leukocytes for eight days in the presence of granulocyte-monocyte colony stimulating factor (GM-CSF) and interleukin-4 (IL-4) was found to produce large numbers of dendritic cells (Sallusto and Lanzavecchia, *J. Exp. Med.* 179:1109-1118, 1994).

DNA vaccines that incorporate plasmids encoding cytokines (such as GM-CSF and IL-4) have been used to investigate dendritic cell maturation pathways. In particular, GM-CSF cDNA has been used as a DNA vaccine adjuvant for glycoprotein B of *Pseudorabies* virus (PrV) in a murine mouse model (Yoon et al, *Microbiol. Immunol.* 50:83-92, 2006). At least nine cytokine-secreting vectors have been identified as genetic adjuvants for DNA vaccines (in "DNA Vaccines Methods and Protocols," edited by Douglas Lowrie and Robert Whalen).

Nucleic acid immunization is a relatively recent approach in vaccine development. The ability of DNA vaccines to protect against challenges from pathogens has been demonstrated in animal models of influenza, malaria, mycobacterium, HIV, and Ebola. A DNA-based vaccine usually comprises purified plasmid DNA carrying sequences encoding a target antigen under the control of a eukaryotic promoter. The plasmid is injected into the muscle or skin and the host cells take up the plasmid and express the antigen intracellularly. Expression of the encoded antigen by the host's cells is one of the advantages of this approach because it mimics natural infection. To enhance immune responses induced by DNA vaccines, co-administration of adjuvants such as cytokines, chemokines and co-stimulatory molecules have been used. It is therefore believed that administering plasmids encoding cytokines (such as GM-CSF or IL-4) and a target antigen may cause intracellular expression of both the antigen and the cytokine in the host, thereby providing an enhanced immune response in the host.

Cancers are a significant public health problem. Many cancer treatments are available to such patients, including surgical excision, chemotherapy, radiotherapy, and bone marrow transplantation. While many conventional cancer therapies are often effective in reducing neoplastic growth, healthy cells are frequently compromised by cytotoxic treatments. Non-selective cell damage causes pain, inflammation, hair loss, immunosuppression and gastrointestinal damage. Improved compositions and methods are needed to treat, inhibit, or alleviate the development of tumors. For example, tumor antigens have been administered to a tumor bearing host in attempts to produce an immune response to the tumor cells in the host. This approach has met with varying and modest results.

Granulysin is a naturally occurring protein expressed in human cytotoxic T lymphocytes (CTL) and natural killer (NK) cells. Granulysin expressed in its full-length form has a molecular weight of approximately 15,000 Daltons and is known as 15 kD or 15 kDa granulysin. A post-translational modified form of 15 kD granulysin in which both the N- and C-termini are cleaved is known as 9 kD granulysin. The 9 kD granulysin peptide has been extensively studied and is observed to possess anti-microbial and tumorcidal activity (Hanson et al., *Mol. Immunol.* 36:413-422, 1999; Krensky, *Biocehm. Pharmacol.* 59:317-320, 2000; Clayberger et al., *Curr. Opin. Immunol.* 15:560-565, 2003; Deng et al., *J. Immunol.* 174:5243-5248, 2005; Stenger et al., *Science* 282: 121-125, 1998; and Huang et al., *J. Immunol.* 178:77-84, 2007). The 9 kD granulysin peptide is also known to have cytolytic properties and its resulting toxicity may limit its therapeutic use.

SUMMARY

The present disclosure provides a method for stimulating an immune response, or enhancing the efficacy of a vaccine, without simultaneously initiating a cytolytic response in a host. Several publications disclose that 9 kD granulysin is a cytolytic and antimicrobial compound. However, until recently, the properties of the full-length 15 kD granulysin protein were unknown. One reason for the lack of research was because an animal model did not exist (mice do not express granulysin). In addition, others reported substantial technical issues when trying to constitutively express the full-length 15 kD protein in vitro.

Chen et al. (U.S. Patent Publication No. 2008/0050382 A1) identified 15 kD granulysin in blister fluids from skin lesions of Stevens-Johnson Syndrome (SJS) and Toxic Epidermal Necrolysis (TEN) patients. In vivo injection of the blister fluid into epidermis of nude mice induced massive skin cell death, mimicking the human pathology of SJS/TEN. Chen et al. concluded that 15 kD granulysin mediated this undesired immune response in the host. In contrast to the study by Chen et al., the inventors have determined that recombinant full-length 15 kD granulysin is not cytolytic and surprisingly exhibits substantially more immune-stimulating activity than 9 kD granulysin.

The inventors have also determined that 15 kD granulysin activates monocytes to differentiate into monocyte derived-dendritic cells (MO-DC), thereby initiating an immune response in a subject that can produce allospecific T cells, and can therefore be used as a vaccine adjuvant, alone or in combination with other vaccine preparations or therapeutic agents.

A method has also been developed to produce 15 kD granulysin in vitro using a recombinant vector encoding full-length 15 kD granulysin. In addition, methods are disclosed for using 15 kD granulysin to activate desired immune responses, in vaccination, infection, or other immunotherapies. Additionally, methods are disclosed for using the 15 kD granulysin to block induction of an immune response in autoimmune diseases or organ transplantation.

The disclosure also relates to using 15 kD granulysin to induce the differentiation of monocytes into monocyte-derived dendritic cells. In several embodiments, the methods are used to identify monocyte-derived dendritic cells from other cells of the immune system, such as macrophages. In a further embodiment, the methods are used to initiate or stimulate an immune response in a host following administration of 15 kD granulysin to treat, lessen or inhibit an immune-based disorder. Alternatively, the method can be used for in vitro differentiation of monocytes into dendritic cells and/or production of allospecific T cells. The methods are also effective for inhibiting an undesired immune response in an immunocompromised host, for example someone who has or is a candidate for undergoing solid organ transplantation, such as a dialysis patient.

In some embodiments, 15 kD granulysin can inhibit the development of a tumor in a host, for example to treat or inhibit the tumor. In another aspect, 15 kD granulysin is effective for the treatment of a non-infectious disease or disorder. In another embodiment, 15 kD granulysin may be used as a vaccine adjuvant, for example as an anti-tumor vaccine adjuvant, e.g., an adjuvant in a Hepatitis B virus (HBV) or Hepatitis C virus (HCV) prophylactic vaccine. In another embodiment, 15 kD granulysin can be used as an adjuvant for an allergen-based vaccine.

In one aspect, the immunogenicity of an antigen may be enhanced by increasing the specific antigen presenting function of dendritic cells in a mammalian host. Prior to immunization with an antigen, the host is treated with 15 kD granulysin. This activates and expands the number of monocytes in the host and causes the monocytes to differentiate into monocyte-derived dendritic cells. In some instances, the host may be given a local, e.g., subcutaneous, intramuscular, etc., injection of antigen in combination with 15 kD granulysin, such as the administration of an immunostimulatory sequence, for example a CpG motif containing oligonucleotide, interleukin-1 (IL-1), lipopolysaccharide (LPS), or an additional toll-like receptor (TLR) agonist. In other examples, the antigen may be administered to a subject as a fusion protein with 15 kD granulysin. The disclosed methods promote the recruitment and maturation of monocytes into monocyte-derived dendritic cells while concurrently inducing antigen-specific migration from the blood vessels to tissues and subsequently the migration of monocyte-derived dendritic cells to lymphoid organs. The monocyte-derived dendritic cells can then interact with and present processed antigens to local T cells that in turn initiate an immune response to the presented antigen.

The methods of the invention are particularly useful in subjects with a sub-optimal immune response, for example in conditions of chronic infection, a lack of immune response to tumor antigens, anergic or immunosuppressed individuals, or a low responsiveness to allergens.

In one aspect, the disclosed methods are used to enhance the host's immune response to tumor cells present in the host's body.

In another embodiment, 15 kD granulysin is used to delay development of a tumor in a subject, induce tolerance to a transplanted organ in a mammalian transplant recipient, or inhibit an immune-based disorder in a subject, such as an autoimmune disorder. A therapeutically effective amount of 15 kD granulysin can be administered to a subject having one or more of these conditions.

In yet another embodiment, a method of generating an activated T lymphocyte is provided, wherein a monocyte-derived dendritic cell is produced following incubation with 15 kD granulysin, and the monocyte-derived dendritic cell is contacted with a T lymphocyte in vitro, thereby producing an activated T lymphocyte. In other examples, a monocyte-derived dendritic cell is produced following incubation with a fusion protein of 15 kD granulysin and a target antigen.

The foregoing and other features of the disclosure will become apparent from the following detailed description, which proceeds with reference to the accompanying figures.

BRIEF DESCRIPTION OF THE DRAWINGS

FIG. 1A data were obtained using human monocytes in cell culture medium in the absence of granulysin. FIG. 1B and FIG. 1C show flow cytometry data obtained from human monocytes incubated for 2 days with 9 kD granulysin or 15 kD granulysin, respectively (10 nM). FIG. 1C (15 kD granulysin treatment) shows an increase in both cell granularity and cell size in comparison to either 9 kD granulysin treatment or incubation in cell culture medium. Cell size is shown on the x-axis; cell granularity is shown on the y-axis.

FIG. 4A shows cell surface expression of marker, CD11a, on the surface of monocytes incubated in the presence of cell culture medium only, GM-CSF (10 ng/ml), or in the presence of 15 kD granulysin (10 nM). Cells were harvested after five days, stained with APC-conjugated anti-human CD1a and analyzed by FACS. FIG. 4B shows the cell surface expression of CD1a on the surface of monocytes incubated under identical conditions as described in FIG. 4, except that the monocytes were incubated for the duration of the experiment with 10 ng/ml interleukin-4 (IL-4). FIG. 4A and FIG. 4B demonstrate that GM-CSF but not 15 kD granulysin induces expression of CD1a on the cell surface of monocytes.

FIG. 5A shows significant fold-increase of TNFα expression when monocytes were incubated in the presence of 15 kD granulysin or in the presence of 15 kD granulysin and pertussis toxin (100 ng/ml). mRNA was obtained from the cultured monocytes and converted to cDNA. Quantitative PCR allowed for the calculation of fold-increase in expression relative to a house-keeping gene. FIGS. 5B and 5C show results of similar experiments for the fold-increase in cytokine expression of IL-1β and IL-6, respectively.

FIG. 6 is a graph showing fold-stimulation of allospecific T cells upon incubation of human CD14+ monocytes with 15 kD granulysin or GM-CSF. The four upper rows of FIG. 6, monocytes were activated by incubation with GM-CSF (10 ng/ml) or GM-CSF and IL-4 (10 ng/ml). After 4 days, lipopolysachharide (LPS) was added to the culture to induce dendritic cell maturation. Cells were harvested on day 6 and used to stimulate allogeneic T cells. After five additional days, cellular proliferation was measured and reported as fold-stimulation above T-cells alone. The four lower rows of FIG. 6 demonstrate fold-stimulation of allospecific T cells upon incubation of human CD14+ monocytes with 15 kD granulysin (10 nM) or 15 kD granulysin and IL-4 (10 ng/ml). Identical to the upper rows of FIG. 6, LPS was added to the cells at day 4 to induce dendritic cell maturation. The cells were harvested on day 6 and used to stimulate allogeneic T cells. After five additional days, cellular proliferation was measured and expressed as fold-stimulation above T-cells alone.

FIG. 8 is a series of panels showing activation of human monocytes by 15 kD granulysin. FIG. 8B is a series of graphs showing expression of cell surface molecules by monocytes cultured with medium, 15 kD granulysin (10 nM), or GM-CSF (10 ng/ml) for 24 hours, then stained with fluorescent antibodies and analyzed by flow cytometry. FIG. 8C is a series of plots showing expression of IL-1β, IL-6, and TNFα in monocytes cultured with medium, 15 kD granulysin (10 nM), or GM-CSF (10 ng/ml) for 24 hours, then stained with fluorescent antibodies and analyzed by flow cytometry.

FIG. 9 is a series of graphs showing effect of 15 kD granulysin on maturation of dendritic cells and activation of cytokine expression in T cells. FIG. 9A is a series of graphs showing that 15 kD granulysin induces differentiation of immature dendritic cells to mature dendritic cells. Monocytes were cultured for 4 days with 10 ng/ml GM-CSF plus 10 ng/ml IL-4, and then for another 24 hours with medium (gray) or 10 nM 15 kD granulysin (black line). Cells were stained with fluorescent antibodies and analyzed by flow cytometry. FIG. 9B is a series of graphs showing activation of cytokine expression in T cells cultured with dendritic cells induced with 15 kD granulysin. Purified T cells were added to allogeneic monocytes that had been cultured for 4 days with medium, 10 nM 15 kD granulysin, or 10 ng/ml GM-CSF. After a 5 day culture, cytokine production was measured by intracellular staining and flow cytometry.

FIG. 10 is a series of graphs showing the effect of granulysin expression in mice challenged with CT26 tumor cells. Wild type or granulysin transgenic mice ($GNLY^{+/-}$) were injected with CT26 tumor cells in the left flank, and tumor and draining lymph nodes were removed after 12-14 days. FIG.

10A shows the weight of excised tumors. Each point represents one animal; each panel represents one experiment. $*p<0.01$

SEQUENCE LISTING

Any nucleic acid and amino acid sequences listed herein or in the accompanying sequence listing are shown using standard letter abbreviations for nucleotide bases, and three letter code for amino acids, as defined in 37 C.F.R. 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Apr. 11, 2012, and is 2930 bytes, which is incorporated by reference herein.

SEQ ID NO: 1 is an exemplary 15 kD granulysin amino acid sequence.

SEQ ID NO: 2 is an exemplary 15 kD granulysin nucleic acid sequence.

DETAILED DESCRIPTION

The inventors have discovered that 9 and 15 kD granulysin have very different activities. For example, 9 kD granulysin is cytotoxic while 15 kD granulysin is not. Recombinant 9 kD granulysin lyses a wide variety of tumor cells as well as pathogens, including gram positive and gram negative bacteria, fungi, parasites and intracellular organisms such as *M. tuberculosis*. In contrast, 15 kD granulysin does not kill any cells (eukaryotic or prokaryotic).

Figure 8A:
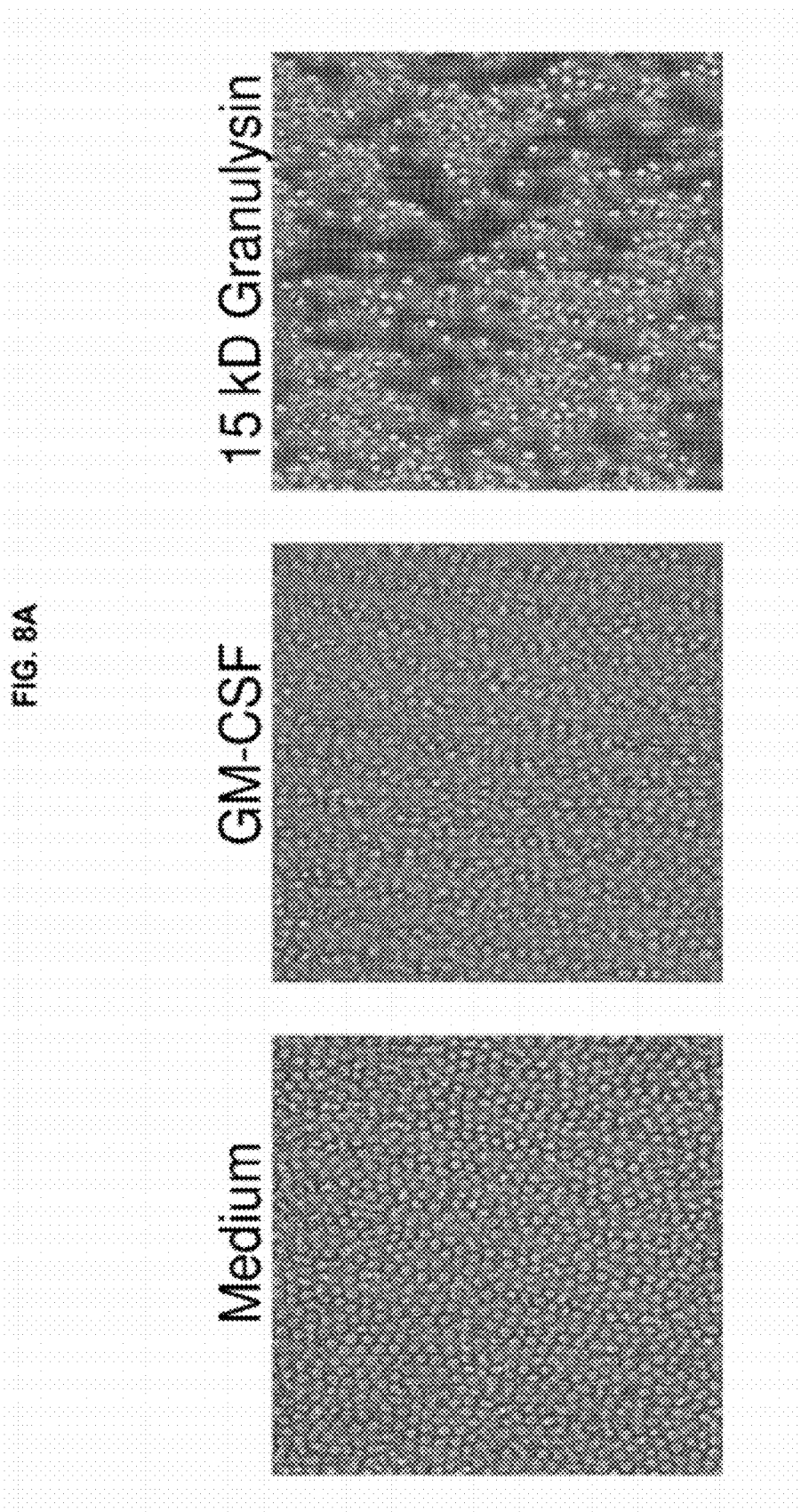
FIG. 8A is a series of digital images showing purified $CD14^+$ monocytes cultured in medium alone (left), medium plus 10 ng/ml GM-CSF (middle), or medium supplemented with 10 nM 15 kD granulysin (right) for 6 hours. Images taken with a 10× objective.

The 15 kD but not 9 kD granulysin activates monocytes (FIGS. 1A-1C and FIGS. 2A-2D). Moreover, 15 kD but not 9 kD granulysin activates monocytes to become immature dendritic cells (FIGS. 3A-3F), and can activate immature dendritic cells that had been activated by the conventional method (GM-CSF plus IL-4) to become mature dendritic cells (FIG. 3G). The 15 kD granulysin, but not GM-CSF, induces rapid phenotypic changes in monocytes (FIG. 8A).

Recombinant 15 kD granulysin or GM-CSF induces monocytes to express CD1c, CD11a, CD29, CD40, CD54, CD80, CD86 and HLA-DR (see FIG. 3G). GM-CSF, but not 15 kD granulysin, induces expression of CD1a on monocytes.

The 15 kD granulysin induces monocytes to express IL-1α, IL-13, IL-6, IL-12, IL-23 and TNF-α, but does not induce expression of IL-10, IL-18, or IL-27. In addition, 15 kD granulysin causes a rapid gene expression in monocytes, peaking at about 4 hours, but GM-CF induced gene expression is not evident until about 24 hours.

Figure 7:
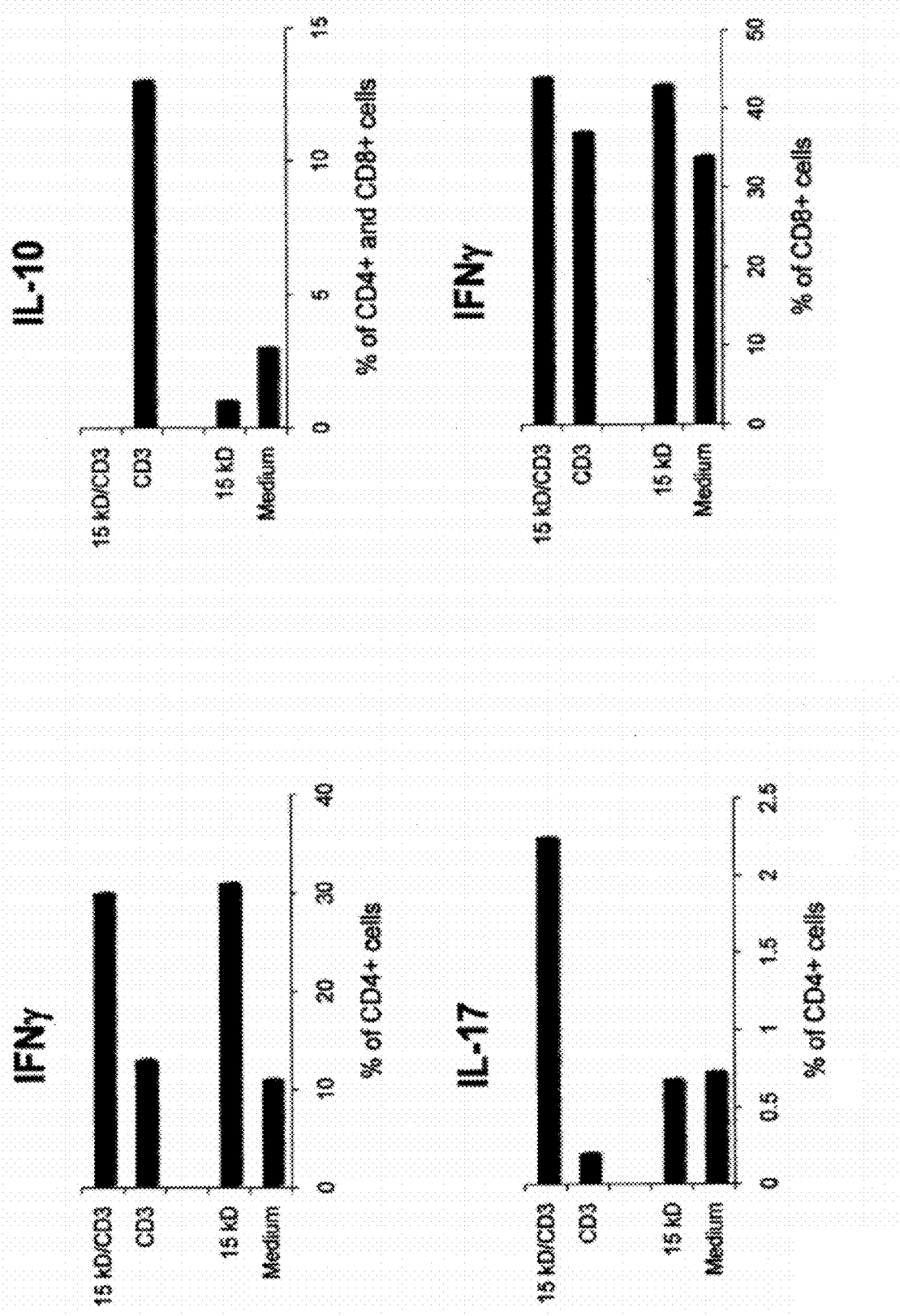
FIG. 7 is a series of graphs that show 15 kD granulysin induces Th1 and Th17 cell expansion, but inhibits Th2 cells. Peripheral blood mononuclear cells ($2\times10^6$/ml) were incubated in RPMI-1640 supplemented with 10% FCS. Where indicated, anti-CD3 antibody was added at 0.001 m/ml and 15 kD granulysin was added at 10 nM. After 7 days, cells were restimulated with PMA (5 ng/ml) and ionomycin (500 ng/ml) for 1 hour at which time Golgistop was added and the incubation continued for another 4 hours. Cells were harvested and stained for surface CD4 or CD8. Cells were then fixed, permeabilized, and stained with fluorescent antibodies specific for IFNγ, IL-17 or IL-10 and analyzed by FACS.

Monocytes activated by 15 kD granulysin or GM-CSF activate allospecific T cells (FIG. 6), but 9 kD granulysin does not exhibit this activity. Incubation of monocytes with 15 kD granulysin causes rapid phenotypic changes and a concomitant increase in expression of a panel of proinflammatory cytokines. Lastly, addition of 15 kD granulysin to unseparated peripheral blood mononuclear cells induces both Th1 and Th17 responses, but inhibits Th2 responses (FIG. 7). Thus, 15 kD granulysin is a potent (effective in the picomolar to nanomolar range) and novel activator of the proinflammatory immune response that is believed to be useful as a novel adjuvant for vaccines. These results also enable an in vitro method of stimulating production of an allospecific T lymphocyte.

I. Abbreviations

APC: antigen presenting cell
CA IV: carbonic anhydrase isozyme IV
DC: dendritic cell
FACS: fluorescent activated cell sorting
Flt-3L: flt-3 ligand
GM-CSF: granulocyte macrophage colony stimulating factor
G-CSF: granulocyte colony stimulating factor
HGF: hepatocyte growth factor
IFN-α: interferon alpha
IFN-γ: interferon gamma
IL: interleukin
kD: kilodalton
LPS: lipopolysaccharide
M-CSF: macrophage colony stimulating factor
mDC: myeloid dendritic cell
MO: monocyte
MO-DC: monocyte-derived dendritic cell
pDC: plasmacytoid dendritic cell
TIL: tumor-infiltrating lymphocytes
TLR: toll-like receptors
TSLP: thymic stromal lymphopoietin
VIP: vasoactive intestinal peptide II. Explanation of Terms It is to be understood that the present disclosure is not limited to the particular methodology, protocols, cell lines, animal species or genera, constructs and reagents described, as such may vary. It is also understood that the terminology used herein is for the purpose of describing particular embodiments only, and is not intended to limit the scope of the present disclosure.

As used herein the singular forms "a," "and," and "the" refer to both the singular as well plural, unless the context clearly indicates otherwise. For example, reference to "an immunization" includes a plurality of such immunizations and reference to "the cell" includes reference to one or more cells and equivalents thereof known to one of ordinary skill in the art, and so forth. As used herein the term "comprises" means "includes." Thus, "a composition comprising 15 kD granulysin" means "including 15 kD granulysin" without excluding other additional components.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanation of terms, will control.

All publications and patent applications cited in this specification are herein incorporated by reference as if each individual publication or patent application were specifically and individually indicated to be incorporated by reference.

All of the technical and scientific terms used herein have the same meaning as commonly understood to one of ordinary skill in the art to which this invention belongs unless clearly indicated otherwise.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Activation Agent: refers to a compound, such as a naturally occurring protein, which acts on monocytes to expand (e.g., proliferate) and differentiate into monocyte-derived dendritic cells (MO-DC). In a preferred embodiment, the activating agent is 15 kD granulysin. The dose of the activating agent will be effective to substantially increase the number of monocytes. The increase in the number of monocytes after activation can be quite high, usually by at least 2-fold more, typically 5-fold more, and may be as high as about 20- to about 75-fold more. Monocytes activated by 15 kD granulysin can differentiate into monocyte-derived dendritic cells and will therefore typically express increased levels of CD40, CD80, and CD83 as compared to non-activated monocytes. Additionally, monocytes activated through the administration of 15 kD granulysin and thus differentiated into monocyte-derived dendritic cells will express reduced levels of lineage markers such as CD14, as compared to untreated monocytes, and can be identified on the basis of these criteria, among others.

Allergen/Allergy: is a disorder of the immune system also referred to as atopy. Allergic reactions occur to normally harmless environmental substances known as allergens e.g., dust mite dander. Common allergic reactions include eczema, hives, hay fever, asthma, and food and drug allergies. In some instances, a subject's immune response to an allergen is severe enough to induce anaphylactic shock.

Animal: Living multi-cellular vertebrate organisms, a category that includes, for example, mammals and birds. The term mammal includes both human and non-human mammals. Similarly, the term "subject" includes both human and veterinary subjects.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. Examples of exemplary antigens of interest include proteins, polypeptides, polysaccharides, a DNA molecule, a RNA molecule, a whole cell lysate, an apoptotic cell, or a combination thereof.

An "antigenic polypeptide" is a polypeptide to which an immune response, such as a T cell response or an antibody response, can be stimulated. "Epitope" or "antigenic determinant" refers to a site on an antigen to which B and/or T cells respond. T cells can respond to the epitope when the epitope is presented in conjunction with an MHC molecule. Epitopes can be formed both from contiguous amino acids (linear) or noncontiguous amino acids juxtaposed by tertiary folding of an antigenic polypeptide (conformational). Epitopes formed from contiguous amino acids are typically retained on exposure to denaturing solvents whereas epitopes formed by tertiary folding are typically lost on treatment with denaturing solvents. Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 5 and 15 amino acids, such as, 9, 10, 12 or 15 amino acids. The amino acids are in a unique spatial conformation. In one particular example, the antigen is an antigen obtained from a subject who is a donor, such as of an organ or of bone marrow, to another genetically different individual. In another example, the antigen is a tumor antigen.

A "target antigen" includes, but is not limited to, an antigen that is present in a disease or disorder, such as a tumor antigen, an autoimmune antigen, an allergen antigen, or an antigen expressed in solid organ transplantation rejection. A target antigen may be any antigen for which it is desirable to modulate an immune response in a subject. In particular embodiments, the disclosed methods enhance or stimulate an immune response in a subject against a target antigen (for example, a tumor antigen). In other embodiments, the disclosed methods inhibit or decrease an immune response in a subject against a target antigen (for example, an autoimmune antigen, an allergen, or an antigen expressed in solid organ transplantation rejection).

Autoimmune disorder: A disorder or disease in which the immune system produces an immune response (e.g. a B cell or a T cell response) against an endogenous antigen, with consequent injury to tissues. The injury may be localized to certain organs, such as thyroiditis, or may involve a particular tissue at different locations, such as Goodpasture's disease, or may be systemic, such as lupus erythematosus.

Cancer: A malignant neoplasm that has undergone characteristic anaplasia with loss of differentiation, increased rate of growth, invasion of surrounding tissue, and is capable of metastasis. For example, thyroid cancer is a malignant neoplasm that arises in or from thyroid tissue, and breast cancer is a malignant neoplasm that arises in or from breast tissue (such as a ductal carcinoma). Residual cancer is cancer that remains in a subject after any form of treatment given to the subject to reduce or eradicate the cancer. Metastatic cancer is a cancer at one or more sites in the body other than the site of origin of the original (primary) cancer from which the metastatic cancer is derived.

Chemokine (chemoattractant cytokine): A type of cytokine (a soluble molecule that a cell produces to control reactions between other cells) that specifically alters the behavior of leukocytes (white blood cells). Examples include, but are not limited to, interleukin 8 (IL-8), platelet factor 4, melanoma growth stimulatory protein, and the like.

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

Contacting: Placement in direct physical association, including both a solid and liquid form. Contacting can occur in vitro with isolated cells or in vivo by administering to a subject.

Cytokine: Proteins made by cells that affect the behavior of other cells, such as lymphocytes. In one embodiment, a cytokine is a chemokine, a molecule that affects cellular trafficking. The term "cytokine" is used as a generic name for a diverse group of soluble proteins and peptides that act as humoral regulators at nanomolar to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor α (TNFα), interleukin-6 (IL-6), interleukin-10 (IL-10), interleukin-12 (IL-12), macrophage inflammatory protein 2 (MIP-2), keratinocyte derived cytokine (KC), and interferon-α (INF-γ)

Decrease: Becoming less or smaller, as in number, amount, size, or intensity. In one example, decreasing the risk of a disease (such as for tumor formation) includes a decrease in the likelihood of developing the disease by at least about 20%, for example by at least about 30%, 40%, 50%, 60%, 70%, 80%, or 90%. In another example, decreasing the risk of a disease includes a delay in the development of the disease, for example a delay of at least about six months, such as about one year, such as about two years, about five years, or about ten years.

In one example, decreasing the signs and symptoms of a tumor includes decreasing the size, volume, tumor burden or number of tumors (such as skin tumors) or metastases by a desired amount, for example by at least about 5%, 10%, 15%, 20%, 25%, 30%, 50%, 75%, or even at least about 90%, as compared to a response in the absence of the therapeutic composition.

Dendritic cells (DC): Dendritic cells are antigen presenting cells (APC) involved in immune responses. Dendritic cells include plasmacytoid dendritic cells and myeloid dendritic cells. Their major function is to obtain antigen in tissues, migrate to lymphoid organs and present the antigen in order to activate local T cells, which in turn generate an immune response. Immature dendritic cells originate in the bone marrow and reside in the periphery as immature cells. In one embodiment, a dendritic cell is a plasmacytoid dendritic cell. Plasmacytoid dendritic cells differentiate from precursors called "DC2" while myeloid dendritic cells differentiate from precursors termed "DC1."

Dendritic cells are capable of evolving from immature, antigen-capturing cells to mature, antigen-presenting T cells; converting antigens into immunogens and expressing molecules such as cytokines, chemokines, co-stimulatory molecules and proteases to initiate an immune response.

Dendritic cells are derived from hematopoietic stem cells in the bone marrow and are widely distributed as immature cells within all tissues, particularly those that interface with the environment (e.g. skin, mucosal surfaces, etc.) and in lymphoid organs Immature dendritic cells are recruited to sites of inflammation in peripheral tissues following pathogen or foreign-body invasion "Immature" dendritic cells may express the chemokine receptors CCR1, CCR2, CCR5, CCR6 and CXCR1. Immature dendritic cells capture antigens by phagocytosis, macropinocytosis or via interaction with a variety of cell surface receptors and endocytosis. Internalization of foreign antigens can subsequently trigger their maturation and migration from peripheral tissues to lymphoid organs (see below).

The ability of dendritic cells to regulate immunity is dependent on dendritic cell differentiation, as it depends on their maturation state. A variety of factors can induce differentiation following antigen uptake and processing within dendritic cells, including: whole bacteria or bacterial-derived antigens (e.g. lipopolysaccharide), inflammatory cytokines, ligation of select cell surface receptors (e.g. CD40) and viral products (e.g. double-stranded RNA). During their conversion from immature to mature cells, dendritic cells undergo a number of phenotype and functional changes. The process of dendritic cell maturation, in general, involves a redistribution of major histocompatibility complex (MHC) molecules from intracellular endocytic compartments to the dendritic cell surface, down-regulation of antigen internalization, an increase in the surface expression of co-stimulatory molecules, morphological changes (e.g. formation of dendrites), cytoskeleton re-organization, secretion of chemokines, cytokines and proteases, and surface expression of adhesion molecules and chemokine receptors. Dendritic cells are characterized by their distinctive morphology and high levels of surface MHC-class II expression, such as CD40 and CD80 markers.

Dendritic Cell Precursor: Immature cells that can differentiate into dendritic cells. In one embodiment a dendritic cell precursor is a DC1 cell that differentiates into myeloid cells (e.g. a monocyte).

Differentiation: The process by which cells become more specialized to perform biological functions, and differentiation is a property that is totally or partially lost by cells that have undergone malignant transformation. For example, dendritic cell precursors such as monocytes differentiate into dendritic cells under the influence of certain cytokines and growth factors.

Epitope: An antigenic determinant. These are particular chemical groups or peptide sequences on a molecule that are antigenic, e.g., that elicit a specific immune response. An antibody binds a particular antigenic epitope.

Expansion and Activation: Refers to the length of time required for activation and expansion of monocytes into monocyte derived-dendritic cells. The time taken is usually at least about 2 days, more usually about 1 week, and may take about 10 days to about 2 weeks for optimal expansion. The length of time allotted for activation and expansion can be predicted based on previous trials with the activation agent at a similar dose, or may be monitored individually by quantitating the change in the number of dendritic cells present in the peripheral blood of a subject.

Flt-3 ligand (flt-3L): A factor that binds to the flt-3 receptor. The flt-3 ligand promotes long-term expansion and differentiation of human pro-B-cells in the presence of IL-7, or IL-7 and IL-3. The flt-3 ligand is known to support the survival of precursor cell types in the lineage of blood-forming cells, such as highly proliferative potential colony forming cells (e.g. see Lyman et al., *Cell* 75:1157-67, 1993).

Granulocyte/macrophage colony-stimulating factor (GM-CSF): A factor which modulates the maturation and function of dendritic cells, (Witmer-Pack et al., *J. Exp. Med.* 166:1484-98, 1987).

GM-CSF is a monomeric protein of 127 amino acids with two glycosylation sites. The protein is synthesized as a precursor of 144 amino acids, which included a hydrophobic secretory signal sequence at the amino-terminal end. The human gene has a length of approximately 2.5 kilobase (kb) and contains four exons. The distance between the GM-CSF gene and the IL-3 gene is approximately 9 kb. The human GM-CSF gene maps to chromosome 5q22-31.

GM-CSF was isolated initially as a factor stimulating the growth of macrophage/granulocyte-containing colonies in soft agar cultures. GM-CSF is also involved in the growth and development of granulocyte and macrophage progenitor cells. GM-CSF stimulates myeloblasts and monoblasts and triggers irreversible differentiation of these cells. GM-CSF synergizes with erythropoietin in the proliferation of erythroid and megakaryocytic progenitor cells.

GM-CSF has been used clinically for the physiological reconstitution of hematopoiesis in diseases characterized either by an aberrant maturation of blood cells or by a reduced production of leukocytes. The usual dose, route and schedules for GM-CSF are 5-10 µg/kg/day either by 4-6 hours intravenous infusion or by subcutaneous injection.

Granulysin: Granulysin is expressed from a gene located on human chromosome 2 and comprises 6 exons within a 3.9 kb genomic locus encoding at least four alternatively spliced transcripts (NKG5, 519, 520 and 522). The predicted amino acid sequence of transcript 519 can be found in U.S. Pat. No. 4,994,369 (incorporated herein by reference). Granulysin is a cationic molecule present in the granules of cytotoxic T cells and NK cells. Granulysin is expressed as a 15 kD naturally occurring precursor protein, known as 15 kD granulysin. Granulysin is constitutively secreted as the 15 kD precursor form, a portion of which is localized in cytolytic granules where it is post-translationally processed into a 9 kD form. Granulysin in the 9 kD form is known to exhibit potent cytotoxic activity against a broad panel of microbial targets, including transplant cells, bacteria, fungi, and parasites (Stenger et al., *Immunol. Today* 20:390-394, 1999; Clayberger and Krensky, *Curr. Opin. Immunol.* 15:560-565, 2003; Hanson et al., *Mol. Immunol.* 36:413-422, 1999; Sarwal et al., *Hum. Immunol.* 62:21-31, 2001; Wang et al., *J. Immunol.* 165:1486-1490, 2000), and damaging negatively charged cell membranes because of its positive charge (Kaspar et al., *J. Immunol.* 167:350-356, 2001). Deng et al. (*J. Immunol.* 174: 5243-5248, 2005) also observed that the 9 kD post-translational form of granulysin possessed anti-microbial activity and chemotactic activity.

Until recently, full-length recombinant 15 kD granulysin had not been successfully isolated or characterized. Animal models are difficult to prepare because mice do not possess the granulysin gene.

As referred to herein, 15 kD granulysin refers to the full-length precursor form of granulysin with a molecular weight of about 15 kilodaltons (and is substantially free of 9 kD granulysin). The instant invention is distinct from the previously identified and characterized form of 9 kD granulysin (referred to in the art, and herein, as "9 kD granulysin") which has an approximate molecular weight of about 9,000 daltons. In a preferred embodiment, 15 kD granulysin includes SEQ ID NO. 1. In additional embodiments, 15 kD granulysin includes SEQ ID NO: 2, a nucleic acid sequence encoding 15 kD granulysin. In some embodiments of the disclosed methods and compositions, the 15 kD granulysin includes peptides that have at least 95%, at least 98%, or at least 99% sequence identity to SEQ ID NO:1, and retain the described activity of SEQ ID NO: 1. Alternatively, one, two or three conservative substitutions can be made to SEQ ID NO: 1. In other embodiments, the 15 kD granulysin includes nucleic acid molecules that have at least 85%, at least 90%, at least 95%, at least 98%, or at least 99% sequence identity to SEQ ID NO: 2 and encode a polypeptide that retains the described activity of 15 kD granulysin.

Nucleic acid and protein sequences for 15 kD granulysin are publicly available. For example, GENBANK® Accession No. NM_012483 discloses an exemplary 15 kD granulysin nucleic acid sequence, and GENBANK® Accession No. NP_036615 discloses an exemplary 15 kD granulysin amino acid sequence, both of which are incorporated by reference as provided by GENBANK® on Oct. 8, 2010.

Immune response: A response of a cell of the immune system, such as a B cell, or a T cell to a stimulus. In one embodiment, the response is specific for a particular antigen (an "antigen-specific response"). In another embodiment, the response is an inflammatory response.

A "parameter of an immune response" is any particular measurable aspect of an immune response, including, but not limited to, cytokine secretion (IL-6, IL-10, IFN-γ, etc), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. One of skill in the art can readily identify a significant increase using known statistical methods.

Immunocompromised: An immunocompromised subject is a subject who is incapable of developing or unlikely to develop a robust immune response, usually as a result of disease, malnutrition, or immunosuppressive therapy. An immunocompromised immune system is an immune system that is functioning below normal. Immunocompromised subjects are more susceptible to opportunistic infections, for example viral, fungal, protozoan, or bacterial infections, prion diseases, and certain neoplasms. Those who can be considered to be immunocompromised include, but are not limited to, subjects with AIDS (or HIV positive), subjects with severe combined immune deficiency (SCID), diabetics, subjects who have had transplants and who are taking immunosuppressives, and those who are receiving chemotherapy for cancer. Immunocompromised individuals also includes subjects with most forms of cancer (other than skin cancer), sickle cell anemia, cystic fibrosis, those who do not have a spleen, subjects with end stage kidney disease (dialysis), and those who have been taking corticosteroids on a frequent basis by pill or injection within the last year. Subjects with severe liver, lung, or heart disease also may be immunocompromised.

Immunostimulatory CpG motifs: Immunostimulatory sequences that trigger monocytes, macrophages and lymphocytes to produce a variety of pro-inflammatory cytokines and chemokines. CpG motifs are found in bacterial DNA. The innate immune response elicited by CpG DNA reduces host susceptibility to infectious pathogens, and can also trigger detrimental inflammatory reactions. Immunostimulatory CpG motifs are found in "D" and "K" type oligodeoxynucleotides (see, for example PCT Publication No. WO 01/51500, published on Jul. 19, 2001).

Interferon alpha (IFN-α): At least 23 different variants of IFN-α are known. The individual proteins have molecular masses between 19-26 kD and consist of proteins with lengths of 156-166 and 172 amino acids. All IFN-α subtypes possess a common conserved sequence region between amino acid positions 115-151 while the amino-terminal ends are variable. Many IFN-α subtypes differ in their sequences at only one or two positions. Naturally occurring variants also include proteins truncated by 10 amino acids at the carboxyl-terminal end.

There are at least 23 different IFN-α genes. They have a length of 1-2 kb and are clustered on human chromosome 9p22. Based upon the structures two types of IFN-alpha genes, designated class I and II, are distinguished. They encode proteins of 156-166 and 172 amino acids, respectively.

Interferon gamma (IFN-γ): IFN-γ is a dimeric protein with subunits of 146 amino acids. The protein is glycosylated at two sites, and the pI is 8.3-8.5. IFN-γ is synthesized as a precursor protein of 166 amino acids including a secretory signal sequence of 23 amino acids. Two molecular forms of the biologically active protein of 20 and 25 kD have been described. Both of them are glycosylated at position 25. The 25 kD form is also glycosylated at position 97. The observed differences of natural IFN-γ with respect to molecular mass and charge are due to variable glycosylation patterns. 40-60 kD forms observed under non-denaturing conditions are dimers and tetramers of IFN-γ. The human gene has a length of approximately 6 kb. It contains four exons and maps to chromosome 12q24.1.

Interleukin-2: IL-2 is a cytokine having a length of 133 amino acids. IL-2 has been approved by the Food and Drug Administration (FDA) for the treatment of some forms of cancer, including kidney cancer, melanoma, and lymphoma. IL-2 can be administered via intravenous or subcutaneous injections, where IL-2 is typically administered daily, or twice daily, over a course of several days, until the course of treatment is complete. IL-2 functions as an immune modulator, and stimulates the proliferation and activation of immune cells such as T cells and Natural Killer cells.

Interleukin-4: The gene for Interleukin-4 (IL-4) is located on chromosome 5 at position q31. The nucleotide sequence of IL-4 was isolated in 1986 and confirmed its similarity to the mouse protein, B-Cell Stimulating Factor (BCSF-1). IL-4 is a cytokine that differentiates naïve helper T cells into Th2 cells. IL-4 stimulates the production of IgE and induces eosinophil-mediated attacks against helminthic infections and allergens. IL-4 is currently used for therapeutic intervention in a wide range of malignant diseases as an anti-tumor agent Interleukin-10: IL-10 is a homodimeric protein with subunits having a length of 160 amino acids that is a cytokine. Human IL-10 is a cytokine with 73 percent amino acid homology to murine IL-10. The human IL-10 gene contains four exons. IL10 inhibits the synthesis of a number of cytokines such as IL-2 and IFN-γ in Th1 subpopulations of T cells but not of Th2. IL10 can be detected with an ELISA assay. In addition, the murine mast cell line D36 can be used to bioassay human IL10. The intracellular factor can also be detected by flow cytometry.

Isolated: An "isolated" biological component (such as a nucleic acid, peptide or protein) has been substantially separated, produced apart from, or purified away from other biological components in the cell of the organism in which the component naturally occurs, e.g., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphonuclear leukocytes (neutrophils, eosinophils, basophils) and mononuclear leukocytes (monocytes and lymphocytes). When an infection is present, the production of leukocytes increases.

Mammal: This term includes both human and non-human mammals. Similarly, the term "subject" includes both human and veterinary subjects.

Maturation: The process in which an immature cell, such as an immature dendritic cell, changes in form or function to become a functionally mature dendritic cell.

Neoplasm: An abnormal cellular proliferation, which includes benign and malignant tumors, as well as other proliferative disorders.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, intraarticularly, or subcutaneously, and various surface applications including intranasal, intradermal, and topical application, for instance.

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in this invention are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Inhibiting or treating a disease: "Inhibiting" a disease refers to inhibiting the full development of a disease, for example in a person who is known to have a predisposition to a disease such as an autoimmune disorder. An example of a person with a known predisposition is someone with a history of familial cancers, or who has been exposed to factors that predispose the subject to a condition, such smoking or occupational exposure to a carcinogen Inhibition of a disease can span the spectrum from partial inhibition to substantially complete inhibition (prevention) of the disease. In some examples, the term "inhibiting" refers to reducing or delaying the onset or progression of a disease. A subject to be administered with a therapeutically effective amount of the pharmaceutical compound to inhibit or treat the above illnesses can be identified by standard diagnosing techniques for such a disorder, for example, basis of family history, or risk factor to develop the disease or disorder. In contrast, "treatment" refers to a therapeutic intervention that ameliorates a sign or symptom of a disease or pathological condition after it has begun to develop.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation. In some embodiments, a purified preparation contains at least 60%, at least 70%, at least 80%, at least 85%, at least 90%, at least 95% or more of the protein or peptide.

Subject at Risk: An individual, such as a human or a veterinary subject, that is prone to developing certain conditions, such as a tumor. This can be due to their age, genotype, or due to an environmental exposure. Examples are a human subject who is exposed to a carcinogen due to an occupational exposure, or a human subject exposed to cigarette smoke, either because that individual smokes or due to exposure to second-hand smoke, or a subject exposed to ultraviolet light, such as due to tanning, or a subject genetically pre-disposed to developing a tumor.

T cell or T lymphocyte: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cell is a cytotoxic T lymphocyte. In another embodiment, a CD8 cell is a suppressor T cell.

As used herein, "allogeneic" encompasses a genetically different phenotype present in non-identical individuals of the same species. Cells, tissues, organs, and the like from, or derived from, a non-identical individual of the same species are "allogeneic." An "alloantigen" encompasses any antigen recognized by different individuals of the same species. Organisms, cells, tissues, organs, and the like from, or derived from, a single individual, or from a genetically identical individual are "autologous."

Therapeutic agent: Used in a generic sense, it includes treating agents, prophylactic agents, and replacement agents.

Therapeutically effective dose or amount: A dose or quantity of a specified compound sufficient to inhibit advancement, or to cause regression of the disease, or which is capable of relieving symptoms caused by the disease, such as pain or swelling. For instance, this can be the amount or dose of composition required to inhibit a tumor, delay the development of a tumor, or reduce the risk of developing a tumor. In one embodiment, a therapeutically effective amount of the composition is the amount that alone, or together with one or more additional therapeutic agents (such as additional antineoplastic agents or immunosuppressive agents), induces the desired response, such as inhibition or treatment of a tumor, such as skin cancer. In other examples, it is an amount of the composition that can cause regression of an existing tumor, or treat one or more signs or symptoms associated with a tumor, in a subject. The preparations disclosed herein are administered in therapeutically effective amounts.

In one example, a desired response is to inhibit, and in some examples prevent, the development of a tumor. In another example, a desired response is to delay the development, progression, or metastasis of a tumor, for example, by at least about 3 months, at least about six months, at least about one year, at least about two years, at least about five years, or at least about ten years. In a further example, a desired response is to decrease the occurrence of cancer, such as melanoma, colon cancer, liver cancer or lung cancer. In another example, a desired response is to decrease the signs and symptoms of cancer, such as the size, volume, or number of tumors or metastases. For example, the composition including 15 kD granulysin can, in some examples, decrease the size, volume, tumor burden or number of tumors (such as colorectal tumors) by a desired amount, for example by at least 5%, at least 10%, at least 15%, at least 20%, at least 25%, at least 30%, at least 50%, at least 75%, or even at least 90%, as compared to a response in the absence of the therapeutic composition.

The effective amount of 15 kD granulysin that is administered to a human or veterinary subject will vary depending upon a number of factors associated with that subject, for example the overall health of the subject. An effective amount of an agent can be determined by varying the dosage of the product and measuring the resulting therapeutic response, such as the regression of a tumor. Effective amounts also can be determined through various in vitro, in vivo or in situ, immunoassays. The disclosed agents can be administered in a single dose, or in several doses, as needed to obtain the desired response. However, the effective amount can be dependent on the source applied, the subject being treated, the severity and type of the condition being treated, and the manner of administration.

A therapeutically effective amount of 15 kD granulysin can be administered systemically or locally. In addition, an effective amount of 15 kD granulysin can be administered in a single dose, or in several doses, for example daily, during a course of treatment. For example, a therapeutically effective amount of 15 kD granulysin can vary from about 0.01 mg/kg body weight to about 1 g/kg body weight in some specific, non-limiting examples, or from about 0.01 mg/kg to about 60 mg/kg of body weight, based on efficacy.

The compositions disclosed herein have equal applications in medical and veterinary settings. Therefore, the general term "subject" is understood to include all animals with a granulysin gene, including, but not limited to, humans or veterinary subjects, such as other non-human primates, dogs, cats, horses, pigs, cows, and transgenic mice.

Toll-Like Receptors: Toll-Like Receptors (TLRs) are a class of proteins that play an important role in the innate immune response. They are receptors that recognize structurally conserved molecules derived from pathogens. Upon entry of a pathogen derived molecule into a host, such as via the lungs or skin, the TLRs activate a host's immune cell responses. TLRs are a type of pattern recognition receptor (PRR) and recognize molecules that are broadly shared among pathogens but are distinguishable from the host, collectively referred to as, pathogen associated molecular patterns (PAMPs). It has been estimated that most mammalian species have between ten and fifteen types of TLRs. At least thirteen TLRs (named TLR1 to TLR13) have been identified in humans and mice together, and equivalent forms of many of these have been found in other mammalian species. However, equivalents of certain TLRs found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Examples of molecules that can act as TLR agonists include flagellin, zymosan, poly (I:C), CpG oligonucleotides, endotoxins, resiquimod, imiquimod, gardiquimod, and lipopolysaccharide (LPS).

Tumor: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the blood vessels or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytoma, sebaceous gland carcinoma, papillary carcinoma, papillary adenocarcinoma, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma, and retinoblastoma).

In several examples, a tumor is melanoma, esophageal cancer, liver cancer, gastrointestinal cancer, colon cancer, or lung carcinoma. In another example, a tumor is a skin tumor.

Vaccine: As defined herein, a vaccine may be an immunogenic composition for stimulating an immune response against a target antigen. Such compositions may include a preparation of attenuated microorganisms (including but not limited to bacteria and viruses), living microorganisms, killed microorganisms, antigens (including but not limited to tumor antigens), polypeptides, nucleic acids, or vectors encoding antigens, administered for the inhibition, amelioration or treatment of non-infectious diseases, allergies, and tumors.

III. Overview of Several Embodiments

A method is provided for the enhancement of T cell mediated immune responses. In one embodiment, the method provides for the activation of monocytes, through the administration of 15 kD granulysin.

In another embodiment, the method provides for the differentiation of monocytes into monocyte-derived dendritic cells, thereby stimulating an immune response or up-regulating and already activated immune response in a host.

In yet another embodiment, 15 kD granulysin can be used to treat or inhibit disease, or treat the symptoms of disease, such as an autoimmune disorder or a tumor. In another aspect, 15 kD granulysin can be used as an adjuvant for a vaccine, such as a bacterial or viral vaccine.

In one embodiment, a target antigen is delivered to peripheral tissues in combination with monocyte-derived dendritic cells, and may be given as a combined formulation, or as a separate formulation. The antigen may be further provided in a booster dose, in combination with other adjuvants as is known in the art.

On maturation, the monocyte-derived dendritic cells migrate to lymphatic organs, particularly T cell rich regions of the lymph nodes, where T cell activation occurs. Therefore, although administration of the antigen and monocyte-derived dendritic cells may be localized, the resulting immune response is not limited to the tissue of administration.

Conditions of particular interest for use with the disclosed methods involve situations where the host response is suboptimal, for example in conditions of chronic infection, a lack of immune response to tumor antigens, poor responsiveness to allergens, and the like. In one aspect, the antigen is a tumor antigen and is used to enhance the host's immune response to tumor cells present in the host. In this context, the method can be either therapeutic or prophylactic in nature.

Mammalian species that may require enhancement of an immune response include canines and felines; equines, bovines, ovines, porcines, etc., and primates, particularly humans. Animal models such as primate, canine, or transgenic mouse models can be used for experimental investigations. Animal models of interest include models that involve the up-regulation of immune responses to tumors, allergens and/or infection.

A. Methods for Inhibiting or Treating Tumors

Methods are disclosed for inhibiting tumors, for example, inhibiting formation of a tumor, treating a tumor, or reducing the risk of developing a tumor by delivering 15 kD granulysin to a subject, either alone or in combination with one or more other anti-tumor agents. In some embodiments, methods are disclosed for inhibiting conversion of a benign tumor to a malignant tumor, or inhibiting metastasis. The tumor can be any tumor, including, but not limited to, tumors of the esophagus, lung, liver, kidney, skin, colon and gastrointestinal tract. In some examples, the tumor can be a mesothelioma, or stomach cancer. In other examples, the tumor is a skin tumor, such as, but not limited to, a squamous cell carcinoma or a basal cell carcinoma.

The methods disclosed include selecting a subject in need of treatment for the condition and administering to the subject a therapeutically effective amount of 15 kD granulysin. Additional agents, such as anti-bacterial, anti-viral, or other therapeutic agents, such as a chemotherapeutic agent, can also be administered to the subject. However, in other embodiments substantially pure 15 kD granulysin is administered, for example 15 kD granulysin in the substantial or complete absence of 9 kD granulysin.

In several embodiments, the disclosure is further directed to anti-tumor methods for decreasing the risk of developing a tumor in a subject exposed to a carcinogen, or inhibiting or delaying the development of a tumor. The tumor can be, for example, skin cancer, such as basal cell carcinoma, keratinocyte carcinoma or squamous cell carcinoma. In another example, the tumor can be an esophageal, stomach, lung, kidney, brain, or colon tumor. In other embodiments, 15 kD granulysin is used for the inhibition of mesothelioma.

Treatment of the conditions described herein can be prophylactic or, alternatively, can be initiated after the development of a condition described herein. Treatment that is prophylactic, for instance, can be initiated before a subject manifests symptoms of a condition. In some examples, such as for skin cancer, treatment can be initiated before or during exposure to an agent that damages DNA, such as a result of an exposure to a carcinogen, UV light, oxidative stress, alkylation damage or deamination. In some examples, treatment can be following the exposure to the DNA damaging agent, but before the appearance of a tumor. In some examples, treatment can occur before or during exposure to a carcinogen, such as an occupational exposure, e.g., asbestos, or smoking. Treatment prior to the development of the condition is referred to herein as treatment of a subject that is "at risk" of developing the condition. Accordingly, administration of 15 kD granulysin can be performed before, during, or after the occurrence of the conditions described unless otherwise indicated herein.

Treatment initiated after the development of a condition may result in decreasing the severity of the symptoms of one, or more, of the conditions, or completely removing the symptoms, or reducing metastasis.

Non-limiting examples of subjects particularly suited to receiving 15 kD granulysin before diagnosis of disease include those whose skin may be exposed to excessive natural or artificial UV irradiation, or subjects who are exposed to a carcinogen due to an occupational exposure, such as an industrial chemical, or due to smoking, or exposure to a noninfectious agent. In one example, a subject who has been exposed to asbestos or silica is at risk for developing mesothelioma. Alternatively the subject may be someone with a genetic predisposition to develop a tumor (such as a family history of cancer, such as breast, lung or colon cancer), an infectious risk factor that predisposes to tumor development (such as HPV exposure or HCV or Epstein-Barr virus infection), or a genetic disorder that predisposes to tumor development (such as Gardner's syndrome, xeroderma pigmentosum, Fanconi's anemia, Bloom's syndrome, or familial adenomatous polyposis). In particular examples the subject has an immunodeficiency (such as HIV infection or a drug-induced immunodeficiency as in someone who has undergone an organ transplant and is taking immunosuppressive therapy). In another example, the subject has an inherited immunodeficiency (such as ataxia telangiectasia or Wiskott-Aldrich syndrome).

In some examples, the subject has not yet developed a tumor. In other examples, the subject has a benign tumor that can convert into a malignant or even metastatic tumor. For example, the subject may be a smoker who has not developed lung cancer; subjects exposed to large or excessive amounts of UV light, but who have not developed skin cancer, such as melanoma or basal cell carcinoma; or a subject with a familial disposition to develop melanoma, for example a mutation in the CDKN2A, KIT, MDM2, or BRAF gene, or a diagnosis of xeroderma pigmentosum, retinoblastoma, Werner syndrome, hereditary breast and ovarian cancer, or Cowden syndrome. In other embodiments a subject is selected who has clinical risk factors for developing melanoma, such as dysplastic nevi, extensive freckling, or a past history of one or multiple melanomas. In one aspect of the invention, formation of tumors is delayed, inhibited or decreased. The types of tumors that may occur in response to an agent that damages DNA in the skin include actinic keratosis, basal cell carcinoma, squamous cell carcinoma, and melanoma.

Whether the formation of tumors in a subject is reduced can be determined for example, by the use of animal models, for instance transgenic mice that have been exposed to solar-simulated light or exposure to sunlight, or using a model wherein an animal is exposed to a DNA alkylating agent. Solar-simulated light is light having a spectral profile which is similar to natural solar irradiation, e.g. the emission spectrum of a solar simulator looks similar to spectrum of a solar noon day. Wavelengths of light include about 295-400 nm so is inclusive of UVA and UVB, but not UVC which does not penetrate the ozone layer of the atmosphere (see, for instance, Yoon et al., *J. Mol. Biol.* 299:681-693, 2000). However, the methods are of use with any initiating agent, including agents known to cause cancer (such as the carcinogens in tobacco smoke). In some embodiments, the subject is at risk of exposure to an initiating agent due to an occupational exposure.

In another embodiment, the presence of a tumor can be determined by methods known in the art, and typically include cytological and morphological evaluation. The cells suspected of being cancerous can be in vivo or ex vivo, including cells obtained from a biopsy.

The composition including 15 kD granulysin may be formulated in a variety of ways for administration to a subject to delay, inhibit, reduce the risk of developing, or treat a tumor of interest. For example, the composition can be formulated for application such that it inhibits metastasis of an initial lesion.

The 15 kD granulysin can be administered to slow or inhibit the growth of cells, such as tumor cells, or to inhibit the conversion of a benign lesion to a malignant one. In these applications, a therapeutically effective amount of 15 kD granulysin is administered to a subject in an amount sufficient to inhibit growth, replication or metastasis of tumor cells, or to inhibit an indication or a symptom of the tumor. In some embodiments, 15 kD granulysin is administered to a subject to inhibit or prevent the development of metastasis, or to decrease the number of micrometastases, such as micrometastases to the regional lymph nodes (Goto et al., *Clin. Cancer Res.* 14:3401-3407, 2008).

Pharmaceutical compositions of 15 kD granulysin may also include an additional therapeutic agent, for example, an anti-inflammatory agent, a co-stimulatory molecule, a TLR agonist (such as LPS), a cytokine (such as IL-4), a UV protectant or an additional chemotherapeutic agent. Contemplated herein are pharmaceutical compositions in which the 15 kD granulysin is co-administered with the additional therapeutic agent. In one embodiment, the 15 kD granulysin may be administered before, after, or during the administration of the additional therapeutic agent. In another example, the 15 kD granulysin can be administered up to about 3 days prior to the administration of the additional therapeutic agent to prime the immune system, thus providing a robust and sufficient immune response following administration of the additional therapeutic agent to treat, ameliorate or delay the onset of the disease or disorder.

Pharmaceutical compositions for the treatment of at least, but not limited to, the above conditions are thus provided for both local (such as topical or inhalational) use and for systemic (such as oral or intravenous) use. Therefore, the disclosure includes within its scope pharmaceutical compositions formulated for use in human or veterinary medicine. While the composition will typically be used to treat human subjects it may also be used to treat similar or identical diseases in other vertebrates, such as other primates, dogs, cats, horses, and cows. A suitable administration format may best be determined by a medical practitioner for each subject individually. Various pharmaceutically acceptable carriers and their formulation are described in standard formulation treatises, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). See also Wang, Y. J. and Hanson, M. A., *Journal of Parenteral Science and Technology*, Technical Report No. 10, Supp. 42: 2S, 1988. Generally, the dosage form of the pharmaceutical composition will be determined by the mode of administration chosen. Additional information about such pharmaceutical compositions is provided in Example 10.

The 15 kD granulysin can be co-administered with a target antigen. In one embodiment, the antigen may include a DNA vaccine. For example, the DNA vaccine can be a Human Papilloma Virus (HPV) vaccine administered with or shortly after (up to about 3 days) administration of the 15 kD granulysin to treat or control infection by the virus. In another embodiment, the target antigen is a tumor antigen such as prostate-specific membrane antigen (PSMA). PSMA expression is significantly elevated in carcinoma of the prostate, particularly in metastastic disease and recurrent disease after hormone therapy (androgen deprivation) fails. These properties make PSMA an ideal target for anti-cancer vaccines. In one example, 15 kD granulysin can be administered simultaneously or up to about 3 days after administration of PMSA to the host. The co-administration of PMSA and 15 kD granulysin permits "priming" of the immune system via differentiation of monocytes into monocyte-derived dendritic cells, which in turn enhance antigen presentation to naïve T cells. In addition, the monocyte-derived dendritic cells can be stimulated to secrete cytokines, such as interferon-γ and IL-12 particularly desirable in cancer immunotherapy.

In some embodiments, the compositions disclosed are utilized in a "prime boost" regimen. An example of a "prime boost" regime may be found in Yang et al., (*J. Virol.* 77:799-803, 2002), which is incorporated herein by reference. In these embodiments, the 15 kD granulysin is delivered to a subject, thereby "priming" the immune response of the subject, and then a second immunogenic composition such as a DNA vaccine is utilized as a "boost" vaccination. In one embodiment, a priming composition and a boosting composition are combined into a single formulation. For example, a single formulation may comprise 15 kD granulysin as the priming component and a vector expressing PMSA as the boosting component. In this example, the compositions may be contained in a single vial where the two components are mixed together. In another embodiment, the priming composition may be administered simultaneously with the boosting composition, but in separate formulation where the priming and boosting compositions are separated.

The terms "priming" and "boosting" as used herein may refer to the initial and subsequent immunizations, respectively, e.g., in accordance with the definitions these terms normally have in immunology. However, in certain embodiments, e.g., where the priming component and boosting component are in a single formulation, initial and subsequent immunizations may not be necessary as both the "prime" and the "boost" compositions are administered simultaneously.

In other examples, the 15 kD granulysin is co-administered with a target antigen in the form of a fusion protein. In some examples, 15 kD granulysin is administered to a subject as a fusion protein with a tumor antigen, such as a prostate tumor antigen (for example, PMSA or prostatic acid phosphatase (PAP)). Methods for making fusion proteins are well known to those skilled in the art. For example U.S. Pat. No. 6,057,133 to Bauer et al. (herein incorporated by reference) discloses methods for making fusion molecules composed of human interleukin-3 (hIL-3) variant or mutant proteins functionally joined to a second colony stimulating factor, cytokine, lymphokine, interleukin, hematopoietic growth factor or IL-3 variant. Similar methods can be used to generate fusion proteins including 15 kD granulysin linked to other amino acid sequences, such as a target antigen (for example, PAP). Linker regions can be used to space the two portions of the protein from each other and to provide flexibility between them. The linker region is generally a polypeptide of between 1 and 500 amino acids in length, for example less than 30 amino acids in length, for example between 5 and 20 amino acids in length. The linker joining the two molecules can be designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of the two regions. Typically surface amino acids in flexible protein regions include Gly, Asn and Ser. Other neutral amino acids, such as Thr and Ala, can also be used in the linker sequence. Additional amino acids can be included in the linker due to the addition of unique restriction sites in the linker sequence to facilitate construction of the fusions. Other moieties can also be included, as desired. These can include a binding region, such as avidin or an epitope, such as a polyhistadine tag, which can be useful for purification and processing of the fusion protein. In addition, detectable markers can be attached to the fusion protein, so that the traffic of the fusion protein through a body or cell can be monitored conveniently. Such markers include radionuclides, enzymes, fluorophores, and the like.

Fusing of a 15 kD granulysin nucleic acid sequence with a nucleic acid sequence encoding another protein can be accomplished by the use of intermediate vectors. Alternatively, one gene can be cloned directly into a vector containing the other gene. Linkers and adapters can be used for joining the nucleic acid sequences, as well as replacing lost sequences, where a restriction site was internal to the region of interest. Genetic material (DNA) encoding one polypeptide, peptide linker, and the other polypeptide is inserted into a suitable expression vector which is used to transform prokaryotic or eukaryotic cells, for example bacteria, yeast, insect cells or mammalian cells. The transformed organism is grown and the protein isolated by standard techniques, for example by using a detectable marker such as nickel-chelate affinity chromatography, if a polyhistadine tag is used. The resulting product is therefore a new protein, a fusion protein, which includes 15 kD granulysin joined by a linker region to a second protein or a portion of a second protein (such as a target antigen). To confirm that the fusion protein is expressed, the purified protein is subjected to electrophoresis in SDS-polyacrylamide gels, and transferred onto nitrocellulose membrane filters using established methods. The protein products can be identified by Western blot analysis using antibodies directed against the individual components, such as a polyhistadine tag and PA.

The nucleic acid sequence encoding a 15 kD granulysin fusion protein can be under the control of a suitable promoter. Suitable promoters include, but are not limited to, the gene's native promoter, retroviral LTR promoter, or adenoviral promoters, such as the adenoviral major late promoter, the CMV promoter, the RSV promoter, inducible promoters, such as the MMTV promoter, the metallothionein promoter, heat shock promoters, the albumin promoter, the histone promoter, the α-actin promoter, TK promoters, B19 parvovirus promoters, and the ApoAI promoter.

In one embodiment, a composition including 15 kD granulysin and an antigen are delivered to a subject by methods described herein, thereby achieving an effective therapeutic and/or an effective prophylactic immune response. Additional information about modes of administering 15 kD granulysin is provided in Example 11.

The therapeutically effective amount of 15 kD granulysin will be dependent on the subject being treated, the severity and type of the condition, and the manner of administration. For example, a therapeutically effective amount of 15 kD granulysin can vary from about 0.01 μg per kilogram (kg) body weight to about 1 g per kg body weight, such as about 1 μg to about 5 mg per kg body weight, or about 5 μg to about 1 mg per kg body weight. The exact dose is readily determined by one of ordinary skill in the art based on the potency of the specific formulation, the age, weight, sex and physiological condition of the subject.

A therapeutically effective amount of 15 kD granulysin can be administered with an antigen from which a subject requires protection. In one example, the target antigen is a tumor antigen, for example, an oncofetal antigen (e.g., carcinoembryonic antigen (CEA), alpha-fetoprotein or an antigen from the MAGE family). In a specific, non-limiting example, the tumor antigen can be a differentiation antigen, for example, a melanoma differentiation antigen (e.g., MART-1, MAGE 1, MAGE 3, gp 100, or tyrosinase). In another embodiment, the target antigen can be a vaccine, such as a DNA vaccine (e.g., HPV, HBV or EBV vaccine). The amount of target antigen administered to the subject is dependent on a number of factors, such as the condition being treated, the severity of the condition, route of administration and the anticipated duration of treatment. It will be apparent to one of skill in the art that the amount or concentration of antigen to be administered to the subject can be determined by conventional means by an attending physician or veterinarian.

In one embodiment for the inhibition and/or treatment of melanoma, a therapeutically effective amount of 15 kD granulysin can be administered in conjunction with surgery and/or with another therapeutic agent, such as a chemotherapeutic agent (e.g., 5-fluorouracil, cisplatin, paclitaxel, doxorubicin or cyclophosphamide). In another specific, non-limiting example, a therapeutically effective amount of 15 kD granulysin can be used for the treatment of a tumor in conjunction with administration of a cytokine, for example interleukin-4 (IL-4) and a toll-like receptor agonist, for example, lipopolysaccharide. In this example, the cytokine and toll-like receptor agonist can be administered prior to, during, or after administration of the 15 kD granulysin.

In another embodiment, it is contemplated that a monocyte can be removed from a subject, and that the monocyte can be primed and manipulated ex vivo to become a dendritic cell. The dendritic cell may be administered back into the subject, as a method of directly increasing the number of dendritic cells in the subject. Alternatively, the dendritic cell can be manipulated ex vivo by exposure to a target antigen. The target antigen will be processed by the dendritic cell and the antigen-presenting dendritic cell can be re-introduced into the subject, thereby activating an immune response in the subject if the target antigen is present. As described herein, the therapeutically effective amount of 15 kD granulysin can be administered with a therapeutically effective amount of at least one additional therapeutic agent, such as a cytokine, a chemokine, a toll-like receptor, a chemotherapeutic agent, an anti-microbial agent, an anti-inflammatory agent (such as a steroidal anti-inflammatory agent or a non-steroidal anti-inflammatory agent) or a combination thereof.

B. Methods for Inducing Dendritic Cell Maturation

Monocytes are produced in the bone marrow from hematopoietic stem cells called monoblasts. Monocytes circulate in the blood vessels for about one to about three days and then typically move to tissues throughout the body. In response to inflammation stimuli, monocytes migrate from the blood vessels to the site of infection or inflammation where with other cells and factors the monocytes can initiate an immune response.

According to one embodiment, methods of producing dendritic cells from monocytes are disclosed. The method includes contacting a monocyte (MO) with a therapeutically effective amount of 15 kD granulysin, thereby inducing differentiation of the monocyte into a monocyte-derived dendritic cell (MO-DC). In one embodiment, an additional agent that enhances dendritic cell maturation is administered in conjunction with 15 kD granulysin. In another example, an additional dendritic cell maturation agent may be administered after the monocyte differentiation step has taken place. Specific, non-limiting examples of additional agents that enhance dendritic cell maturation include, but are not limited to, granulocyte macrophage colony stimulating factor (GM-CSF), macrophage colony stimulating factor (M-CSF), flt-3, interleukin-4 (IL-4), Toll-Like Receptor (TLR) agonists (such as polyriboinosinic polyribocytidylic acid (poly (I:C)), lipopolysaccharide (LPS), Tumor Necrosis Factor-alpha (TNF-α), CpG motif-containing oligonucleotides, imiquimod, interleukin-6 (IL-6), interleukin-13 (IL-13), interleukin-7 (IL-7), interferon-alpha (IFN-α), heparan sulfate, calcium ionophore, or a combination of two or more thereof. In one embodiment, the monocyte is contacted with a therapeutically effective amount of 15 kD granulysin in the presence of GM-CSF and IL-4.

GM-CSF as defined herein includes the gene product of the human GM-CSF gene and naturally occurring or engineered variants thereof. The nucleotide and the amino acid sequence of the human GM-CSF is found in Genbank Accession no. NM_000758 (incorporated herein by reference as present in GenBank on Oct. 8, 2010). In addition, some naturally occurring variants of GM-CSF are listed in NM_000758. GM-CSF is also known as colony stimulating factor 2 (CSF2) and is anticipated as a form of GM-CSF. The invention also includes the use of derivatives of GM-CSF that retain the biological activity of wild-type GM-CSF, e.g., that in the presence of 15 kD granulysin stimulate the differentiation of monocytes to monocyte-derived dendritic cells. A derivative of GM-CSF includes a fragment, fusion or modification or analogue thereof, or a fusion or modification of a fragment thereof. A fragment of GM-CSF includes any portion of the glycoprotein that stimulates the production of monocyte-derived dendritic cells in the presence of 15 kD granulysin. It is preferred that the fragment has at least 50%, at least 70%, or at least 90% of the activity of full-length GM-CSF. In another embodiment, the fragment has 100% or more of the activity of full-length GM-CSF.

The invention also contemplates a fusion protein of full-length GM-CSF, or a fragment thereof, to another compound. In one embodiment, the fusion protein retains at least 50%, preferably at least 70%, and more preferably at least 90% of the activity of full-length GM-CSF. In another embodiment, the fusion protein retains at least 100% of the activity of full-length GM-CSF.

The derivatives as described above may be made using protein chemistry techniques for example by using partial proteolysis, or de novo synthesis. Alternatively, the derivatives may be made by recombinant DNA technology. Suitable techniques for cloning, manipulation, modification, and expression of nucleic acids, and purification of expressed proteins, are well known in the art and are described for example in Sambrook et al (2001) "*Molecular Cloning, a Laboratory Manual*", $3^{rd}$ edition, Sambrook et al (eds), Cold Spring Harbor Laboratory Press, Cold Spring Harbor, N.Y., USA, incorporated herein by reference.

The invention also includes modifications of full-length GM-CSF or a fragment thereof, that stimulates the production of monocyte-derived dendritic cells from their progenitor cells and which in the presence of 15 kD granulysin cause monocytes to differentiation into dendritic cells and express dendritic cell phenotype markers such as CD86, CD11c, CD83 and HLA-DR.

Modifications of full-length GM-CSF include deglycosylating the glycoprotein either fully or partially. Other modifications include a full-length GM-CSF, or a fragment thereof, having a different glycosylation pattern from that found in naturally occurring human GM-CSF. Other modifications of full-length GM-CSF, or a fragment thereof, include amino acid insertions, deletions and substitutions, either conservative or non conservative, at one or more positions. Such modifications may be called analogues of GM-CSF. As defined herein "conservative substitutions" include combinations such as Gly, Ala; Val, Ile, Leu; Asp, Glu; Asn, Gln; Ser, Thr; Lys, Arg; and Phe, Tyr. Such modifications may be made using the methods of protein engineering and site-directed mutagenesis, as described in Sambrook et al.

GM-CSF and analogues thereof are described in at least the following publications, each of which is incorporated herein by reference to the extent that they describe GM-CSF and its analogues; U.S. Pat. No. 5,229,496; U.S. Pat. No. 5,391,485; U.S. Pat. No. 5,393,870; U.S. Pat. No. 5,602,007; Wong et al. (*Science* 228:810-815, 1985); Lee et al., (*Proc. Natl. Acad. Sci. USA* 82:4360-4364, 1985); and Cantrell et al., (*Proc. Natl. Acad. Sci. USA* 82:6520-6254, 1985).

While it is preferred that GM-CSF is human GM-CSF, GM-CSF from other species can also be used. However, it is anticipated that for application in which GM-CSF is administered to a subject, the GM-CSF is preferably from the same species as the subject. Thus, if the GM-CSF is to be administered to a human subject, the GM-CSF is preferably human GM-CSF.

In one embodiment, GM-CSF suitable for the practice of this invention is Sargramostim, the proper name for yeast-derived recombinant human GM-CSF, sold under the trade name Leukine® marketed by Bayer HealthCare Pharmaceuticals (Morristown, N.J.). Leukine® is a recombinant human GM-CSF produced in *S. cerevisiae* expression system. Leukine® is a glycoprotein of 127 amino acids characterized by 3 primary molecular species. The amino acid sequence of Leukine® differs from human GM-CSF by a substitution of leucine at position 23, and the carbohydrate moiety may be different from the native protein.

Typically, to generate dendritic cells in vitro, it is useful to purify monocytes and monocyte precursors from other contaminating cell types. This is commonly achieved through adherence of monocytes to a plastic polystyrene surface, since monocytes have a greater tendency to adhere to plastic than other cell types found in peripheral blood. After substantially removing contaminant cells, for example by vigorous washing, the monocytes can be cultured with agents, such as cytokines that differentiate monocytes into dendritic cells. For example, Sallusto and Lanzavecchia (*J. Exp. Med.* 179: 1109-1118, 1994) disclose a method for differentiating a monocyte precursor into an immature dendritic cell.

It has been previously reported that the 9 kD form of granulysin activates monocytes to produce chemokines, including MCP-1 and RANTES, and cytokines, such as IFN-γ (Krensky *Biochem. Pharmacol.* 59:317-320, 2000). One of skill in the art can readily identify without undue experimentation the concentration of cytokines required for use with 15 kD granulysin. In one specific, non-limiting example, cytokines are present in a concentration of about 10 ng/ml to about 100 ng/ml, depending on the specific cytokine or cytokine cocktail to be used. Without being bound by theory, it is believed that agents such as GM-CSF and/or IL-4 act synergistically with 15 kD granulysin to enhance dendritic cell maturation.

In one embodiment, a monocyte is contacted with 15 kD granulysin in vitro to differentiate the monocyte into a monocyte-derived dendritic cell. To increase the number of monocyte cells in an animal, including humans, the subject can be treated with substances which stimulate hematopoiesis, such as GM-CSF or a CpG motif-containing oligonucleotide. For example, U.S. Pat. No. 5,994,126 discloses methods for isolating dendritic cell precursors and methods for increasing the number of dendritic cell precursors in a sample. Additionally, Krug et al. (*J. Immunol.* 170:3468-3477, 2003) disclose methods for producing and isolating monocyte-derived dendritic cells in culture upon incubation with CpG motif-containing oligonucleotides.

Thus, a monocyte can be contacted with a therapeutically effective amount of 15 kD granulysin for a sufficient period of time to differentiate into a dendritic cell in vitro. In one specific, non-limiting example, peripheral blood mononuclear cell cultures (PBMCs) are contacted with a therapeutically effective amount of 15 kD granulysin for a sufficient period of time to differentiate into mature dendritic cells in vitro. In one example, a culture of isolated peripheral blood monocytes containing about 1 to about $4 \times 10^6$ cells/ml are treated with a therapeutically effective amount of 15 kD granulysin in vitro. In this example, the concentration of 15 kD granulysin effective to induce maturation of the monocytes is about 1 nM to about 20 nM, or is about 5 nM to about 15 nM, or is about 10 nM. In one embodiment, the culture is maintained for at least one day. In another embodiment, the culture is maintained for about 2 days to about 14 days. In another embodiment, the culture is maintained for about 3 days to about 6 days.

A method for inducing differentiation of monocytes in vitro in the presence of a target antigen is disclosed. The method includes contacting a monocyte with a therapeutically effective amount of 15 kD granulysin and a therapeutically effective amount of a target antigen, thereby differentiating the monocyte into a monocyte-derived dendritic cell expressing the antigen of interest in vitro. In this instance, the monocyte can be contacted with the antigen of interest sequentially or simultaneously. The antigen can be any antigen, including, but not limited to, a tumor antigen, an antigen from a non-infectious agent, an allergen, or an antigen of use in a vaccine. Thus, in one embodiment, a monocyte is contacted with a therapeutically effective amount of 15 kD granulysin to produce a dendritic cell. In other examples, a monocyte is contacted with a therapeutically effective amount of 15 kD granulysin fused to an antigen (such as a tumor antigen) to produce a dendritic cell.

In a further embodiment, the dendritic cell is contacted with a therapeutically effective amount of a target antigen to induce presentation of the antigen by the dendritic cell. Thus, a mature antigen-presenting cell (APC) is produced by this method.

Exemplary antigens include, but are not limited to, epitopes or antigens from tumors, non-infectious agents or allergens. These antigens may be composed of protein, DNA, RNA, lipid, sugar, whole cell lysates, apoptotic cells, or any combination thereof. Some preferred antigens include soluble tumor protein antigens (such as CEA, MAGE-1, MART 1, tyrosinase), tumor-derived RNA, unfractionated acid-eluted peptides from the MHC class I molecules of tumor cells, and recombinant, purified, or inactivated vaccine proteins. Antigens of interest further include polypeptides and other immunogenic biomolecules, which can be produced by recombinant methods or isolated from natural sources. Complex antigens such as cell lysates inactivated (e.g. heat killed) viruses, bacterial cells or fractions thereof are also of use.

Potential tumor antigens for immunotherapy include, but are not limited to, tumor specific antigens, e.g. immunoglobulin idiotypes and T cell antigen receptors; oncogenes, such as p21/ras, p53, p210/bcr-abl fusion product; developmental antigens, e.g. MART-1/MelanA, MAGE-1, MAGE-3; GAGE family; telomerase; viral antigens, e.g. human papilloma virus; Epstein Barr virus; Hepatitis B virus; tissue specific self-antigens, e.g. tyrosinase, gp100, prostatic acid phosphatase, prostate specific antigen, PSMA, thyroglobulin, α-fetoprotein; and over-expressed self-antigens, e.g. her-2/neu; carcinoembryonic antigen, muc-1, and the like. Tumor cell derived protein extracts or RNA may be used as a source of antigen, in order to provide multiple antigens and increase the probability of inducing immunity to more than one tumor associated antigen.

As an alternative to injecting the target antigen into the host, endogenous tissue samples expressing the antigen can be used as an endogenous source of the antigen. For example, tumor cells that express a tumor antigen maybe injected alone, or in combination with a dendritic cell maturation agent, to serve as the source of tumor antigen. Administration of an endogenous tumor antigen and dendritic cell maturation agent in vivo leads to the activation and differentiation of monocytes that migrate to the tumor site and can process the endogenous tumor antigen. The processed tumor antigen is expressed on the surface of monocyte-derived dendritic cells that can interact with naïve T cells to produce an immune response against the target antigen.

It is to be appreciated that to induce tolerance to an antigen, a derivative of the antigen may be administered to the subject, and not the antigen itself. By derivative of an antigen it includes any portion of the antigen which can be presented by a class I or class II MHC molecule, and which induces tolerance to the antigen itself.

When the antigen is a protein, a derivative of the antigen is typically a peptide fragment of the antigen including a contiguous sequence of amino acids of the antigen capable of MHC binding. In one embodiment, the antigen is a fragment between about 6 and about 100 amino acids in length. In another embodiment, the antigen is a fragment between about 6 and about 50 amino acids in length. In yet another embodiment, the antigen is a fragment that is 6, 7, 8, 9, 10, 11, 12, 13, 14, 15, 16, 17, 18, 19, 20, 21, 22, 23, 24, or 25 amino acids in length.

A derivative of the antigen may include a fusion of the antigen, or a fusion of a fragment of the antigen to another compound, and which can be recognized by either a class I or class II MHC molecule when presented on the monocyte-derived dendritic cell. Unless the context indicates otherwise, wherever the term "antigen" is used in the context of an antigen, a derivative as herein defined is included.

The antigen can be delivered to the monocyte-derived dendritic cell via any method known in the art, including, but not limited to, pulsing the cells directly with the antigen, or utilizing a broad variety of antigen delivery vehicles, such as, for example, liposomes, or other vectors known to deliver antigen to cells. In one specific, non-limiting example an antigenic formulation includes about 0.1 μg to about 100 mg, or about 10 μg to about 10 mg of a selected antigen. An antigen preparation can also contain buffers, excipients, and preservatives, amongst other ingredients.

In another embodiment, a monocyte is contacted with 15 kD granulysin and an antigen to produce an antigen-presenting differentiated dendritic cell. The cells are contacted with antigen for a time sufficient to allow the antigen to be internalized, processed, and presented by the monocyte-derived dendritic cell. Accordingly, the present invention also relates to methods for generating enriched populations of mature, antigen-presenting dendritic cells that can function to present antigen to T cells. In one specific non-limiting example, a monocyte is contacted with 15 kD granulysin and an antigen simultaneously. In one example, the monocyte is contacted with a fusion protein including 15 kD granulysin and an antigen. In another embodiment, the monocyte is contacted with a composition including 15 kD granulysin to produce a monocyte-derived dendritic cell, which is subsequently or simultaneously contacted with an antigen to generate a mature antigen presenting dendritic cell.

In one specific, non-limiting example, monocyte-derived dendritic cells are obtained in vitro by culturing monocytes with 15 kD granulysin for about 24 to about 48 hrs. In another specific, non-limiting example, antigen-presenting monocyte-derived dendritic cells are obtained in vitro by culturing monocytes with 15 kD granulysin for about 48 to about 96 hours, and then contacting the monocyte-derived dendritic cells with an antigen for a time sufficient to allow the antigen to be internalized, processed, and presented by the monocyte-derived dendritic cell, thereby producing antigen presenting monocyte-derived dendritic cells. In another example, antigen-presenting monocyte-derived dendritic cells are obtained in vitro by culturing monocytes with a fusion protein including 15 kD granulysin and a target antigen for about 24 to about 72 hours. In another aspect, the monocytes are contacted with 15 kD granulysin in vivo. In a further embodiment the antigen presenting monocyte-derived dendritic cells are incubated with a dendritic cell maturation agent (e.g., LPS) thereby producing mature antigen-presenting dendritic cells.

One of skill in the art can readily identify monocyte-derived dendritic cells and antigen presenting dendritic cells. These techniques include, but are not limited to, analysis of cell morphology, detection of specific antigens present on the cell surface of mature dendritic cells with for example, monoclonal antibodies, or assays for mixed lymphocyte reactions.

In one embodiment, the presence of mature dendritic cells can be confirmed by antibodies specific for various mature dendritic cell surface markers, such as CD83, CD40, CD86 and HLA-DR. Typically, labeled antibodies specifically directed to the marker are used to identify the cell population. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., *Molecular Probes: Handbook of Fluorescent Probes and Research Chemicals* (1992-1994). The metal compounds that can be conjugated to the antibodies include, but are not limited to, ferritin, colloidal gold, and particularly, colloidal superparamagnetic beads.

Mature dendritic cells may also be identified histologically, by assessing nuclear re-organization, vacuole formation, cytoplasmic enlargement, and membrane ruffling. In addition, one of skill in the art can assess typical mature dendritic cell morphology, including stellate shape and/or well defined veils. For example, one of ordinary skill in the art would associate the conversion of a monocyte into a dendritic cell with an increase in total cell size (volume) and an increase in cell granularity, as can be determined by example by flow cytometry or Fluorescence-Activated Cell Sorting (FACS).

Compositions including mature antigen-presenting dendritic cells may be used as vaccines adjuvants to elicit or boost immune responses against antigens. For example, activated, antigen-presenting monocyte-derived dendritic cells can be used as vaccines to inhibit or prevent future infection, or may be used to activate the immune system to treat ongoing diseases, such as cancer. As disclosed herein, it is believed that the expression level of 15 kD granulysin can be used as a correlate of effective immunity in monitoring vaccines and/or that analogs of 15 kD granulysin can be used as therapeutic agents.

Accordingly, the compositions disclosed herein are useful when used in conjunction with vaccines such as, but not limited to, those for treating chronic bacterial infections, e.g. tuberculosis or chronic viral infections such as those associated with herpes simplex 1 virus, herpes simplex 2 virus, human herpes virus 6, measles virus, rubella virus, human immunodeficiency virus (HIV), human T cell leukemia virus I, human T cell leukemia virus II, varicella-zoster virus, hepatitis B virus, hepatitis C virus, hepatitis D virus, human papilloma virus, parvovirus B19, polyomavirus BK, polyomavirus JC, lentivirus, adenovirus, cytomegalovirus, Epstein-Barr virus, and retrovirus.

Specifically, a method of enhancing vaccine efficacy is disclosed. The method includes administering to a subject in need thereof, a therapeutically effective amount of a vaccine and a monocyte-derived dendritic cell produced by contacting a monocyte with an effective amount of 15 kD granulysin. In other aspect, the method further comprises contacting the monocyte with an agent that enhances dendritic cell maturation. In a preferred embodiment, the 15 kD granulysin is substantially free of 9 kD granulysin. In another embodiment, the 15 kD granulysin consists essentially of 15 kD granulysin.

Mature dendritic cells produced by the methods disclosed can also be utilized to produce activated T lymphocytes. The methods disclosed include contacting a monocyte-derived dendritic cell with a T lymphocyte in vitro, thereby producing an activated T lymphocyte. Mature dendritic cells generated by the methods can be administered to a subject. Mature dendritic cells generated by contacting a monocyte with a composition including 15 kD granulysin in vitro can be administered to a subject to preferentially stimulate immune responses which block allergic responses (e.g. interferon production). Thus, the mature dendritic cells generated by 15 kD granulysin treatment may be administered to a subject for treating an allergic condition in that individual. The treatment of allergic conditions is based on the discovery that 15 kD granulysin may stimulate dendritic cells to produce anti-allergic agents, such as IFN-α, which in turn increased the production of IFN-γ by natural killer (NK) cells and T cells.

The mature dendritic cells generated by the methods described can be used for immunotherapy. In one embodiment, the dendritic cells generated by the methods can also be used for tumor immunotherapy. In one embodiment, the mature dendritic cells present a tumor antigen. These dendritic cells can be administered to a subject who has a tumor that expresses the tumor antigen. In another embodiment, the mature dendritic cells expressing a target antigen are administered in conjunction with a chemotherapeutic agent.

In another embodiment, mature dendritic cells produced by contacting a monocyte with 15 kD granulysin are administered to boost an immune response against another antigen. The granulysin and antigen can be administered together, or sequentially but sufficiently close together for the granulysin to enhance an immune response against the antigen, for example to enhance an allospecific T cell response against the antigen. In one specific, non-limiting example, the antigen is from an infectious agent, including but not limited to, an antigen from a bacterium, virus, parasite or fungus. The dendritic cells can be from the same subject (autologous) or can be from a different individual (heterologous).

A method is also disclosed for inducing the differentiation of monocytes in vivo. The method includes administering a therapeutically effective amount of 15 kD granulysin to a subject, thereby inducing differentiation of monocytes into differentiated dendritic cells in the subject. The subject can be a mammal, such as a primate. In one specific, non-limiting example, the subject is a human, however veterinary use is contemplated.

As discussed above, in one embodiment, an agent that enhances dendritic cell maturation is administered in conjunction with 15 kD granulysin. Specific, non-limiting examples of agents that enhance dendritic cell maturation include IL-4 and GM-CSF. In another embodiment, a therapeutically effective amount of 15 kD granulysin is administered in the absence of an agent that enhances dendritic cell maturation. In yet another embodiment, a therapeutically effective amount of 15 kD granulysin is administered to a subject in conjunction with a therapeutically effective amount of an antigen to produce an antigen-presenting differentiated dendritic cell in the subject. In a further embodiment, an antigen can be co-administered with 15 kD granulysin, for example, in a liposome, to trigger antigen uptake and maturation of dendritic cells in vivo and enhance antigen presentation by the dendritic cells to T cells in vivo. Thus, antigen presentation and immunity can be significantly enhanced using the methods described herein. For example, 15 kD granulysin and a target antigen may be co-administered in solution, or in a delivery vehicle, such as a liposome, which would facilitate delivery and uptake of 15 kD granulysin and antigen by the subject's monocytes.

In another embodiment, compositions including 15 kD granulysin and monocytes may be used to treat a subject having cancer. As discussed above, cancer treatments may be based upon the development of anti-tumor vaccines including 15 kD granulysin and a tumor antigen, or 15 kD granulysin and mature tumor antigen-presenting dendritic cells. Without being bound by theory, such vaccines not only elicit anti-tumor antibody production, but also activate natural killer cell lytic activity and antibody dependent cellular cytotoxicity (ADCC). Thus, in the latter case, administration of compositions including 15 kD granulysin and a target antigen stimulate production of tumor specific cytotoxic immune cells in vivo which actively target and kill the cancer cells.

In a further embodiment, compositions including activated T cells can be produced in vitro by, for example, co-culturing the mature antigen-presenting dendritic cells prepared according to the invention, with T cells in vitro. Such compositions are useful in adoptive immunotherapy, such as for the production of antigen-specific cytotoxic T lymphocytes or for generating antigen-specific T helper cells.

As disclosed herein, 15 kD granulysin can be used to generate mature dendritic cells in vivo. Thus, in one embodiment, a therapeutically effective amount of 15 kD granulysin is administered locally, such as to a specific site in a subject in order to activate and expand monocytes at that site. In another embodiment, a therapeutically effective amount of 15 kD granulysin is administered systemically, such as by intravenous, intramuscular, intradermal, intraarterial, parenteral, or subcutaneous injection, or by oral administration or inhalation, to induce differentiation of monocytes into monocyte-derived dendritic cells.

In one embodiment, 15 kD granulysin is administered in a delivery complex. The delivery complex can include 15 kD granulysin and a targeting means. Any suitable targeting means can be used. For example, 15 kD granulysin can be associated with (e.g., ionically or covalently bound to, or encapsulated within) a targeting means (e.g., a molecule that results in higher affinity binding to a target cell, such as a B cell). A variety of coupling or cross-linking agents can be used to form the delivery complex, such as protein A, carbodiamide, and N-succinimidyl-3-(2-pyridyldithio)propionate (SPDP). Examples of a delivery complex include a composition including 15 kD granulysin associated with a sterol (e.g., cholesterol), a lipid (e.g., a cationic lipid, virosome or liposome), and a target cell specific binding agent (e.g., a ligand recognized by target cell specific receptor). Without being bound by theory, the complex is sufficiently stable in vivo to inhibit or prevent significant uncoupling prior to delivery to the target cell, such as a tumor cell. In one embodiment, the delivery complex is cleavable such that 15 kD granulysin is released in a functional form at the target cell.

In another embodiment, 15 kD granulysin is administered in conjunction with a pharmacologically acceptable carrier. Pharmacologically acceptable carriers (e.g., physiologically or pharmaceutically acceptable carriers) are well known in the art. A suitable pharmacological composition can be formulated to facilitate the use of 15 kD granulysin in vivo and/or ex vivo. Such a composition can be suitable for delivery of the active ingredient to any suitable host, such as a patient for medical application, and can be manufactured in a manner that is itself known, e.g., by means of conventional mixing, dissolving, granulating, dragee-making, levigating, emulsifying, encapsulating, entrapping or lyophilizing processes.

Pharmacological compositions for use can be formulated in a conventional manner using one or more pharmacologically (e.g., physiologically or pharmaceutically) acceptable carriers including excipients, as well as optional auxiliaries that facilitate processing of the active compounds into preparations which can be used pharmaceutically. Proper formulation is dependent upon the route of administration chosen, and whether use will be an in vivo or an ex vivo use. For use in vivo, administration can be either systemic or local. In addition, one of skill in the art can readily select a suitable route of administration, including, but not limited to intravenous, intramuscular, intraperitoneal, transmucosal, subcutaneous, transdermal, transnasal, inhalation, and oral administration.

C. Organ Transplantation Rejection

Despite significant advances in understanding of tissue typing and immunosuppression and the availability of better immunosuppressive agents, acute rejection remains a serious clinical problem in organ transplantation. In the absence of successful therapies, organ rejection leads to graft failure in some patients, for example, requiring reinstitution of dialysis and the search for another donor kidney for renal transplant recipients.

The instant disclosure provides a method for detecting and/or monitoring organ transplantation rejection in a transplant recipient including monitoring the level of 15 kD granulysin in a sample obtained from the transplant recipient, wherein a significant increase in the level of 15 kD granulysin in the sample obtained from the transplant recipient (for example, as compared to an earlier or pre-transplantation sample) is associated with organ transplantation rejection.

Also disclosed is a method for inducing tolerance or inhibiting rejection of a cell, tissue, or organ transplant in a transplant recipient including administering to a mammalian transplant recipient a monocyte-derived dendritic cell produced by exposing a monocyte to a composition including 15 kD granulysin and a pharmacological agent, wherein the pharmacological agent is capable of inducing immunological tolerance in the monocyte-derived dendritic cell, and administering to the transplant recipient the immunologically tolerant monocyte-derived dendritic cell, thereby inhibiting rejection of the transplanted cell, tissue or organ. Examples of the types of pharmacological agents that are capable of inducing immunological tolerance in a monocyte-derived dendritic cell include, but is not limited to, cytokines (such as GM-CSF, G-CSF, M-CSF, IL10/TGF-β, IFN-γ, TNF-α, Hepatocyte Growth Factor (HGF), IL-16/TPO, IL-21, IL-10, or Thymic Stromal Lymphopoietin (TSLP)), neuropeptides (such as Vasoactive Intestinal Peptide (VIP), Vitamin D Receptors (VDR) agonists, and Toll-Like Receptor (TLR) agonists (such as LPS).

GM-CSF is known to induce murine semi-mature IL-12 dendritic cells with high expression of MHC class II and co-stimulatory molecules (Gangi et al., *J. Immunol.* 174: 7006-7013, 2005). VIP is a neuropeptide released by immune cells in response to antigen stimulation and a potent anti-inflammatory agent. M-CSF and IL-4 can induce monocyte-derived IL10$^+$, IL12$^{neg}$ tolerogenic dendritic cells (Li et al., *J. Immunol.* 174:4706-4717, 2005). G-CSF indirectly favors the in vitro differentiation of peripheral blood monocytes to tolerogenic dendritic cells through the release of IL-10 and IFN-α (Rutella et al., *Eur. J. Immunol.* 34:1291-1302, 2004). HGF is known to skew monocyte differentiation toward IL-10 producing, co-stimulating tolerogenic dendritic cells (Rutella et al., *Blood* 108:1435-1440, 2006). TSLP is produced by epithelial cells of thymic Hassall's corpuscles. TSLP-released thymic dendritic cells express CD80/CD86 and MHC class II and promote the conversion of thymocytes into regulatory T (Treg) cells (Watanabe et al., *Nature* 436: 1181-1185, 2005).

Other examples of pharmacological agents that are capable of inducing immunological tolerance in monocyte-derived dendritic cells can be found, for example in Rutella et al., (*Blood* 108:1435-1440, 2006) and Silk and Fairchild (*Curr. Opin. Organ. Transpl.* 14:344-350, 2009). In one example, the methods further comprise administering to the mammalian transplant recipient at least one immunosuppressant or anti-inflammatory drug.

D. Autoimmune Disorders

Dendritic cells regulate immune responses that result in two opposite outcomes: immunity or tolerance. The fine regulation of these two distinct functions is not completely understood. However, it is presently believed that the net effect of antigen dose, dendritic cell lineage and maturation status, and dendritic cell stimulation by pathogen derived products, and cytokine milieu at sites of inflammation determine whether an immunogenic or a tolerogenic T cell response will develop. Because dendritic cell-based immunotherapy in autoimmune disease depends on tolerogenic dendritic cells, discerning markers for tolerogenic dendritic cells is a significant objective. For example, immature dendritic cells and IL-10-modified dendritic cells have been observed to mediate immune tolerance by inducing T-cell anergy or T-helper type 2 responses. A variety of pharmacological agents are known to induce tolerogenicity in dendritic cells, in some examples, the induction is attributed to the activity of individual cytokines or neuropeptides. Examples of the types of pharmacological agents that are capable of inducing immunological tolerance in a monocyte-derived dendritic cell include GM-CSF, G-CSF, M-CSF, IL10/TGF-β, IFNγ, TNFα, HGF, IL-16/TPO, IL-21, IL-10, TSLP, VIP, VDR agonists, and TLRs.

Autoimmune diseases comprise a large number of widely varying illnesses. Their common feature is the existence of an immune response in the subject against one or more "self" antigens, including such wide ranging molecules as proteins, DNA and carbohydrates. These diseases can cause symptoms ranging from mild discomfort to debilitation and death. Most of the autoimmune diseases remain enigmatic, not only in their molecular basis, but in their prediction, progression and treatment. Autoimmune diseases include systemic lupus erythematosus, Sjogren's syndrome, rheumatoid arthritis, juvenile onset diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (Type II diabetes), male and female autoimmune infertility, ankylosing spondylitis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, rubulavirus, and Evan's syndrome.

The present invention provides a method for treating the symptoms of an autoimmune disorder. Preferably, the treatment occurs during the presymptomatic or preclinical stage of the autoimmune disorder, and in some cases during the symptomatic stage of the disorder. Early treatment is preferable, in order to reduce, inhibit, or prevent the loss of function associated with inflammatory tissue damage. The presymptomatic, or preclinical stage will be defined as that period not later than when there is T cell involvement at the site of disorder, e.g. islets of Langerhans, synovial tissue, thyroid gland, but the loss of function is not yet severe enough to produce the clinical symptoms indicative of overt disease. T cell involvement may be evidenced by the presence of elevated numbers of T cells at the site of the disorder, the presence of T cells specific for auto-antigens, the release of perforins and granzymes at the site of the disorder, or as a response to immunosuppressive therapy.

For example, degenerative joint diseases can be inflammatory, as with seronegative spondylarthropathies, e.g. ankylosing spondylitis and reactive arthritis; rheumatoid arthritis; gout; and systemic lupus erythematosus. The degenerative joint diseases have a common feature, in that the cartilage of the joint is eroded, eventually exposing the bone surface. Destruction of cartilage begins with the degradation of proteoglycan, mediated by enzymes such as stromelysin and collagenase, resulting in the loss of the ability to resist compressive stress. Alterations in the expression of adhesion molecules, such as CD44, ICAM-1, and extracellular matrix protein, such as fibronectin and tenascin, follow. Eventually fibrous collagens are attacked by metalloproteases, leading to the loss of collagenous microskeleton. At this point, repair by regeneration is no longer possible. There is significant immunological activity within the synovium during the course of inflammatory arthritis. While treatment during early stages is desirable, the adverse symptoms of the autoimmune disorder may be at least partially alleviated by treatment, such as the administration of 15 kD granulysin, during later stages. Clinical indices for the severity of arthritis include pain, swelling, fatigue and morning stiffness, and may be quantitatively monitored by Pannus criteria. Autoimmune disease progression in animal models can be followed by measurement of affected joint inflammation.

The present invention provides a composition and method of treating or inhibiting an immune-based disease in vivo. In one embodiment, a method for treating or ameliorating an autoimmune disease in a subject includes administering a therapeutically effective amount of 15 kD granulysin in vivo to induce differentiation of monocytes in the subject into monocyte-derived dendritic cells, transforming the monocyte-derived dendritic cells to tolerogenic dendritic cells by exposure in vivo to factors that promote tolerogenicity, thereby treating the ongoing autoimmune disease and/or inhibiting its future exacerbation. For example, factors that promote tolerogenicity include, but are not limited to, neuropeptides (such as vasoactive intestinal peptide and pituitary adenylate cyclase-activating polypeptide) (Silk and Fairchild, *Curr. Opin. Organ Transplant.* 14:344-350, 2009), cytokines (such as G-CSF, IL-4, GM-CSF and HGF) (Rutella et al., *Blood* 108:1435-1140, 2006), toll-like receptors (such as LPS), Tryptophan (Trp) metabolites (Brown et al., 1991), and Vitamin D Receptor (VDR) agonists (Adorini and Penna, *Hum. Immunol.* 70:345-352, 2009).

In another embodiment, a method for treating or ameliorating an autoimmune disease in a subject includes removing a monocyte from a subject with an autoimmune disease, and treating the monocyte with 15 kD granulysin to induce differentiation of the monocyte to a monocyte-derived dendritic cell, transforming the monocyte-derived dendritic cell to a tolerogenic dendritic cell by exposure in vitro to factors that promote tolerogenicity, and re-introducing the pre-treated dendritic cell to the subject in order to treat the ongoing autoimmune disease and/or inhibit its future exacerbation. In one example, the methods further include administration of at least one immunosuppressant or anti-inflammatory drug to the subject with the autoimmune disease.

In another embodiment, a method of treating the symptoms of an autoimmune disease include contacting a monocyte with 15 kD granulysin and a target antigen associated with the autoimmune disease in vitro to produce a monocyte-derived dendritic cell expressing the target antigen, transforming the monocyte-derived dendritic cell expressing the target antigen to a tolerogenic dendritic cell expressing the target antigen by exposure in vitro to factors that promote tolerogenicity, and re-introducing the pre-treated dendritic cell expressing the target antigen to the subject in order to treat the symptoms of the autoimmune disease. In some instances, the antigen of interest is a tumor antigen, such as a lung, colon or breast cancer antigen. In another embodiment, the target antigen can be a vaccine, such as a DNA vaccine (e.g., HBV, HPV, or EBV vaccine). In a further embodiment, the antigen of interest is an autoimmune disease antigen, such as an arthritis-induced antigen or a lupus-associated antigen. In another embodiment, the methods further include administering at least one immunosuppressant or anti-inflammatory drug to the subject with the autoimmune disease. In a specific, non limiting example, the autoimmune disease is any one of the conditions described herein.

The disclosure is further illustrated by the following non-limiting Examples.

EXAMPLES

Example 1

Differentiation of Monocytes

Figure 1C:
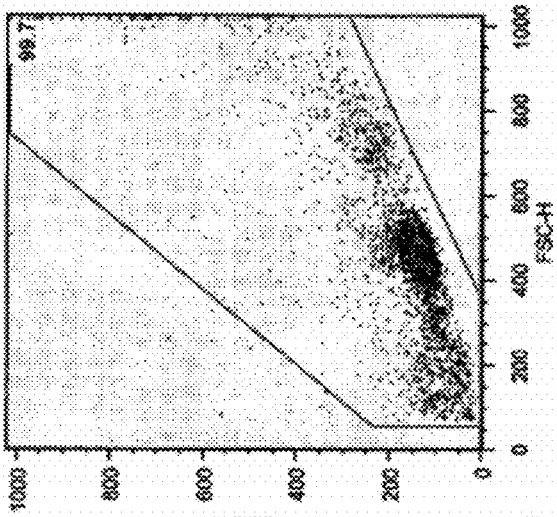
FIG. 1A-1C show flow cytometry data demonstrating the activation activity of 15 kD granulysin (10 nM) on human monocytes in vitro.
Figure 1B:
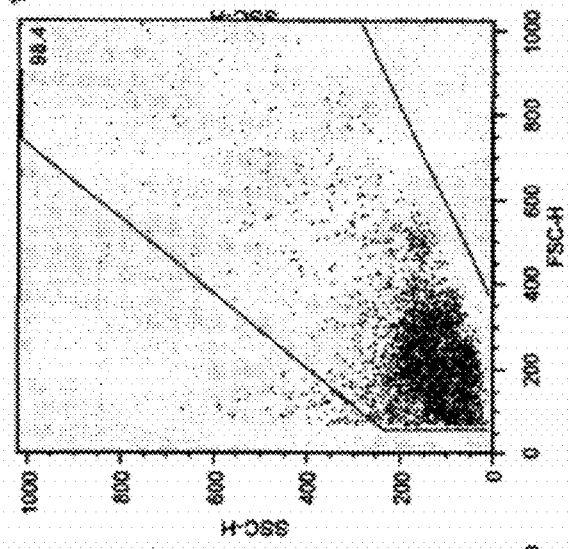
Figure 1A:
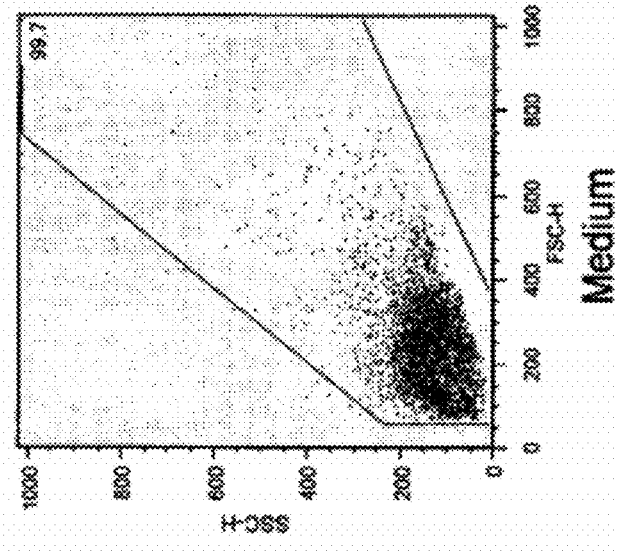

Granulysin 15 kD was found in cell culture studies to induce differentiation of monocytes into monocyte-derived dendritic cells. The results are shown in FIG. 1. CD14+ monocyte cells were isolated from human buffy coats using magnetic beads. Cells were plated at $2\times10^6$/ml in the presence of 15 kD granulysin (10 nM), 9 kD granulysin (10 nM) or cell culture medium for 48 hours. The cells were then analyzed for forward and side scatter by Fluorescence-Activated Cell Sorting (FACS). FIG. 1C shows the effect of treatment in the presence of 15 kD granulysin (10 nM). As noted in FIG. 1C an increase in cell size (x-axis) and an increase in cell granularity (y-axis) was observed, as would be expected following differentiation of monocytes into monocyte-derived dendritic cells. In contrast, the treatment with 9 kD granulysin did not result in an increase in cell size or cell granularity and was comparable to treatment with cell culture medium only, and therefore suggests that 9 kD granulysin does not activate monocytes in vitro.

Example 2

Cell Surface Expression of Activated Monocytes

Dendritic cells can be distinguished from monocytes by their cell surface expression of several markers, for example CD40, CD80 and CD83 (Chapuis et al., *Eur. J. Immunol.* 27:431-441, 1997; Zhou and Tedder, *J. Immunol.* 154:3821-3835, 1995). Monocyte cells were prepared and isolated as described in Example 1, and were subjected to antibody staining for the following cell surface markers: CD40, CD80, CD83, and CD209. The cells were then analyzed by FACS; the results of which are presented in FIG. 2.

Figure 2A:
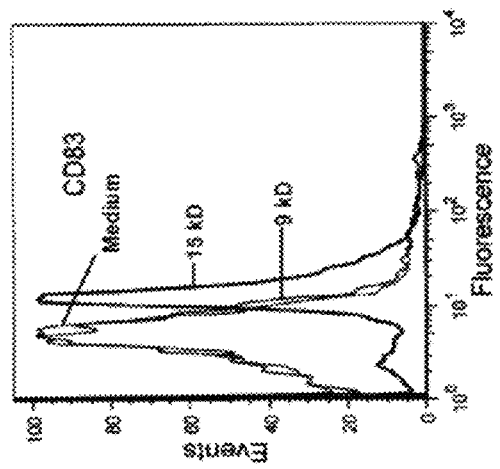
FIG. 2A-2D are graphs of cell surface expression markers of CD14+ human monocytes after 2 days incubation with 15 kD granulysin (10 nM) or 9 kD granulysin (10 nM). Cell surface expression phenotype data is shown for the cell surface markers CD40 (A), CD83 (B), CD80 (C), and CD209 (D). Treatment of human CD14+ monocytes with 15 kD granulysin (10 nM) was found to activate monocytes in vitro as shown by an up-regulation of dendritic cell specific surface markers, CD40, CD80, CD83, and CD209.
Figure 2B:
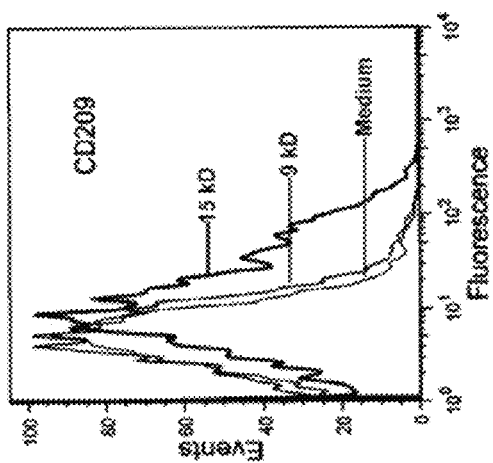
Figure 2C:
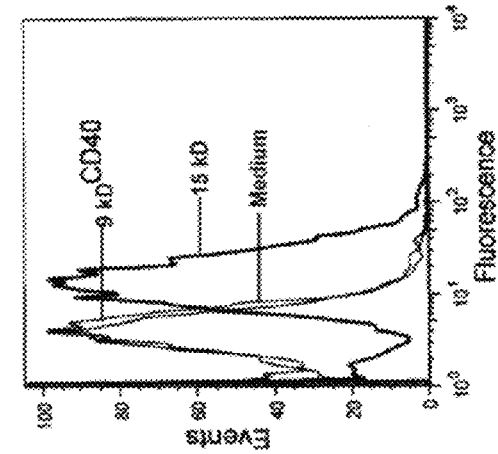
Figure 2D:
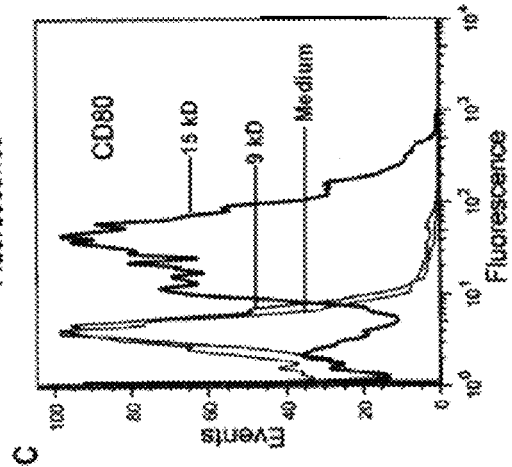
Figure 3A:
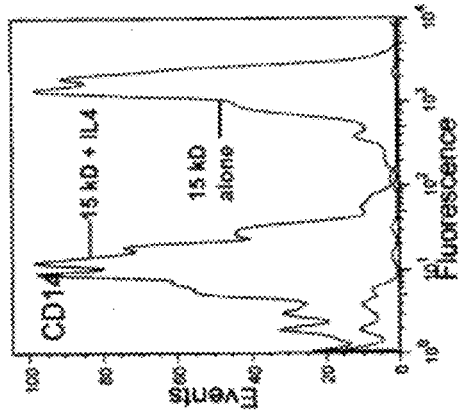
FIG. 3A-3F are graphs of cell surface expression markers of CD14+ human monocytes cultured with 15 kD granulysin (10 nM) and IL-4 for 5 days. Lipopolysaccharide (LPS) was added to the culture on day 5 to induce maturation of resulting monocyte-derived dendritic cells, and the cells were analyzed on day 7 by Fluorescent Activated Cell Sorting (FACS). Cell surface expression phenotype data is shown for the markers CD86 (A), CD209 (B), CD14 (C), CD11b (D), CD80 (E), and HLA-DR (F). Incubation of human CD14+ monocytes in vitro with 15 kD granulysin (10 nM), IL-4 and LPS resulted in the differentiation of monocytes into mature dendritic cells (derived from monocytes) as shown by an up-regulation of dendritic cell specific-surface markers and a down-regulation of monocyte specific cell surface markers (e.g., CD14).
Figure 3B:
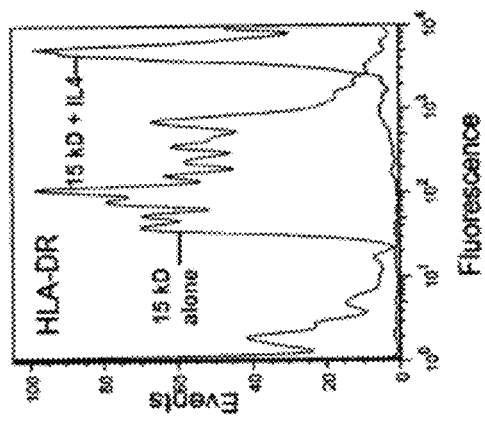
Figure 3C:
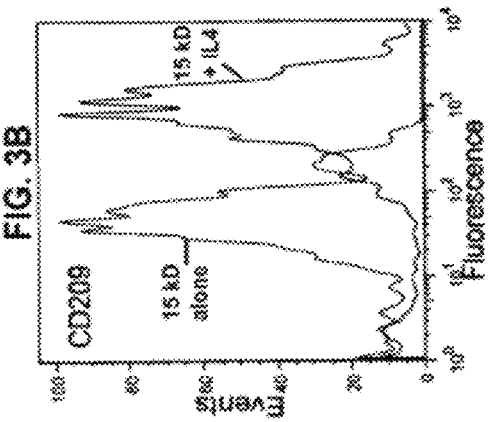
Figure 3D:
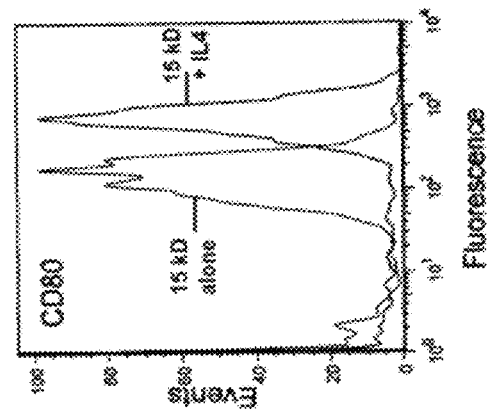
Figure 3E:
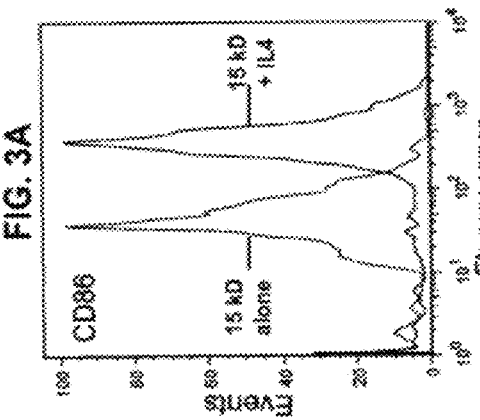
Figure 3F:
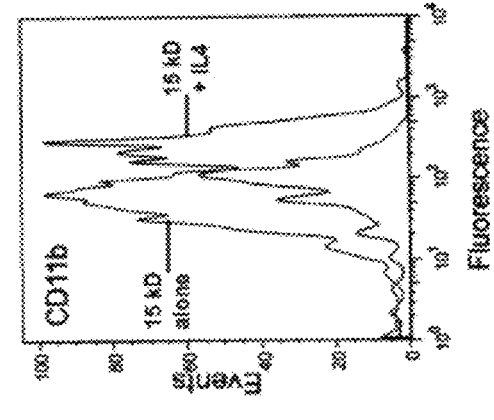
Figure 3G:
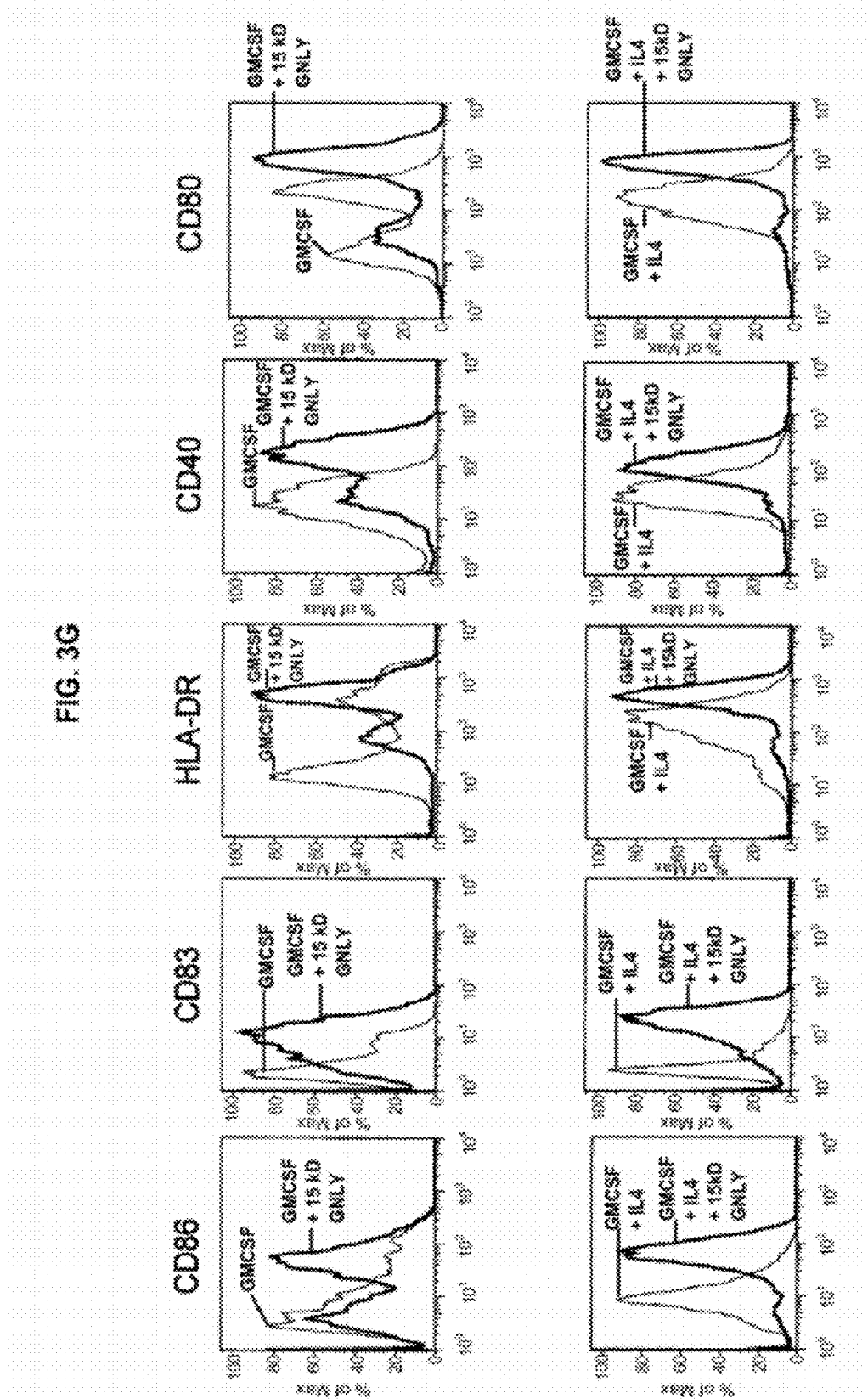
FIG. 3G shows a series graphs of cell surface expression markers that illustrate 15 kD granulysin activates immature dendritic cells to become mature dendritic cells. Elutriated human monocytes ($2\times10^6$/ml) were incubated in RPMI-1640 supplemented with 10% FCS in the presence of GM-CSF (10 ng/ml) and IL-4 (10 ng/ml). After 5 days, 15 kD granulysin (10 nM) was added and the culture continued for an additional 24 hours. Cells were harvested, stained with fluorescent antibodies, and analyzed by FACS.

FIG. 2A discloses the levels of cell surface marker CD40 after culturing with 9 kD granulysin (10 nM) or 15 kD granulysin (10 nM) as compared to cell culture medium (control). Monocytes treated with 15 kD granulysin displayed a significant increase in fluorescence, based on expression of CD40 as compared to 9 kD treated monocytes or the control sample. An increase in fluorescence based expression of cell surface markers CD83 and CD80 was also observed when the monocytes were cultured with 15 kD granulysin for 48 hours prior to FACS analysis. In contrast, monocytes treated with 9 kD granulysin (10 nM) for an equivalent amount of time showed fluorescence profiles similar to the control sample (cell culture medium only). Fluorescence of monocytes treated with 15 kD granulysin (10 nM) as measured by CD209 cell surface expression was also observed to be slightly elevated when compared to monocytes treated with 9 kD granulysin (under identical conditions). Both CD40 and CD80 are co-stimulatory molecules that participate in the process of presenting antigens to T cells; CD83 is a cell surface marker associated with the cell surface of dendritic cells. Thus, the shift in fluorescence as measured by these cell surface markers is indicative of the differentiation of monocytes to monocyte-derived dendritic cells and the ability of the monocyte-derived dendritic cells to process and present antigens.

Example 3

Additional Method for Differentiation of Monocytes into Dendritic Cells

As described in Example 2, dendritic cells can be distinguished from monocytes by the expression of several cell surface markers, for example CD83, CD40 and CD80. In this example, cell culture studies demonstrated that treatment of human CD14+ monocytes with 15 kD granulysin (10 nM) and IL-4 (10 ng/ml) can expeditiously differentiate monocytes into monocyte-derived dendritic cells. The results are shown in FIG. 3.

CD14+ human monocyte cells were isolated from human buffy coats using magnetic beads as disclosed in Example 1. Cells were plated at $2\times10^6$/ml in the presence of 15 kD granulysin (10 nM) and in the presence or absence of human IL-4 (10 ng/ml) for 5 days. After 5 days, 10 ng/ml of the toll-like receptor agonist, lipopolysachharide (LPS) was added and the cells were further incubated for an additional 48 hours. The cells were stained with fluorescent antibodies and analyzed by FACS.

FIG. 3 shows the effect of 15 kD granulysin (10 nM) treatment in combination with IL-4 on the expression of several cell surface markers as measured by florescence. FIGS. 3A, 3B, 3D, 3E and 3F all show a significant up-regulation of fluorescence in cell surface markers CD86, CD209, CD11b, CD80 and HLA-DR, respectively. As already noted in Example 2, the level of fluorescence of CD86 and CD209 was observed to increase upon incubation with 15 kD granulysin over 48 hours. Here, it is observed that the level of fluorescence increased further upon incubation of 15 kD granulysin and IL-4 over a period of 5 days, in combination with LPS. Up-regulation of HLA-DR, CD80, CD11b, CD209, and CD86, and down-regulation of CD14 is consistent with the previously reported phenotype of mature dendritic cells. (Chapuis et al., *Eur. J. Immunol.* 27:431-441, 1997; Zhou and Tedder, J. Immunol. 154:3821-3835, 1995; Shortman and Liu, *Nat. Rev. Immunol.* 2:151-161, 2002).

Example 4

Vaccine Adjuvant Protocol

Cell culture studies on the ability of 15 kD granulysin and IL-4 to act as an immunoactivating composition were studied using conventional methods known in the art. In this example, 15 kD granulysin and IL-4 were co-administered to stimulate differentiation of monocytes.

It is known that monocytes incubated with GM-CSF and IL-4 in vitro result in the production of dendritic cells (Sallusto and Lanzavecchia, *J. Exp. Med.* 179:1109-1118, 1994). This combination protocol utilizing GM-CSF and IL-4 is currently the standard vaccine adjuvant protocol as used by the National Institute of Health (NIH), Bethesda, USA, and has been used in clinical studies as a vaccine adjuvant for sometime (Belardelli et al., *Cancer Res.* 34:3827-3830, 2004). Surprisingly, it was found by the inventors that 15 kD granulysin can be effectively substituted for GM-CSF in the above vaccine adjuvant protocol to provide a therapeutically effective and efficient vaccine adjuvant. Overall, the inventors determined that GM-CSF can be readily substituted by 15 kD granulysin in the vaccination protocol to achieve the same diagnostic and therapeutic effect.

Table 1 shows the results of cell culture studies (CD14+ monocytes) incubated for 4 days with various compositions, stained with fluorescent antibodies and analyzed by FACS analysis. In this example, GM-CSF and IL-4 were used at a concentration of 10 µg/ml. Monocyte cells were isolated and treated as described in Example 1 and subjected to staining and analysis by FACS for the following cell surface markers: CD11b, CD14, CD40, CD80, CD83, CD86, CD209, and HLA-DR. It was observed that the percentage positive cells was significantly elevated in monocyte cells treated with 15 kD granulysin and IL-4, as compared to the control sample (cell culture medium only) or IL-4 treatment Importantly, it was also observed that the percentage positive cells for cell surface markers CD14, CD83 and CD209 upon incubation with 15 kD granulysin and IL-4 treatment were comparable to the percentage positive cells for the cell surface markers CD14, CD83, and CD209 when incubated with GM-CSF and IL-4.

Table 1 also shows that monocytes incubated with 15 kD granulysin and IL-4 had a slightly elevated percentage of positive cells for CD86 as compared to the percentage positive cells after incubation with GM-CSF and IL-4. From this in vitro data it is apparent that the expression of cell surface markers associated with dendritic cells is significantly elevated when monocytes are incubated with 15 kD granulysin and IL-4. It is also apparent from the above results that an immune response can be stimulated following incubation of monocytes with 15 kD granulysin and that this immune response is heightened upon co-incubation with a cytokine, such as IL-4, and a toll-like receptor, such as lipopolysaccharide.

TABLE 1

Immunoactivity of 15 kD granulysin and IL-4

| | Percentage positive cells | | | |
|---|---|---|---|---|
| Antibody | Medium | IL-4 | 15 kD granulysin (25 nM) + IL-4 | GM-CSF + IL-4 |
| HLA-DR | 30 | 38 | 64 | 90 |
| CD40 | 4 | 4 | 24 | 30 |
| CD86 | 22 | 25 | 65 | 50 |
| CD209 | 10 | 46 | 84 | 86 |
| CD83 | 4 | 10 | 20 | 21 |
| CD14 | 21 | 14 | 45 | 47 |
| CD80 | 4 | 5 | 38 | 47 |
| CD11b | 38 | 48 | 48 | 85 |

Example 5

Method of Stimulating an Immune Response to an Antigen

In this example, a subject in need of an enhanced immune response to an antigen, for example a tumor antigen is intravenously or subcutaneously infused, following completion of chemotherapy, with a dendritic cell maturation agent, for example 250 µg/m$^2$/day Leukine™ (a commercially available form of a yeast-expressed recombinant GM-CSF) as described in the Leukine™ package insert (Bayer Health Care Pharmaceuticals, 2007). The subject is simultaneously, or within four days of the Leukine™ infusion, intravenously administered 10 mg/kg of 15 kD granulysin. The administration of 15 kD granulysin and a dendritic cell maturation agent is sufficient to stimulate an immune response against the tumor antigen present in the subject.

Example 6

Treatment of Autoimmune Disease

In this example, monocytes are removed from a subject, for example a subject suffering from an autoimmune disease, e.g., Sjogrens Syndrome or autoimmune pancreatitis. The monocytes are manipulated for example, as described in Example 1, to remove non-monocyte cells from the sample. The isolated and purified monocytes are incubated with a therapeutically effective amount of 15 kD granulysin (and optionally, a therapeutically effective amount of a target antigen associated with the autoimmune disease by which the subject is affected, for example carbonic anhydrase isozyme IV (CA IV)) for a sufficient amount of time to differentiate the isolated monocytes into monocyte-derived dendritic cells (and optionally, a therapeutically effective amount of a dendritic cell maturation agent). The monocyte-derived dendritic cells are further incubated in vitro with an effective amount of a pharmacological agent capable of transforming the monocyte-derived dendritic cells to tolerogenic dendritic cells, such as TNF-α. The resulting tolerogenic dendritic cells are re-introduced to the subject with the autoimmune disease in an amount sufficient to treat the symptoms of the autoimmune disease.

Example 7

Inducing Immunological Tolerance to Organ Transplantation

In this example, monocytes are removed from a subject, for example a subject who is selected to undergo organ transplantation, e.g., kidney transplantation. The monocytes are manipulated for example, as described in Example 1, to remove non-monocyte cells from the sample. The isolated and purified monocytes are incubated with a therapeutically effective amount of 15 kD granulysin for a sufficient amount of time to differentiate the isolated monocytes into monocyte-derived dendritic cells (and optionally, a therapeutically effective amount of a dendritic cell maturation agent). The monocyte-derived dendritic cells are further incubated in vitro with a therapeutically effective amount of a pharmacological agent capable of transforming the monocyte-derived dendritic cells into tolerogenic dendritic cells, such as the neuropeptide, vasoactive intestinal peptide (VIP). The resulting tolerogenic dendritic cells are re-introduced to the subject in an amount sufficient to induce immunological tolerance to the transplanted organ.

Example 8

Treatment of Tumors

In this example, monocytes are removed from a subject, for example a subject diagnosed with, or who is at risk from developing a tumor, e.g., melanoma. The monocytes are manipulated for example, as described in Example 1, to remove non-monocyte cells from the sample. The isolated and purified monocytes are incubated with a therapeutically effective amount of 15 kD granulysin (and optionally, a therapeutically effective amount of a target antigen associated with the tumor the subject has, or is at risk of developing, for example MART-1, MAGE 1 or MAGE 3) for a sufficient amount of time to differentiate the isolated monocytes into monocyte-derived dendritic cells. Optionally, the monocyte-derived dendritic cells are incubated with one or more dendritic cell maturation agents, for example, IL-4 and/or LPS. The monocyte-derived dendritic cells are re-introduced to the subject in an amount sufficient to treat or provide a prophylactic response to the tumor.

Example 9

Treatment of Allergies

In this example, monocytes are removed from a subject, for example a subject diagnosed with an allergy, e.g., dust mite hypersensitivity. The monocytes are manipulated for example, as described in Example 1, to remove non-monocyte cells from the sample. The isolated and purified monocytes are incubated with a therapeutically effective amount of 15 kD granulysin (and optionally, a therapeutically effective amount of a target antigen associated with the allergy, for example *Dermatophagoides pteronyssinus* (Dp)) for a sufficient amount of time to differentiate the isolated monocytes into monocyte-derived dendritic cells expressing the target antigen. Optionally, the monocyte-derived dendritic cells expressing the target antigen are incubated with one or more dendritic cell maturation agents, for example, IL-4 and/or LPS. The monocyte-derived dendritic cells expressing the target antigen are re-introduced to the subject in an amount sufficient to treat or provide a prophylactic response to the allergen.

Example 10

GM-CSF Activates Expression of CD1a in Monocytes

Incubation of human CD14+ monocytes with GM-CSF in the presence (or absence) of IL-4 was found to induce a robust expression of CD1a on the cell surface of the monocytes. However, administration of 15 kD granulysin was found not to activate expression of CD1a on the surface of monocytes. Monocyte cells were prepared and isolated as described in Example 1. Human CD14+ monocytes were incubated with 15 kD granulysin (10 nM) or GM-CSF (10 ng/ml) in the presence or absence of IL-4 (10 ng/ml), and incubated for 5 days; cells were subjected to staining for the cell surface marker CD1a. The cells were analyzed by FACS; the results of which are presented in FIG. 4A and FIG. 4B.

Figure 4B:
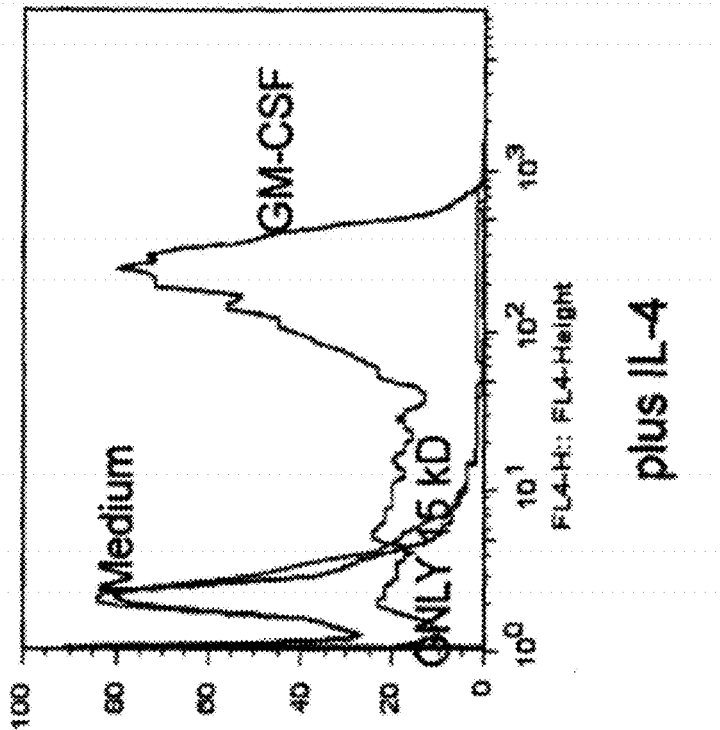
FIG. 4A-4B are graphs of cell surface expression of CD14+ human monocytes cultured with GM-CSF in the presence or absence of IL-4.
Figure 4A:
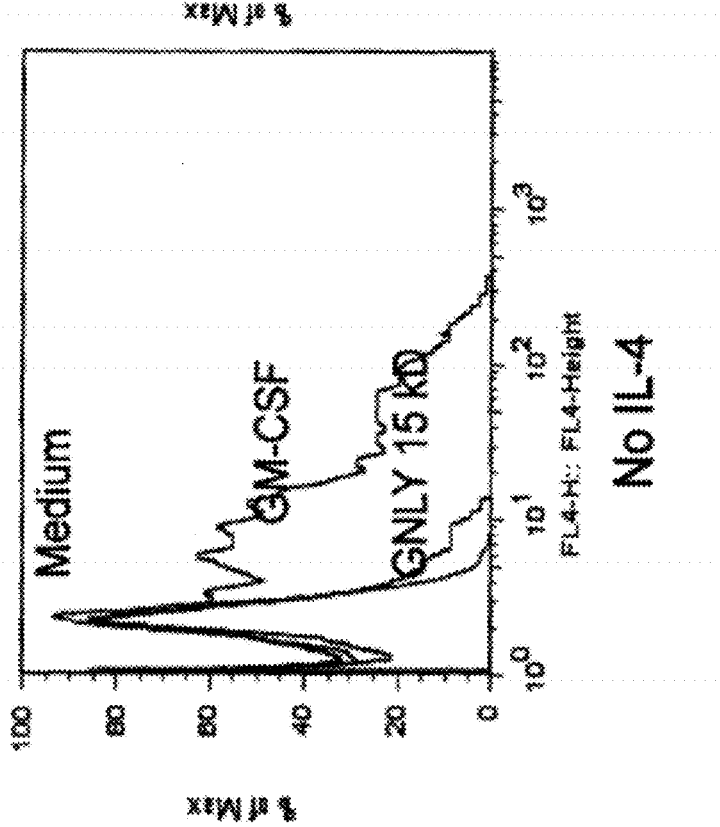

FIG. 4A discloses the level of cell surface marker expression for CD11a after culturing with 15 kD granulysin (10 nM), GM-CSF (10 ng/ml), or as compared to cell culture medium (control). Monocytes treated with 15 kD granulysin displayed a significant decrease in fluorescence based expression of CD1a as compared to GM-CSF treated monocytes. A significant increase in fluorescence based expression of cell surface marker CD1a was observed when the monocytes were cultured with GM-CSF in the presence of IL-4 prior to FACS analysis (FIG. 4B). In contrast, monocytes treated with 15 kD granulysin (10 nM) for an equivalent amount of time showed fluorescence profiles similar to the control sample (culture only) or similar to the expression level observed in FIG. 4A. CD1a is an expression marker predominantly associated with the phenotype of monocytes. Thus, the shift in fluorescence as measured by this cell surface marker in the presence of GM-CSF is indicative of the cells retaining monocyte properties and characteristics. In contrast, the cell surface of human CD14+ monocytes treated with 15 kD granulysin did not appear to be indicative of the cell surface of monocyte cells. In combination with the data from Examples 2 and 3, the data supports the hypothesis that the human CD14+ monocytes in the presence of 15 kD granulysin are activated to become monocyte-derived dendritic cells and thereby expression dendritic cell surface markers.

Example 11

15 kD Granulysin Induces Up-Regulation of Cytokine Expression in Monocytes

Figure 5A:
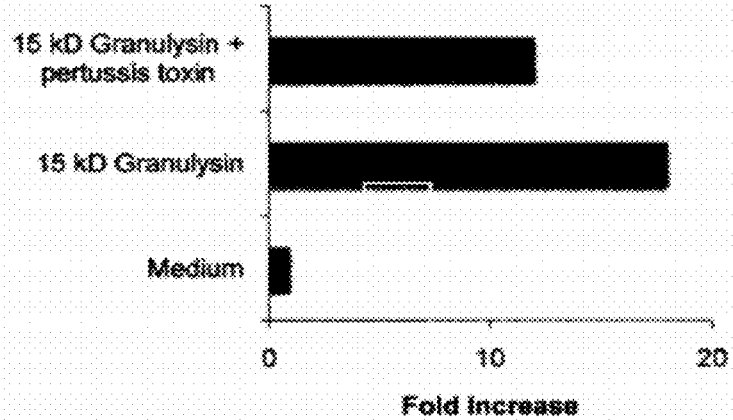
FIG. 5A-5C are graphs demonstrating the fold-increase in cytokine expression (IL-6, IL-1β or TNFα) upon administration of 15 kD granulysin (10 nM) to monocytes in vitro in the presence or absence of an pertussis toxin, an agent that inhibits signaling through G-protein coupled receptors.
Figure 5B:
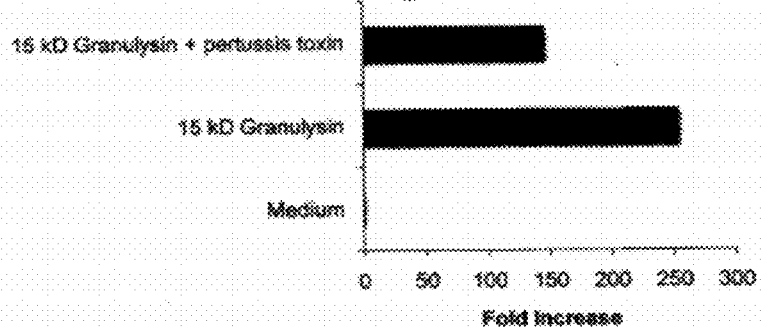
Figure 5C:
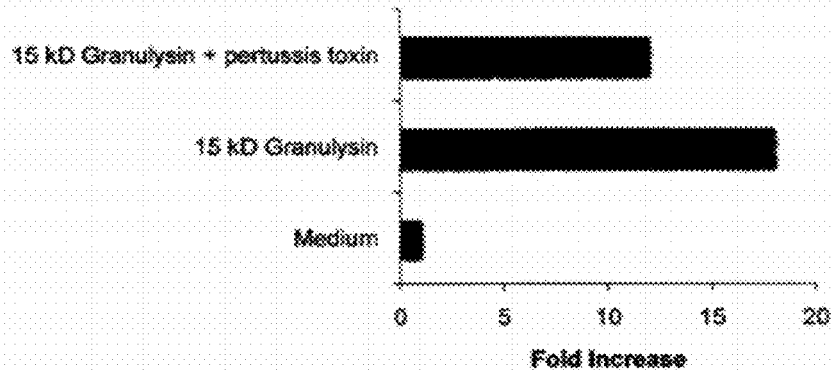

Human CD14+ monocytes incubated in the presence of 15 kD were observed to undergo significant up-regulation and/or expression of TNFα, IL-1β, and IL-6 in vitro. Monocyte cells were prepared and isolated as described in Example 1. Human CD14+ monocytes were incubated in cell culture in the presence of 15 kD granulysin (10 nM) or in the presence of 15 kD granulysin (10 nM) and pertussis toxin (100 ng/ml). The cells were incubated at 37° C. for 4 hours, after which the cells were collected, centrifuged and mRNA obtained. The mRNA obtained from the cultured monocytes was converted to cDNA and quantitative PCR was performed that allowed for the calculation of fold-increase in expression of IL-6, IL-1β, or TNFα, relative to a house-keeping gene (β-glucuronidase (GUS)). FIG. 5A-5C are graphs reporting the fold-increase in cytokine expression of IL-6, IL-1β, or TNFα upon administration of 15 kD granulysin (10 nM) to monocytes in vitro in the presence or absence of an antigen (pertussis toxin). From the data provided in FIG. 5A-5C it was concluded that 15 kD granulysin up-regulates cytokine expression of monocytes in vitro, even in the absence of a target antigen.

Example 12

Activation and Stimulation of Allogeneic T Cells

CD14+ human monocyte cells were isolated from human buffy coats using magnetic beads as disclosed in Example 1. Cells were plated at 2×10$^6$/ml in the presence of 15 kD granulysin (10 nM) or in the presence of GM-CSF (10 ng/ml) and incubated for 4 days. After 4 days, 100 ng/ml of the toll-like receptor agonist, lipopolysachharide (LPS) was added to the cells to induce dendritic cell maturation and the cells were further incubated for an additional two days. On day 6, the cells were harvested and used to stimulate allogeneic T cells. After five additional days, cellular proliferation was measured and reported as fold-stimulation above T-cells alone, the results of which are presented in FIG. 6. The four upper rows of FIG. 6 represent monocytes activated upon incubation with GM-CSF (10 ng/ml) or GM-CSF and IL-4 (10 ng/ml). The four lower rows of FIG. 6 demonstrate fold-stimulation of allospecific T cells upon incubation of human CD14+ monocytes with 15 kD granulysin (10 nM) or 15 kD granulysin and IL-4 (10 ng/ml). The data from FIG. 6 demonstrates that 15 kD granulysin (10 nM) was sufficient to induce a robust stimulation of allogeneic T cells in vitro. Furthermore, the fold-stimulation of allogeneic T cells produced as a result of incubation with 15 kD granulysin (alone), as compared to the level of fold-stimulation induced by GM-CSF (alone), was significantly higher. In contrast, the level of fold-stimulation of allogeneic T cells upon incubation with 15 kD granulysin and IL-4 was substantially reduced as compared to the fold-stimulation effects of 15 kD granulysin alone. Overall, the effect of LPS in these test experiments resulted in an observed decrease of fold-stimulation in allogeneic T cells as compared to the corresponding LPS-free cultures.

Example 13

15 kD Granulysin Activates Monocytes

Many characteristics of 9 kD granulysin are known in the art, including its chemoattractant property. To determine if 15 kD granulysin possesses chemotactic potential, particularly with respect to monocytes, the following experiment was performed. Monocytes are cells of the immune system and in response to inflammatory move to the site of infection where they can divide into dendritic cells or macrophages. The presence of monocytes at the site of infection might be a direct consequence of the properties of 15 kD granulysin in response to inflammation or is perhaps a mechanism by which a shift in the dual-production pathway of macrophages and dendritic cells is converted into a predominantly single pathway, e.g., the production of dendritic cells.

CD14+ human monocyte cells were isolated from human buffy coats using magnetic beads as disclosed in Example 1. Human CD14+ monocytes were cultured for 6 hours at 37° C. in cell culture medium alone, or in cell culture medium supplemented with 15 kD granulysin (10 nM). After 6 hours, cells were visualized using 60× magnification. Monocytes incubated solely in the presence of cell culture medium were dispersed randomly across the visual field and were not observed to aggregate. In contrast, the monocytes incubated in cell culture medium supplemented with 15 kD granulysin were observed to form significant cell clusters.

Example 14

Pharmaceutical Formulations of 15 kD Granulysin

In one embodiment, a therapeutically effective amount of 15 kD granulysin is formulated for administration to the skin. Formulations suitable for topical administration can include dusting powders, ointments, creams, gels, sprays, or transdermal patches for the administration of 15 kD granulysin to cells, such as skin cells. Topical formulations may be administered to blisters or lesions present on the skin, such as leprosy lesions and blisters. In one example, the 15 kD granulysin is administered to the skin for the treatment of melanoma. Alternatively, the 15 kD granulysin is co-administered with a vaccine, for example, an Alzheimer's vaccine, to a host in the form of a transdermal patch. While not wishing to be bound by the following, it is believed that the vaccine and 15 kD granulysin work in combination to activate and/or up-regulate the immune system of the host to recognize a target antigen, such as beta amyloid protein (Aβ) which abnormally accumulates in the brains of Alzheimer's patients. Activation of the subject's immune response following recognition of the target antigen allows the immune system to recognize and inactivate the antigen, thereby reducing or treating the pathology.

The pharmaceutical formulations may optionally include an inorganic pigment, organic pigment, inorganic powder, organic powder, hydrocarbon, silicone, ester, triglyceride, lanolin, wax, cere, animal or vegetable oil, surfactant, polyhydric alcohol, sugar, vitamin, amino acid, antioxidant, free radical scavenger, ultraviolet light blocker, sunscreen agents, preservative, fragrance, thickener, or a combination thereof.

In one example, 15 kD granulysin can be used in cosmetic formulations (e.g., skincare cream, sunscreen, decorative make-up products, and other dermatological compositions) in various pharmaceutical dosage forms, and in the form of oil-in-water or water-in-oil emulsions, solutions, gels, or vesicular dispersions. The cosmetic formulations may take the form of a cream which can be applied either to the face or to the scalp and hair, as well as to the human body, in particular those portions of the body that are chronically exposed to sun or an environmental carcinogen. The cosmetic formulation can also serve as a base for a lip-gloss or lipstick.

In some cosmetic formulations, additives can be included such as, for example, preservatives, bactericides, perfumes, antifoams, dyes, pigments which have a coloring action, surfactants, thickeners, suspending agents, fillers, moisturizers, humectants, fats, oils, waxes or other customary constituents of a cosmetic formulation, such as alcohols, polyols, polymers, foam stabilizers, electrolytes, organic solvents, or silicone derivatives.

Cosmetic formulations typically include a lipid phase and often an aqueous phase. The lipid phase can be chosen from the following group of substances: mineral oils, mineral waxes, such as triglycerides of capric or of caprylic acid, castor oil; fats, waxes and other natural and synthetic fatty substances, esters of fatty acids with alcohols of low C number, for example with isopropanol, propylene glycol or glycerol, or esters of fatty alcohols with alkanoic acids of low C number or with fatty acids; alkyl benzoates; silicone oils, such as dimethylpolysiloxanes, diethylpolysiloxanes, diphenylpolysiloxanes and mixed forms thereof.

If appropriate, the aqueous phase of the formulations according to the present disclosure include alcohols, diols or polyols of low C number and ethers thereof, such as ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, such as silicon dioxide, aluminum silicates, polysaccharides and derivatives thereof, for example hyaluronic acid, xanthan gum and hydroxypropylmethylcellulose, or poly-acrylates.

An exemplary 15 kD granulysin cosmetic formulation is as an additive to a sunscreen composition as a lotion, spray or gel, for administration to the skin. A sunscreen can additionally include at least one further UVA filter and/or at least one further UVB filter and/or at least one inorganic pigment, such as an inorganic micropigment. The UVB filters can be oil-soluble or water-soluble. Oil-soluble UVB filter substances can include, for example: 3-benzylidenecamphor derivatives, such as 3-(4-methylbenzylidene)camphor and 3-benzylidenecamphor; 4-aminobenzoic acid derivatives, such as 2-ethylhexyl 4-(dimethylamino)benzoate and amyl 4-(dimethylamino)benzoate; esters of cinnamic acid, such as 2-ethylhexyl 4-methoxycinnamate and isopentyl 4-methoxycinnamate; derivatives of benzophenone, such as 2-hydroxy-4-methoxybenzophenone, 2-hydroxy-4-methoxy-4'-methylbenzophenone and 2,2'-dihydroxy-4-methoxybenzophenone; esters of benzalmalonic acid, such as di(2-ethylhexyl)-4-methoxybenzalmalonate. Water-soluble UVB filter substances can include the following: salts of 2-phenylbenzimidazole-5-sulphonic acid, such as its sodium, potassium or its triethanolammonium salt, and the sulphonic acid itself; sulphonic acid derivatives of benzophenones, such as 2-hydroxy-4-methoxybenzophenone-5-sulphonic acid and salts thereof; sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)benzenesulphonic acid and salts thereof. The list of further UVB filters mentioned which can be used in combination with 15 kD granulysin according to the disclosure is not intended to be limiting.

For treatment of the skin, a therapeutically effective amount of 15 kD granulysin can be locally administered to an affected area of the skin, such as in the form of an ointment. In one embodiment, the ointment is an entirely homogenous semi-solid external agent with firmness appropriate for easy application to the skin. The ointment can include fats, fatty oils, lanoline, Vaseline, paraffin, wax, hard ointments, resins, plastics, glycols, higher alcohols, glycerol, water, emulsifier or a suspending agent. Using these ingredients as a base, a decoy compound can be evenly mixed. Depending on the base, the mixture can be in the form of an oleaginous ointment, an emulsified ointment, or a water-soluble ointment. Oleaginous ointments use bases such as plant and animal oils and fats, wax, Vaseline and liquid paraffin. Emulsified ointments are comprised of an oleaginous substance and water, emulsified with an emulsifier. They can take either an oil-in-water form (O/W) or a water-in-oil-form (W/O). The oil-in-water form (O/W) can be a hydrophilic ointment. The water-in-oil form (W/O) initially lacks an aqueous phase and can include hydrophilic Vaseline and purified lanoline, or it can contain a water-absorption ointment (including an aqueous phase) and hydrated lanoline. A water-soluble ointment can contain a completely water-soluble Macrogol base as its main ingredient. Alternatively, the 15 kD granulysin can be administered as a transdermal patch that can deliver sustained therapeutic levels of 15 kD granulysin through the skin in a convenient, painless manner, for example, using the PassPort Transdermal System™ developed by Altea Therapeutics (Atlanta, Ga.). In a further embodiment, the 15 kD granulysin transdermal patch may include one or more therapeutic compounds, for example, a vaccine, a drug (such as a chemotherapeutic drug), an anti-inflammatory compound, or other therapeutic agent.

In other embodiments, the 15 kD granulysin can be formulated in an aqueous solution, preferably in a physiologically compatible buffer. For transmucosal administration, penetrants appropriate to the barrier to be permeated are used in the formulation. Such penetrants are generally known in the art. For oral administration, 15 kD granulysin can be combined with carriers suitable for inclusion into tablets, pills, dragees, capsules, caplets, liquids, gels, syrups, slurries, suspensions and the like. The 15 kD granulysin can also be formulated for use in inhalation therapy. For administration by inhalation, 15 kD granulysin is conveniently delivered in the form of an aerosol spray presentation from pressurized packs or a nebulizer, with the use of a suitable propellant. The 15 kD granulysin can be formulated for parenteral administration by injection, e.g., by bolus injection or continuous infusion. Similarly, a composition including 15 kD granulysin can be formulated for intratracheal or for inhalation administration. Such compositions can take such forms as suspensions, solutions or emulsions in oily or aqueous vehicles, and can contain formulatory agents such as suspending, stabilizing and/or dispersing agents. Other pharmacological excipients are known in the art.

In one embodiment, 15 kD granulysin is applied with, or as part of a composition including a pharmaceutically acceptable carrier, diluent or excipient (including combinations thereof). The carrier, diluent or excipient must be "acceptable" in the sense of being compatible with the composition of the invention and not deleterious to the recipient thereof. Typically, the carriers will be water or saline which will be sterile and pyrogen free. Acceptable carriers or diluents for therapeutic use are well known in the pharmaceutical art, and are described, for example, in *Remington: The Science and Practice of Pharmacy*, The University of the Sciences in Philadelphia, Editor, Lippincott, Williams, & Wilkins, Philadelphia, Pa., 21$^{st}$ Edition (2005). The choice of pharmaceutical carrier, excipient or diluent can be selected with regard to the intended route of administration and standard pharmaceutical practice. The pharmaceutical composition may comprise as, or in addition to, the carrier, excipient or diluent any suitable binder, lubricant, suspending agent, coating agent, solubilizing agent or combinations thereof.

Pharmaceutically acceptable carriers include a petroleum jelly, such as VASELINE®, wherein the petroleum jelly contains 5% stearyl alcohol, or petroleum jelly alone, or petroleum jelly containing liquid paraffin. Such carriers enable pharmaceutical compositions to be prescribed in forms appropriate for consumption, such as tablets, pills, sugar-coated agents, capsules, liquid preparations, caplets, gels, ointments, syrups, slurries, and suspensions. When locally administered to cells in an affected area or tissue of interest, the 15 kD granulysin composition can be administered in a formulation that contains a synthetic or natural hydrophilic polymer as the carrier. Examples of such polymers include hydroxypropyl cellulose and polyethylene glycol. The composition can be mixed with a hydrophilic polymer in an appropriate solvent. The solvent is then removed by methods such as air-drying, and the remainder is then shaped into a desired form (for example, a sheet) and applied to the target site. Formulations containing such hydrophilic polymers keep well as they have a low water-content. At the time of use, the formulation absorbs water, becoming a gel that also stores well. In the case of sheets, the firmness can be adjusted by mixing a polyhydric alcohol with a hydrophilic polymer similar to those above, such as cellulose, starch and its derivatives, or synthetic polymeric compounds. Accordingly, a therapeutically effective amount of 15 kD granulysin can be incorporated into bandages, plasters, transdermal patches or other wound dressings.

Example 15

Modes of Administration of 15 kD Granulysin

According to the disclosed methods, compositions of the present invention can be administered by, but not limited to, intramuscular (i.m.), intravenously (i.v.), subcutaneous (s.c.), or intrapulmonary routes. Transdermal delivery includes, but is not limited to intradermal (e.g., into the dermis or epidermis), transdermal (e.g., percutaneous) and transmucosal administration (e.g., into or through skin or mucosal tissue). Intracavity administration includes oral, nasal, peritoneal, rectal, vaginal or intestinal cavities as well as, intrathecal, intraventricular, intraarterial and sub arachnoid administration.

Any mode of administration is contemplated so long as the mode results in the activation of an immune response to the target antigen, in the desired tissue, in an amount sufficient to generate a therapeutically or prophylactically effective immune response against the target antigen.

Determining an effective amount of the composition depends on a number of factors including, for example, the antigen being expressed or administered directly, the age and weight of the subject, the precise condition requiring treatment, the severity of the condition, and the route of administration. Based on the above factors, determining the precise amount, number of doses, and timing of doses are within the ordinary skill in the art and will be readily determined by the attending physician or veterinarian.

The 15 kD granulysin can be formulated for administration by inhalation, such as, but not limited to, formulations for the treatment of lung or esophageal cancer. Inhalational preparations include aerosols, particulates, and the like. In general, the goal for particle size for inhalation is about 1 µm or less in order that the composition reaches the alveolar region of the lung for absorption. However, the particle size can be modified to adjust the region of disposition in the lung. Thus, larger particles can be utilized (such as about 1 to about 5 µm in diameter) to achieve deposition in the respiratory bronchioles and air spaces. In addition, oral formulations may be liquid (e.g., syrups, solutions, or suspensions), or solid (e.g., powders, pills, tablets, caplets, or capsules).

For administration by inhalation, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the composition and a suitable powder base such as lactose or starch.

When 15 kD granulysin is provided as a parenteral composition, e.g. for injection or infusion, it is generally suspended in an aqueous carrier, for example, as an isotonic buffer solution at a pH of about 3.0 to about 8.0, preferably at a pH of about 3.5 to about 7.4, more preferably at about 3.5 to about 6.0, or most preferably between about 3.5 and about 5.0. Useful buffers include sodium citrate-citric acid and sodium phosphate-phosphoric acid, and sodium acetate-acetic acid buffers. A form of repository or "depot" slow release preparations may also be used so that therapeutically effective amounts of 15 kD granulysin are delivered into the blood vessels over many hours or days following transdermal administration or delivery.

The 15 kD granulysin composition can be administered as a sustained-release system, for example of sustained-release compositions including suitable polymeric materials (such as, for example, semi-permeable polymer matrices in the form of shaped articles, e.g., films, or mirocapsules), suitable hydrophobic materials (such as, for example, an emulsion in an acceptable oil) or ion exchange resins, and sparingly soluble derivatives (such as, for example, a sparingly soluble salt). Sustained-release compositions as described herein may be administered orally, rectally, parenterally, intravaginally, intraperitoneally, topically (as by powders, ointments, gels, drops or transdermal patch), bucally, or as an oral or nasal spray.

Preparations for administration can be suitably formulated to give controlled release of 15 kD granulysin over an extended period of time. For example, the pharmaceutical composition may be in the form of particles including a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of an active ingredient, as described in U.S. Pat. No. 5,700,486.

For oral administration, the pharmaceutical composition including 15 kD granulysin can take the form of, for example, tablets or capsules prepared by conventional means with pharmaceutically acceptable excipients such as binding agents (for example, pregelatinized maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulfate). The tablets can be coated by methods well known in the art. In some instances, the disclosed compositions may be microencapsulated (e.g., poly (DL lactide-coglycolide) to reduce or prevent significant degradation of the composition prior to reaching the small intestine. Indeed, oral immunization with antigen incorporated in microparticles has been demonstrated to induce systemic and secretory antibody responses (Eldridge et al., *Curr. Top. Microbiol. Immunol.* 146:59-66, 1989; Challacombe et al., *Immunol.* 76:164-168, 1992). Actual methods of preparing such dosage forms are known, or will be apparent, to those of ordinary skill in the art.

The pharmaceutically acceptable carrier and excipient useful in this invention are conventional. For instance, parenteral formulations usually comprise injectable fluids that are pharmaceutically and physiologically acceptable such as water, physiological saline, other balanced salt solutions, aqueous dextrose, glycerol or the like. If desired, the pharmaceutical composition may also contain minor amounts of non-toxic auxiliary substances, such as wetting or emulsifying agents, preservatives, pH buffering agents, and the like, for example sodium acetate or sorbitan monolaurate. Actual methods of preparing such dosage forms are known, or will be apparent, to those skilled in the art.

Generally, the formulations are prepared by contacting 15 kD granulysin uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Compositions of the present invention may include various excipients, carriers and/or delivery vehicles as are disclosed, e.g., in U.S. Patent Application No. 2002/0019358, published Feb. 14, 2002, which is incorporated herein by reference to the extent it discloses such compositions.

The 15 kD granulysin pharmaceutical composition can be formulated in unit dosage forms suitable for individual administration of precise dosages. The amount administered will be dependent on the subject being treated, the severity of the condition or disorder, and the manner of administration, and is best left to the judgment of the prescribing clinician. Within these bounds, the formulation to be administered will contain a quantity of 15 kD granulysin in an amount effective to achieve the desired effect in the subject being treated. In some incidences, multiple treatments are envisioned, such as over a defined interval of time, for example as daily, bi-weekly, weekly, bi-monthly or monthly administration, such that chronic administration is achieved. As disclosed herein, a therapeutically effective amount of 15 kD granulysin can be used to inhibit the formation of a tumor, treat a tumor, inhibit conversion of a benign tumor to a malignant tumor, decrease the risk of developing a tumor, or inhibit metastasis. Administration of the 15 kD granulysin composition may begin whenever the suppression or inhibition of disease is desired, for example, at a certain age of a subject, or prior to an environmental exposure.

Example 16

Comparison of 15 kD Granulysin and GM-CSF In Vitro

Expression and Purification of 15 kD Granulysin:

A cDNA clone of 15 kD granulysin was generated from human peripheral blood and cloned into pet28A E. coli expression vector. A baculovirus GP67 secretion leader was engineered at the 5' end of the granulysin gene by adapter PCR. The verified clone was subcloned by Gateway LR recombination (Invitrogen, Carlsbad, Calif.) into pDest-670 for insect cell expression. The expression clone was then transformed in to E. coli DH10Bac (Invitrogen), and plated on LB medium containing kanamycin, gentamycin, tetracycline, X-gal, and IPTG as per manufacturer's protocols. The bacmid DNA was verified by PCR amplification across the bacmid junctions and transfected into SF-9 insect cells to create the recombinant baculovirus. Large scale expression was done using Hi5 insect cells grown in 3L Erlenmeyer flasks. Cells were infected at a multiplicity of infection of three, maintained at 27° C. for 4 hours, then shifted to 21° C. and allowed to grow for 48 hours. Cells were spun out and the supernatant containing the secreted 15 kD granulysin was filtered using a 0.45 µM filter and stored at −20° C. This material was applied to a 5 ml HiTrap™ Heparin HP (GE Health Care, Uppsala, Sweden). Fractions containing the 15 kD granulysin were pooled, buffer exchanged, and run on a 1 ml Resource S column (GE Health Care). The purified protein was concentrated and stored at −80° C. Finn et al., Protein Expr. Purif. doi:10.1016/j.pep.2010.07.009, 2010.

Activation of Monocytes and Flow Cytometry:

Elutriated human monocytes were cultured at $2\times10^6$ cells/ml in 24 well plates in RPMI-1640 supplemented with 10% heat-inactivated FBS (Hyclone, Ogden, Utah), 2 mM L-glutamine, and 100 U/ml penicillin-streptomycin (complete medium). 15 kD granulysin (10 nM), GM-CSF (10 ng/ml), and IL-4 (10 ng/ml) were added as described. Cells were stained with the following antibodies from BD Bioscience (San Diego, Calif.): CD86 (clone FUN-1) and CD83 (HB15e) as fluorescein isothiocyanate (FITC) conjugates; CD14 (M5E2), CD80 (L307.4), and CD209 (DCN46) as phycoerythrin (PE) conjugates; CD11c (Bly6), CD11b (ICRF44), CD40 (5C3), and CD1a (HI149) as APC conjugates; and from eBiosciences (San Diego, Calif.) CD1c (L161) FITC conjugate and HLA-DR (L243) as PE conjugates. In some cases, cells were then fixed and permeabilized using BD Cytofix/Cytoperm™ and then stained with antibodies specific for IL-6 (MQ2-6A3) PE conjugate, TNF (MAb11) AF488 conjugate, interferon-γ (B27) PeCy7 conjugate (all from BD Biosciences) or IL1β (CRM56) FITC conjugate from eBiosciences. Flow cytometry data was analyzed with FlowJo analysis software (Tree Star, Ashland, Oreg.).

Using elutriated CD14+ monocytes, the effects of 15 kD granulysin and GM-CSF, a well-characterized activator of monocytes, were compared (FIG. 8). Within 6 hours, monocytes cultured with 10 nM 15 kD granulysin, but not with 10 ng/ml GM-CSF, formed aggregates (FIG. 8A). Both 15 kD granulysin and GM-CSF caused an increase in cell size and upregulation of adhesion molecules including CD11b, CD11c, and CD54, as well as molecules associated with differentiation to immature dendritic cells, including CD40, CD80, CD86 and HLA-DR (FIG. 8B). 15 kD granulysin, but not GM-CSF, promoted increased expression of CD83 while GM-CSF, but not 15 kD granulysin, caused increased expression of CD1a and CD1c. 15 kD granulysin, but not GM-CSF, also caused a rapid increase in expression of IL-1β, IL-6, and TNFα in monocytes (FIG. 8C).

Of note, 15 kD granulysin also activated immature dendritic cells. Monocytes cultured with GM-CSF plus IL-4 for 4 days and then treated with 15 kD granulysin for another 24 hours expressed even higher levels of CD40, CD80, CD83, CD86, and HLA-DR, characteristic of mature dendritic cells (FIG. 9A). The stimulatory capabilities of dendritic cells generated with 15 kD granulysin were evaluated in two ways: (1) proliferation was increased 60-fold when T cells were incubated with allogeneic dendritic cells activated by 15 kD granulysin and (2) coculture of allogeneic T cells with 15 kD activated mature dendritic cells resulted in T cells producing TNFα and IFNγ, but not IL-6 or IL-4, suggesting that 15 kD granulysin induced dendritic cells to a state that favored Th1 over Th2 or Th17 T cell differentiation (FIG. 9B).

Example 17

Effect of 15 kD Granulysin on Monocyte Gene Expression

Because the dendritic cells generated from monocytes in vitro using 15 kD granulysin differ in some ways from those dendritic cells generated with GM-CSF (Example 16, above), microarrays were used to compare the effects of 15 kD granulysin and GM-CSF on gene expression in human monocytes.

Total RNA was extracted using Trizol (Invitrogen, Carlsbad, Calif.) from elutriated monocytes cultured as described in Example 16. RNA integrity was assessed using an Agilent 2100 Bioanalyser (Agilent Technologies, Waldbronn, Germany). Test samples (500 ng) and Universal Reference tRNA (500 ng, Invitrogen) were processed using an Agilent kit, labeled with Cy5 and Cy3, respectively, and co-hybridized according to the manufacturer's instructions on Agilent Chips (Agilent Technologies, Whole Human genome, 4X44k). Microarray image analysis was performed using Agilent Feature Extraction Software 9.5.1.1. The resulting normalized data were uploaded on mAdb Gateway (madb.nci.nih.gov) and further analyzed using BRB Array Tools (linus.nci.nih.gov/BRB-ArrayTools.html), which was developed at the National Cancer Institute (NCI), Biometric Research Branch, Division of Cancer Treatment and Diagnosis (Simon et al., Cancer Inform. 3, Feb. 4, 2007). The data set was filtered according to a standard procedure to exclude spots below a minimum intensity that was set to an arbitrary intensity parameter of 20 in both fluorescence channels. Of these, 33,757 genes passed the filter and were used for further analysis. Hierarchical cluster analysis and TreeView software were used for visualization of the data (http://rana.lbl.gov; Eisen et al., Proc. Natl. Acad. Sci. USA 95:14863, 1998). Class comparison analysis was conducted at a p-value<0.001, random variance model and univariate permutation tests were included to strengthen the analysis.

Global gene expression was assessed pre-treatment (time 0) and after 4, 12, 24 and 48 hours of treatment with either 10 ng/ml GM-CSF or 10 nM 15 kD granulysin in monocytes obtained from 3 subjects. 6103 genes were statistically differentially expressed and showed similar patterns of expression by monocytes treated with either GM-CSF or 15 kD granulysin (p-value<0.001) when compared to their expression levels in pre-treatment monocytes. However, a direct comparison between GM-CSF and granulysin treated monocytes at each time point showed a total of 3690 genes differentially expressed (p-value<0.001) between the two treatments. Of these, the expression of 1815 genes was greater in 15 kD granulysin treated monocytes while expression of 1875 genes was greater in monocytes treated with GM-CSF.

Chemokine/cytokine and costimulatory/adhesion genes induced by 15 kD granulysin were selected for further analysis. Genes that increased in expression at least 5-fold in the microarray analysis were selected and their mRNA levels were determined by real time qPCR. Elutriated monocytes were cultured with 10 nM 15 kD granulysin or 10 ng/ml GM-CSF as in Example 16 and cells were harvested at 4, 12 and 24 hours and frozen. RNA was prepared using an RNeasy® MiniKit and Qiashredder columns (Qiagen, Valencia, Calif.). cDNA was generated using the iScript™ cDNA Synthesis kit (BioRad, Hercules, Calif.) using the manufacturer's suggested protocol. rtPCR reactions were set up in 384 well plates (Applied Biosystems, Foster City, Calif.) in a final reaction volume of 10 µl. The reaction contained the Power SyBR® Green PCR Master Mix (Applied Biosystems). PCR was conducted using a 7900HT Fast Real-Time PCR System (Applied Biosystems) and data were analyzed using SDS 2.3 software package (Applied Biosystems). GUS was used as the control gene for each time point.

As shown in Table 2, mRNA for all these genes was increased over levels in cells cultured in medium alone. In contrast, at the four-hour time point, only CD274 and CD80 were slightly upregulated in monocytes cultured with GM-CSF. At 4, 12 and 24 hours, the majority of these genes were expressed at much higher levels in cells treated with 15 kD granulysin than in those treated with GM-CSF. Protein expression was also confirmed for a subset of these genes. At 24 hours, monocytes cultured with 15 kD granulysin expressed abundant levels of IL-1β, IL-6 and TNFα while cells cultured with GM-CSF did not express these cytokines (Table 2). These data indicate that 15 kD granulysin affects monocytes differently from GM-CSF, suggesting that 15 kD granulysin may be a useful alternative for production of antigen presenting cells for adoptive cell based therapies.

TABLE 2

Immune-related gene expression in monocytes activated by 15 kD granulysin or GMCSF

| | 15 kD Granulysin | | | GM-CSF | | |
|---|---|---|---|---|---|---|
| | 4 hour | 12 hour | 24 hour | 4 hour | 12 hour | 24 hour |
| IL-6 | 2802 | 3308 | 940 | 1 | 3 | 2 |
| CCL20 | 243 | 375 | 1056 | 0 | 1 | 1 |
| TNFAIP6 | 62 | 100 | 31 | 2 | 1 | 0 |
| CXCL1 | 66 | 131 | 16 | 1 | 2 | 0 |
| ITGB8 | 124 | 220 | 36 | 2 | 1 | 0 |
| TNFAIP8 | 22 | 5 | 5 | 3 | 1 | 1 |
| TNF | 35 | 31 | 6 | 1 | 3 | 3 |
| CXCL2 | 19 | 81 | 51 | 1 | 3 | 1 |
| TRAF1 | 20 | 21 | 5 | 1 | 1 | 0 |
| CXCL3 | 16 | 83 | 41 | 1 | 1 | 1 |
| IL7R | 8 | 23 | 8 | 2 | 2 | 4 |
| ADAMDECH1 | 4 | 22 | 8 | 1 | 1 | 0 |
| TNFRSF4 | 11 | 24 | 2 | 1 | 3 | 1 |
| CD274 | 319 | 102 | 12 | 11 | 7 | 2 |
| CD80 | 35 | 42 | 21 | 6 | 17 | 17 |
| SPP1 | 7 | 23 | 16 | 2 | 12 | 26 |
| IL1B | 70 | 206 | 248 | 1 | 6 | 8 |
| CCL23 | 350 | 1013 | 311 | 2 | 7 | 143 |
| MMP14 | 158 | 194 | 55 | 1 | 1 | 5 |
| CCL2 | 731 | 48 | 8 | 1 | 2 | 43 |
| CCL7 | 79 | 19 | 8 | 1 | 1 | 18 |

Example 18

Effect of 15 kD Granulysin Expression on Tumors In Vivo

To further investigate a role for 15 kD granulysin in clinical situations, a mouse model was utilized. Mice do not have a granulysin homologue, however, mice transgenic for human granulysin have been generated (Huang et al., J. Immunol. 178:77-84, 2007). It was previously shown that allospecific T cell lines generated from granulysin transgenic animals showed enhanced killing of target cells. In vivo effects of granulysin have been evaluated using the syngeneic T lymphoma tumor C6VL. Granulysin transgenic mice survived significantly longer than nontransgenic littermates in response to a lethal tumor challenge (Huang et al., J. Immunol. 178:77-84, 2007). These findings demonstrated for the first time an in vivo effect of granulysin. To build upon these results in another model with a different strain, C57BL/6 GNLY$^{+/-}$ animals were crossed onto Balb/c mice.

WT and GNLY$_{+/-}$ mice were injected in the right flank with $1.5 \times 10^6$ CT26 tumor cells. After 12-14 days, tumors were removed and weighed. Flow cytometry was performed using the following antibodies from BD Biosciences: FITC-conjugated CD3 (145-2C11), CD4 (L3T4), CD8 (53-6.7); PE-conjugated CD40 (3/23) and CD86 (GL1); APC-conjugated interferon-γ (XMG1.2) and TNF (MP6-XT22). Tumor infiltrating lymphocytes (TIL) and lymphocytes from the draining inguinal and popliteal lymph nodes were prepared and analyzed for expression of CD40 and CD86. TIL were also subjected to intracellular staining for TNFα and IFNγ following in vitro stimulation with PMA and ionomycin in the presence of GolgiStop™ (BD Biosciences).

Figures 10A, 10B, 10C:
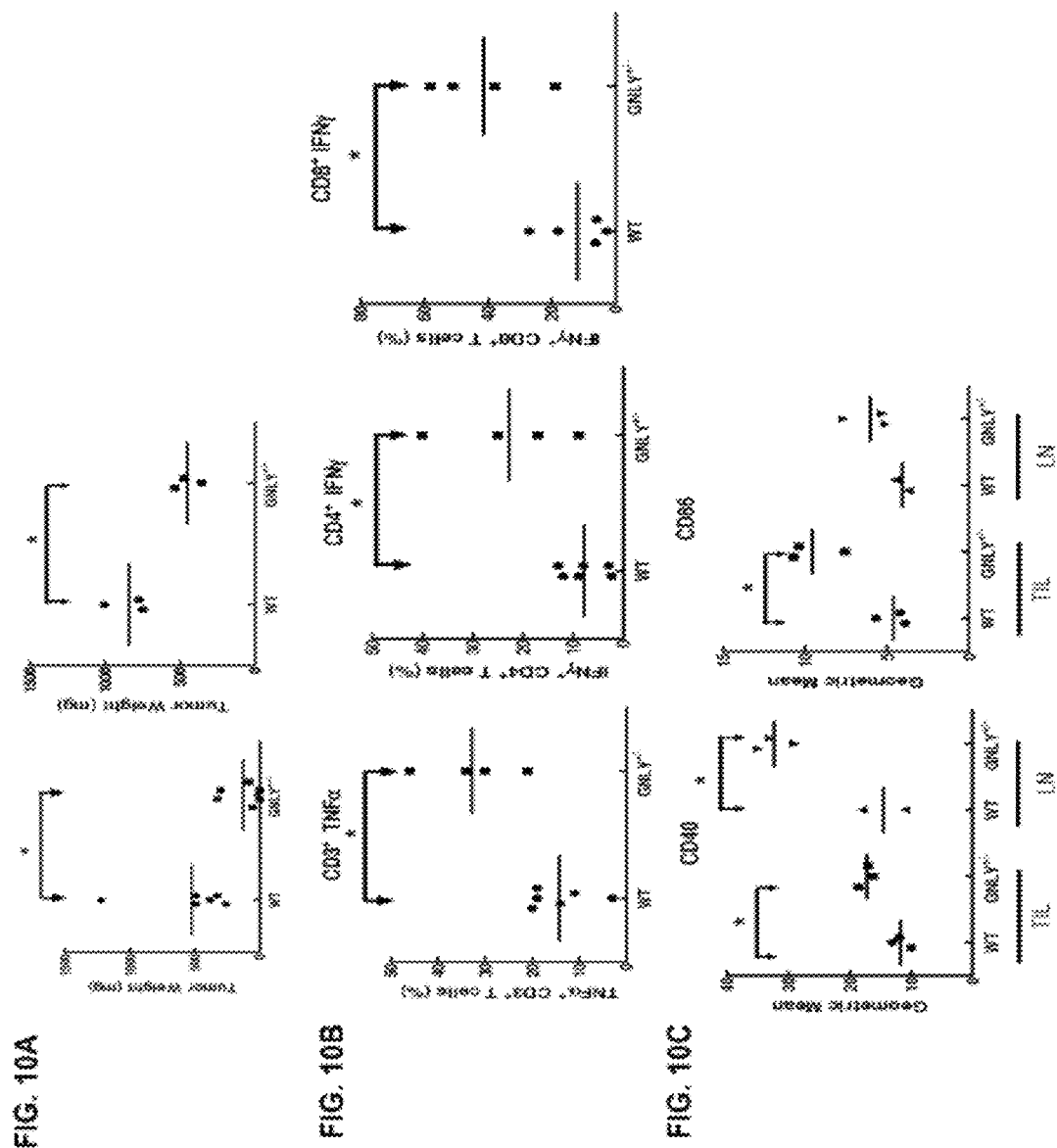
FIG. 10B shows the percentage of the indicated cells after stimulation of tumor infiltrating lymphocytes (TIL) stimulated in vitro with PMA/ionomycin. Expression of TNFα and IFNγ was measured by flow cytometry. $*p<0.01$
FIG. 10C shows the numbers of CD40+ and CD86+ cells in the tumor (TIL) and draining lymph nodes (LN). $*p<0.01$

After >10 backcrosses, the animals were challenged with the syngeneic CT26 colon carcinoma (Wu et al., *Med. Oncol.* 27:736-742, 2010). Tumors from both wild type and transgenic mice were removed at various times and tumor-infiltrating lymphocytes (TIL) were prepared. In addition, the draining lymph nodes were removed for analysis. TIL from GNLY+/− mice expressed granulysin while those from wild type mice did not. Using Western blot of TIL, both 9 kD and 15 kD granulysin were observed, with the 9 kD isoform predominating. Cytokine production and activation marker expression were examined by flow cytometry. GNLY+/− mice had significantly smaller tumor nodules than wild type mice (FIG. 10A), and this correlated with higher levels of IFNγ and TNF production in lymphocytes isolated from the draining nodes (FIG. 10B). Furthermore, antigen-presenting cells from both draining lymph nodes and tumor nodules from the GNLY+/− mice expressed higher levels of CD40 and CD86 (FIG. 10C), indicating that the capacity of T cells to produce granulysin correlates with enhanced costimulatory/coactivating properties of antigen presenting cells in vivo.

Example 19

Effect of 15 kD Granulysin in Primates

The effect of 15 kD granulysin on monocyte differentiation in vitro can be determined in non-human primates. Immune responses can also be determined in vivo in non-human primates, utilizing ex vivo monocyte cells differentiated to dendritic cells in the presence of 15 kD granulysin, co-administered with an antigen. Exemplary methods are described, however, one skilled in the art will appreciate that methods that deviate from these specific methods can also be used to successfully assess the effect of 15 kD granulysin in a primate model.

Peripheral blood mononuclear cells (PBMC) or purified monocytes are collected from rhesus macaques and are cultured with 15 kD granulysin (such as about 1 nM to about 1 μM) or GM-CSF (such as about 10 ng/ml) for 1-5 days. Cells are then stained for cell surface antigens specific to various cell types, such as T cells, B cells, monocytes, NK cells, and dendritic cells. The ability of 15 kD granulysin to promote differentiation of monocytes to immature dendritic cells is assessed by detecting cell surface markers of immature dendritic cells following treatment with 15 kD granulysin.

Monocytes purified from rhesus macaques are cultured with 10 ng/ml GM-CSF and IL-4 (10 ng/ml) for 2-3 days and then 15 kD granulysin is added for about 24 hours. Cell surface markers of mature dendritic cells are assessed (such as CD40, CD80, CD83, and CD86).

Cytokine expression is also assessed in the 15 kD granulysin-differentiated cells. Dendritic cells activated with 15 kD granulysin or GM-CSF are cocultured with allogeneic T cells and expression of TNFα, IFNγ, IL-6, and Il-4 are measured to assess T cell differentiation.

Dendritic cells activated ex vivo with 15 kD granulysin as described above are infused into rhesus macaques with antigen to monitor the effect on in vivo responses.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of stimulating production of a monocyte-derived dendritic cell, comprising contacting a monocyte with 15 kD granulysin, thereby producing a monocyte-derived dendritic cell.

2. The method of claim 1, further comprising contacting the monocyte with an agent that enhances dendritic cell maturation.

3. The method of claim 2, wherein the agent that enhances dendritic cell maturation is selected from the group consisting of GM-CSF, M-CSF, IL-4, IL-6, IL-7, IL-13, flt-3L, TNF-α, IFN-α, CpG motif containing oligonucleotides, toll-like receptors, heparan sulfate, calcium ionophore, lipopolysaccharide, or a combination thereof.

4. A method of enhancing an immune response against a target antigen in a subject, comprising:
   contacting a monocyte with an effective amount of 15 kD granulysin and the target antigen in vitro, thereby producing a monocyte-derived dendritic cell expressing the target antigen; and
   administering the monocyte-derived dendritic cell expressing the target antigen to the subject.

5. The method of claim 4, further comprising contacting the monocyte with an additional agent other than 15 kD granulysin that enhances dendritic cell maturation.

6. The method according to claim 5, wherein the additional agent that enhances dendritic cell maturation is selected from the group consisting of GM-CSF, M-CSF, IL-4, IL-6, IL-7, IL-13, flt-3L, TNF-α, IFN-α, CpG motif containing oligonucleotides, toll-like receptors, heparan sulfate, calcium ionophore, or a combination thereof.

7. A method of generating an activated T lymphocyte in a subject, comprising:
   contacting a monocyte with 15 kD granulysin and a target antigen in vitro, thereby producing a monocyte-derived dendritic cell expressing the target antigen;
   contacting the monocyte-derived dendritic cell expressing the target antigen with a T lymphocyte in vitro, thereby producing an activated T lymphocyte responsive against the target antigen; and,
   administering the activated T lymphocyte responsive against the target antigen to the subject.

8. A method of producing an allospecific T lymphocyte responsive to a monocyte-derived dendritic cell, comprising:
   contacting a monocyte with 15 kD granulysin, thereby producing a monocyte-derived dendritic cell; and
   contacting the monocyte-derived dendritic cell with a T lymphocyte, thereby producing the allospecific T lymphocyte responsive to the monocyte-derived dendritic cell.

9. The method of claim 8, further comprising contacting the monocyte-derived dendritic cell with a target antigen prior to contacting the monocyte-derived dendritic cell with the T lymphocyte.

* * * * *

SEQUENCE LISTING

<160> NUMBER OF SEQ ID NOS: 2

<210> SEQ ID NO 1
<211> LENGTH: 123
<212> TYPE: PRT
<213> ORGANISM: Homo sapiens

<400> SEQUENCE: 1

```
Arg Leu Ser Pro Glu Tyr Tyr Asp Leu Ala Arg Ala His Leu Arg Asp
1               5                   10                  15

Glu Glu Lys Ser Cys Pro Cys Leu Ala Gln Glu Gly Pro Gln Gly Asp
            20                  25                  30

Leu Leu Thr Lys Thr Gln Glu Leu Gly Arg Asp Tyr Arg Thr Cys Leu
        35                  40                  45

Thr Ile Val Gln Lys Leu Lys Lys Met Val Asp Lys Pro Thr Gln Arg
    50                  55                  60

Ser Val Ser Asn Ala Ala Thr Arg Val Cys Arg Thr Gly Arg Ser Arg
65                  70                  75                  80

Trp Arg Asp Val Cys Arg Asn Phe Met Arg Arg Tyr Gln Ser Arg Val
                85                  90                  95

Thr Gln Gly Leu Val Ala Gly Glu Thr Ala Gln Gln Ile Cys Glu Asp
            100                 105                 110

Leu Arg Leu Cys Ile Pro Ser Thr Gly Pro Leu
        115                 120
```

<210> SEQ ID NO 2

<211> LENGTH: 995
<212> TYPE: DNA
<213> ORGANISM: Homo sapiens

<400> SEQUENCE: 2

| | | | | | |
|---|---|---|---|---|---|
| gtatctgtgg | taaacccagt | gacacggggg | agatgacata | caaaaagggc | aggacctgag | 60 |
| aaagattaag | ctgcaggctc | cctgcccata | aacagggtg | tgaaaggcat | ctcagcggct | 120 |
| gccccaccat | ggctacctgg | gccctcctgc | tccttgcagc | catgctcctg | ggcaacccag | 180 |
| ccctgcctc | cgcatctgcg | tggtgaaggc | cattggccct | catcggtgga | tctgcgtttc | 240 |
| ctcgggccta | cactgtctag | gattgtgcgg | ggctggtgag | agaacaagat | ctcttctgtg | 300 |
| ttcaaggcag | acttcctgcc | ccctgcaccc | tgctctctcc | caggccttga | ggtcagtgtg | 360 |
| agccccaagg | gcaagaacac | ttctggaagg | gagagtggat | ttggctgggc | catctggatg | 420 |
| gaaggtctgg | tcttctctcg | tctgagccct | gagtactacg | acctggcaag | agcccacctg | 480 |
| cgtgatgagg | agaaatcctg | cccgtgcctg | gcccaggagg | gcccccaggg | tgacctgttg | 540 |
| accaaaacac | aggagctggg | ccgtgactac | aggacctgtc | tgacgatagt | ccaaaaactg | 600 |
| aagaagatgg | tggataagcc | cacccagaga | agtgtttcca | atgctgcgac | ccgggtgtgt | 660 |
| aggacgggga | ggtcacgatg | gcgcgacgtc | tgcagaaatt | tcatgaggag | gtatcagtct | 720 |
| agagttaccc | agggcctcgt | ggccggagaa | actgcccagc | agatctgtga | ggacctcagg | 780 |
| ttgtgtatac | cttctacagg | tccctctga | gccctctcac | cttgtcctgt | ggaagaagca | 840 |
| caggctcctg | tcctcagatc | ccgggaacct | cagcaacctc | tgccggctcc | tcgcttcctc | 900 |
| gatccagaat | ccactctcca | gtctccctcc | cctgactccc | tctgctgtcc | tcccctctca | 960 |
| cgagaataaa | gtgtcaagca | agattttaaa | aaaaa | | | 995 |